US007689022B2

(12) United States Patent
Weiner et al.

(10) Patent No.: US 7,689,022 B2
(45) Date of Patent: Mar. 30, 2010

(54) SYSTEM, METHOD, AND PRODUCT FOR SCANNING OF BIOLOGICAL MATERIALS

(75) Inventors: Nathan K. Weiner, Upton, MA (US); Patrick J. Odoy, Rowley, MA (US); Erik Schultz, North Andover, MA (US); Mark Jones, Reading, MA (US); James Overbeck, Hingham, MA (US); Herman Deweerd, Bedford, MA (US); David A. Stura, North Billerica, MA (US); Albert Bukys, Lexington, MA (US); Tim Woolaver, Billerica, MA (US); Thomas P. Regan, Dover, MA (US); David Bradbury, Ipswich, MA (US); Eric Earl McKenzie, Dunstable, MA (US); Roger DiPaolo, Leominster, MA (US); Christopher Miles, Acton, MA (US); Joel Katz, Stoneham, MA (US); Ksenia Oleink-Ovod, Newton, MA (US)

(73) Assignee: Affymetrix, Inc., Santa Clara, CA (US)

( * ) Notice: Subject to any disclaimer, the term of this patent is extended or adjusted under 35 U.S.C. 154(b) by 2144 days.

(21) Appl. No.: 10/389,194

(22) Filed: Mar. 14, 2003

(65) Prior Publication Data

US 2004/0012676 A1    Jan. 22, 2004

Related U.S. Application Data

(60) Provisional application No. 60/364,731, filed on Mar. 15, 2002, provisional application No. 60/396,457, filed on Jul. 17, 2002, provisional application No. 60/435,178, filed on Dec. 19, 2002.

(51) Int. Cl.
*G06K 9/00* (2006.01)

(52) U.S. Cl. ........................ 382/133; 382/255
(58) Field of Classification Search ................. 382/128, 382/133, 134, 255; 250/201.2, 201.3, 201.4, 250/201.7
See application file for complete search history.

(56) References Cited

U.S. PATENT DOCUMENTS 4,185,274 A    1/1980 Giallorenzi .............. 340/347 P (Continued)

FOREIGN PATENT DOCUMENTS

EP    0 864 858 A2    9/1998

(Continued)

OTHER PUBLICATIONS

Jean Montagu and Nathan Weiner, Fluorescence Array Scanner Employing a Flying Objective; Journal of the Association for Laboratory Automation, Mar. 1999, vol. 4, No. 1.

(Continued)

*Primary Examiner*—Andrew W Johns
(74) *Attorney, Agent, or Firm*—Thomas J. Siepmann

(57) ABSTRACT

An embodiment of a scanning system is described including optical elements that direct an excitation beam at a probe array, detectors that receive reflected intensity data responsive to the excitation beam, where the reflected intensity data is responsive to a focusing distance between an optical element and the probe array, a transport frame that adjusts the focusing distance in a direction with respect to the probe array, an auto-focuser that determines a best plane of focus based upon characteristics of the reflected intensity data of at least two focusing distances where the detectors further receive pixel intensity values based upon detected emissions from a plurality of probe features disposed on the probe array at the best plane of focus, and an image generator that associates each of the pixel intensity values with at least one image pixel position of a probe array based upon one or more position correction values.

21 Claims, 33 Drawing Sheets

U.S. PATENT DOCUMENTS

| | | | |
|---|---|---|---|
| 4,410,799 A | 10/1983 | Okamoto | 250/327.2 |
| 4,665,034 A | 5/1987 | Chandler | 435/287 |
| 4,758,727 A | 7/1988 | Tomei et al. | 250/458.1 |
| 4,829,010 A | 5/1989 | Chang | 422/58 |
| 4,855,597 A | 8/1989 | Shimura | 250/327.2 |
| 4,859,419 A | 8/1989 | Marks et al. | 422/56 |
| 4,877,966 A | 10/1989 | Tomei et al. | 250/458.1 |
| 4,890,247 A | 12/1989 | Sarrine et al. | 364/571.04 |
| 5,032,720 A | 7/1991 | White | 250/236 |
| 5,093,978 A | 3/1992 | Binder | 29/568 |
| 5,102,177 A | 4/1992 | Dreisig et al. | 294/106 |
| 5,104,808 A | 4/1992 | Laska et al. | 436/48 |
| 5,121,138 A | 6/1992 | Schermer et al. | 346/108 |
| 5,143,854 A | 9/1992 | Pirrung et al. | 436/518 |
| 5,154,888 A | 10/1992 | Zander et al. | 422/58 |
| 5,229,297 A | 7/1993 | Schniplesky et al. | 436/94 |
| 5,230,866 A | 7/1993 | Shartle et al. | 422/103 |
| 5,233,844 A | 8/1993 | Knippscheer et al. | 62/440 |
| 5,258,781 A | 11/1993 | John | 347/140 R |
| 5,279,721 A | 1/1994 | Schmid | 204/182.8 |
| 5,288,463 A | 2/1994 | Chemelli | 422/58 |
| 5,296,195 A | 3/1994 | Pang et al. | 422/82.05 |
| 5,302,824 A | 4/1994 | Prager | 250/252.1 |
| 5,384,261 A | 1/1995 | Winkler et al. | 436/518 |
| 5,388,945 A | 2/1995 | Garric et al. | 414/217 |
| 5,422,271 A | 6/1995 | Chen et al. | 435/287.2 |
| 5,424,186 A | 6/1995 | Fodor et al. | 435/6 |
| 5,434,595 A | 7/1995 | Macaulay | 345/207 |
| 5,436,129 A | 7/1995 | Stapleton | 435/6 |
| 5,459,325 A | 10/1995 | Hueton et al. | 250/458.1 |
| 5,486,335 A | 1/1996 | Wilding et al. | 422/55 |
| 5,489,678 A | 2/1996 | Fodor et al. | 536/22.1 |
| 5,500,187 A | 3/1996 | Deoms et al. | 422/58 |
| 5,528,050 A | 6/1996 | Miller et al. | 250/585 |
| 5,538,613 A | 7/1996 | Brumley et al. | 204/612 |
| 5,543,329 A | 8/1996 | Bedell | 435/7.32 |
| 5,578,832 A | 11/1996 | Trulson et al. | 250/458.1 |
| 5,585,639 A | 12/1996 | Dorsel et al. | 250/458.1 |
| 5,587,128 A | 12/1996 | Wilding et al. | 422/50 |
| 5,593,838 A | 1/1997 | Zanzucchi et al. | 435/6 |
| 5,593,839 A | 1/1997 | Hubbell et al. | 435/6 |
| 5,595,908 A | 1/1997 | Fawcett et al. | 435/287.2 |
| 5,599,504 A | 2/1997 | Hosoi et al. | 422/82.08 |
| 5,627,041 A | 5/1997 | Shartle | 435/7.24 |
| 5,631,734 A | 5/1997 | Stern et al. | 356/317 |
| 5,635,358 A | 6/1997 | Wilding et al. | 435/7.2 |
| 5,637,469 A | 6/1997 | Wilding et al. | 435/7.21 |
| 5,652,149 A | 7/1997 | Mileaf et al. | 436/518 |
| 5,658,802 A | 8/1997 | Hayes et al. | 436/518 |
| 5,674,743 A | 10/1997 | Ulmer | 435/287.2 |
| 5,675,700 A | 10/1997 | Atwood et al. | 392/382 |
| 5,683,916 A | 11/1997 | Goffe et al. | 436/535 |
| 5,689,110 A | 11/1997 | Dietz et al. | 250/252.1 A |
| 5,698,450 A | 12/1997 | Ringrose et al. | 436/526 |
| 5,716,825 A | 2/1998 | Hancock et al. | 435/286.5 |
| 5,726,010 A | 3/1998 | Clark | 435/5 |
| 5,726,013 A | 3/1998 | Clark | 435/5 |
| 5,763,870 A | 6/1998 | Sadler et al. | 250/201.2 |
| 5,834,758 A | 11/1998 | Trulson et al. | 250/201.2 |
| 5,895,915 A | 4/1999 | DeWeerd et al. | 250/234 |
| 5,936,324 A | 8/1999 | Montagu | 310/156 |
| 5,945,334 A | 8/1999 | Besemer et al. | 435/287.2 |
| 5,954,804 A | 9/1999 | Farmwald et al. | 710/36 |
| 5,962,834 A | 10/1999 | Markman | 235/385 |
| 5,981,956 A | 11/1999 | Stern | 250/458.1 |
| 5,984,474 A | 11/1999 | Schweitzer et al. | 351/205 |
| 6,025,601 A | 2/2000 | Trulson et al. | 250/461.2 |
| 6,036,781 A | 3/2000 | Ahn et al. | 118/715 |
| 6,042,324 A | 3/2000 | Aggarwal et al. | 414/411 |
| 6,068,437 A | 5/2000 | Boje et al. | 414/331.02 |
| 6,072,417 A | 6/2000 | Staton | 341/165 |
| 6,073,366 A | 6/2000 | Aswad | 34/367 |
| 6,075,613 A | 6/2000 | Schermer et al. | 356/446 |
| 6,078,390 A | 6/2000 | Bengtsson | 356/318 |
| 6,097,025 A | 8/2000 | Modlin et al. | 250/227.22 |
| 6,130,440 A | 10/2000 | Ogura | 250/596 |
| 6,141,096 A | 10/2000 | Stern et al. | 356/318 |
| 6,166,367 A | 12/2000 | Cho | 250/208.1 |
| 6,166,385 A | 12/2000 | Webb et al. | 250/458.1 |
| 6,169,289 B1 | 1/2001 | White et al. | 250/458.1 |
| 6,171,793 B1 | 1/2001 | Phillips et al. | 435/6 |
| 6,185,030 B1 | 2/2001 | Overbeck | 359/225 |
| 6,201,639 B1 | 3/2001 | Overbeck | 359/368 |
| 6,209,983 B1 | 4/2001 | Osborne et al. | 347/32 |
| 6,211,913 B1 | 4/2001 | Hansen et al. | 348/239 |
| 6,211,989 B1 | 4/2001 | Wulf et al. | 359/210 |
| 6,218,803 B1 | 4/2001 | Montagu et al. | 318/662 |
| 6,225,625 B1 | 5/2001 | Pirrung et al. | 250/302 |
| 6,229,607 B1 | 5/2001 | Shirai et al. | 356/375 |
| 6,245,507 B1 | 6/2001 | Bogdanov | 436/6 |
| 6,309,601 B1 | 10/2001 | Juncosa et al. | 422/68.1 |
| 6,312,914 B1 | 11/2001 | Kardos et al. | 436/6 |
| 6,347,259 B1 | 2/2002 | Goldenberg et al. | 700/218 |
| 6,352,861 B1 | 3/2002 | Copeland et al. | 436/46 |
| 6,353,475 B1 | 3/2002 | Jensen et al. | 356/244 |
| 6,395,554 B1 | 5/2002 | Regan et al. | 436/46 |
| 6,490,533 B2 | 12/2002 | Weiner et al. | 702/27 |
| 6,507,426 B2 | 1/2003 | Makino | 359/196 |
| 6,511,277 B1 | 1/2003 | Norris et al. | 414/331.05 |
| 6,518,556 B2 | 2/2003 | Staton et al. | 250/207 |
| 6,545,758 B1 | 4/2003 | Sandstrom | 356/317 |
| 6,555,802 B2 | 4/2003 | Osipchuk et al. | 250/201.3 |
| 6,592,036 B2 | 7/2003 | Sadler et al. | 235/454 |
| 7,023,369 B2 | 4/2006 | Bocko et al. | 341/143 |
| 2002/0017562 A1 | 2/2002 | Sadler et al. | 235/454 |
| 2002/0018199 A1 | 2/2002 | Blumenfeld et al. | 356/73 |
| 2002/0024026 A1 | 2/2002 | Kaushikkar | 250/559.06 |
| 2002/0043625 A1 | 4/2002 | Shimizu et al. | 250/458.1 |
| 2002/0070330 A1 | 6/2002 | Staton et al. | 250/207 |
| 2002/0102559 A1 | 8/2002 | Cattell | 436/6 |
| 2002/0109009 A1 | 8/2002 | Sadler et al. | 235/454 |
| 2002/0195554 A1 | 12/2002 | Staton et al. | 250/252.1 |
| 2003/0001072 A1 | 1/2003 | Dorsel et al. | 250/201.5 |
| 2003/0032191 A1 | 2/2003 | Hilson et al. | 436/47 |
| 2003/0168579 A1 | 9/2003 | Corson et al. | 250/214 R |
| 2003/0203492 A1 | 10/2003 | Sillman | 436/46 |
| 2005/0057676 A1 | 3/2005 | Weiner et al. | 348/331 |
| 2005/0059062 A1 | 3/2005 | Kaiser | 435/6 |
| 2005/0063806 A1 | 3/2005 | Norris et al. | 414/403 |
| 2005/0158819 A1 | 7/2005 | Besemer et al. | 435/68.1 |

FOREIGN PATENT DOCUMENTS

| | | |
|---|---|---|
| EP | 0 957 642 A2 | 11/1999 |
| EP | 0 990 896 A2 | 4/2000 |
| EP | 1 031 812 A2 | 8/2000 |
| EP | 1 186 673 A2 | 3/2002 |
| EP | 0 746 865 B1 | 3/2003 |
| JP | 2000125174 A | 4/2000 |
| JP | 2000151971 A | 5/2000 |
| JP | 2000261618 A | 9/2000 |
| WO | WO 89/10977 A1 | 11/1989 |

| | | |
|---|---|---|
| WO | WO 89/11548 A1 | 11/1989 |
| WO | WO 90/15070 A1 | 12/1990 |
| WO | WO 92/10092 A1 | 6/1992 |
| WO | WO 93/09668 A1 | 5/1993 |
| WO | WO 95/33846 A1 | 12/1995 |
| WO | WO 98/35223 A1 | 8/1998 |
| WO | WO 99/47964 A1 | 9/1999 |
| WO | WO 01/35080 A1 | 5/2001 |
| WO | WO 01/35099 A1 | 5/2001 |

OTHER PUBLICATIONS

Fodor, et al, "Light-Directed, Spatially Addressable Parallel Chemical Synthesis," Research Article, Science, 251:767-773 (Feb. 15, 1991).

Agilent Technologies Press Release, Agilent Technologies Announces Launch of Next-Generation Fully Automated DNA Microarray Scanner, Palo Alto, CA, Jun. 25, 2001.

U.S. Appl. No. 10/623,883, filed Jul. 21, 2003, Lobban et al.

SYSTEM, METHOD, AND PRODUCT FOR SCANNING OF BIOLOGICAL MATERIALS

RELATED APPLICATIONS

The present application claims priority from U.S. Provisional Patent Application Ser. No. 60/364,731, entitled "SYSTEM, METHOD, AND PRODUCT FOR SCANNING OF BIOLOGICAL MATERIALS," filed Mar. 15, 2002; U.S. Provisional Patent Application Ser. No. 60/396,457, titled "HIGH-THROUGHPUT MICROARRAY SCANNING SYSTEM AND METHOD", filed Jul. 17, 2002; and U.S. Provisional Patent Application Ser. No. 60/435,178, titled "System, Method and Product for Scanning of Biological Materials", filed Dec. 19, 2002, each of which is hereby incorporated by reference herein in it's entirety for all purposes.

BACKGROUND

1. Field of the Invention

The present invention relates to systems and methods for examining biological material. In particular, the invention relates to improved optical readers or scanners for detecting emissions from biological probe arrays having small features that may be arranged in high densities on the arrays.

2. Related Art

Synthesized nucleic acid probe arrays, such as Affymetrix GeneChip® probe arrays, and spotted probe arrays, have been used to generate unprecedented amounts of information about biological systems. For example, the GeneChip® Human Genome U133 Set (HG-U133A and HG-U133B) available from Affymetrix, Inc. of Santa Clara, Calif., is comprised of two microarrays containing over 1,000,000 unique oligonucleotide features covering more than 39,000 transcript variants that represent more than 33,000 human genes. Analysis of expression data from such microarrays may lead to the development of new drugs and new diagnostic tools.

SUMMARY OF THE INVENTION

Systems, methods, and products to address these and other needs are described herein with respect to illustrative, non-limiting, implementations. Various alternatives, modifications and equivalents are possible. For example, certain systems, methods, and computer software products are described herein using exemplary implementations for analyzing data from arrays of biological materials produced by the Affymetrix® 417™ or 427™ Arrayer. Other illustrative implementations are referred to in relation to data from Affymetrix® GeneChip® probe arrays. However, these systems, methods, and products may be applied with respect to many other types of probe arrays and, more generally, with respect to numerous parallel biological assays produced in accordance with other conventional technologies and/or produced in accordance with techniques that may be developed in the future. For example, the systems, methods, and products described herein may be applied to parallel assays of nucleic acids, PCR products generated from cDNA clones, proteins, antibodies, or many other biological materials. These materials may be disposed on slides (as typically used for spotted arrays), on substrates employed for GeneChip® arrays, or on beads, optical fibers, or other substrates or media, which may include polymeric coatings or other layers on top of slides or other substrates. Moreover, the probes need not be immobilized in or on a substrate, and, if immobilized, need not be disposed in regular patterns or arrays. For convenience, the term "probe array" will generally be used broadly hereafter to refer to all of these types of arrays and parallel biological assays.

In accordance with a particular embodiment, a scanning system is described including optical elements that direct an excitation beam at a probe array, detectors that receive reflected intensity data responsive to the excitation beam, where the reflected intensity data is responsive to a focusing distance between an optical element and the probe array, a transport frame that adjusts the focusing distance in a direction with respect to the probe array, an auto-focuser that determines a best plane of focus based upon characteristics of the reflected intensity data of at least two focusing distances where the detectors further receive pixel intensity values based upon detected emissions from a plurality of probe features disposed on the probe array at the best plane of focus, and an image generator that associates each of the pixel intensity values with at least one image pixel position of a probe array based upon one or more position correction values.

In accordance with another embodiment a method is described that includes the acts of receiving pixel intensity values based upon detected emissions from probe features disposed on a probe array, and associating each of the pixel intensity values with image pixel positions of a probe array image based upon position correction values.

In some implementations, the probe array image has a position error of plus or minus one pixel or less, and the emissions are responsive to an excitation beam and arise from excitation by the excitation beam of fluorescent molecules. The excitation beam includes a laser beam generated by a solid state, diode pumped, frequency doubled Nd:YAG laser. The act of receiving pixel intensity values is accomplished in a single pass of the excitation beam over a number of contiguous probe features of the plurality of probe features.

The contiguous features may include probe features that are immediately adjacent to each other or are separated by non-feature areas of the probe array. A scanning line may comprise a number of contiguous features. Additionally, each of the pixel intensity values may be associated with a pixel having a dimension in an x-axis with respect to the probe array of approximately 2.5 µm, or in a range between about 1.5 µm and about 3.0 µm. Also, each of the probe features has a dimension in an x-axis with respect to the probe array of approximately 18 µm, or in a range of between about 14 µm and about 22 µm. Similarly, each of the probe features may have a dimension in an x-axis with respect to the probe array of approximately 10 µm, or in a range of about 6 µm and about 14 µm. Each probe feature may be associated with one or more of the pixel intensity values.

Also in some implementations, the biological probe array includes a synthesized array or a spotted array, and the position correction values each include a horizontal linearity correction value, a vertical linearity correction value, or both. The act of associating each of the pixel intensity values with image pixel positions is accomplished by adjusting a received pixel position associated with each of the pixel intensity values by a number of pixels determined by the one or more position correction values, where the number of pixels includes a fractional value and the one or more position correction values may be based upon one or more reference positions provided by one or more calibration features. The one or more calibration features comprises an array of features oriented in a horizontal pattern, vertical pattern, or both.

In some embodiments the method further comprises the acts of translating the probe array a distance along a y-axis with respect to the probe array, and repeating the steps of receiving, associating, and translating until the probe array image includes pixel intensity values corresponding to each of the plurality of probes disposed on the probe array. The distance may based, at least in part, on a size of a pixel in the y-axis, and include a distance of approximately 2.5 µm, or include a distance in a range between about 1.5 µm and about 3.0 µm.

In accordance with other embodiments a scanning system is described, including one or more detectors that receive a plurality of pixel intensity values based upon detected emissions from probe features disposed on a probe array, and a corrected image generator that associates each of the pixel intensity values with one or more image pixel positions of a probe array image based upon one or more position correction values.

In some impelementations, the scanning further includes a transport frame that translates the probe array a distance along a y-axis with respect to the probe array, and a comparator that is determine a completed probe array image based, at least in part, upon one or more received pixel intensity values corresponding to each of the plurality of probes disposed on the probe array. The transport frame further provides a solid hinge flexure that may provide movement in the Z-axis, and has no friction or stiction.

In accordance with yet another embodiment, a method is described including the acts of directing an excitation beam at a probe array, receiving reflected intensity data responsive to the excitation beam, where the intensity data is responsive to a focusing distance between an optical element and the probe array, adjusting the focusing distance in a direction with respect to the probe array, repeating the steps of receiving and adjusting for a number of iterations, and determining a best plane of focus based upon one or more characteristics of the reflected intensity data at the adjusted focusing distances.

In some implementations the direction is away from or toward the probe array, the number of iterations may be predetermined. The predetermined number of iterations is based on an anticipated error associated with the reflected intensity data where the anticipated error may be inversely related to the predetermined number of iterations. Also, the reflected intensity data may be responsive to reflection of the excitation beam from one or more focus features, and may correspond to one or more reflection spots. The best plane of focus may be based upon associating the one or more spots with one or more characteristics of a beam waist. Additionally, the one or more focus features may be positioned outside an active area and the one or more probe features are positioned inside the active area.

Also, in some implementations the one or more focus features may include a chrome border, and the one or more characteristics may include a slope value. The best plane of focus may be based upon a maximum value of the slope value.

In accordance with another embodiment, a scanning system is described, including one or more optical elements that direct an excitation beam at a probe array, one or more detectors that receive reflected intensity data responsive to the excitation beam where the intensity data may be determined by a focusing distance between an optical element and the probe array, and an auto-focuser constructed and arranged to determine a best plane of focus based upon one or more characteristics of the reflected intensity data as received at two or more focusing distances.

In accordance with a further embodiment, a method is described including the acts of storing one or more probe arrays in a magazine where each of the plurality of probe arrays is housed in a probe array cartridge, reversibly transporting a first probe array cartridge between the magazine and a scanning system, and advancing the magazine by one or more positions to a second probe array cartridge.

In some implementations the act of storing includes providing a temperature and humidity controlled environment that includes maintaining the probe arrays at a temperature for maintaining biological integrity. The temperature for maintaining biological integrity may includes a range between about 2° C. and 15° C. Also each of the one or more probe arrays may be arranged in a vertical orientation, and the magazine holds at least 48 or 100 probe arrays. The magazine is substantially circular.

Additionally, in some implementations condensation on at least one of the probe array cartridges may be reduced by warming. The act of transporting may also include one or more elements that reversibly engage and disengage one or more fiducial features of the probe array cartridge.

In accordance with an additional embodiment, a scanning system is described, including a cooled storage chamber that stores one or more probe arrays in a magazine where each of the probe arrays is housed in a probe array cartridge, a cartridge transport assembly that reversibly transports a first probe array cartridge between the magazine and a scanning system, and a linear motor that advances the magazine by one or more positions to a second probe array cartridge.

In accordance with another embodiment, a scanning system is described including a service application that performs one or more calibration methods that also includes an interface to elements of the scanning system.

In some impelementations, the one or more calibration methods include pitch calibration, roll calibration, and arc radius calibration, and the elements includes hardware elements. The service application is further runs one or more diagnostic tests, and uploads and/or downloads one or more software or firmware applications.

The above embodiments and implementations are not necessarily inclusive or exclusive of each other and may be combined in any manner that is non-conflicting and otherwise possible, whether they be presented in association with a same, or a different, embodiment or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above embodiment and implementations are illustrative rather than limiting.

BRIEF DESCRIPTION OF THE DRAWINGS

The above and further features will be more clearly appreciated from the following detailed description when taken in conjunction with the accompanying drawings. In the drawings, like reference numerals indicate like structures or method steps and the leftmost digit of a reference numeral indicates the number of the figure in which the referenced element first appears (for example, the element 160 appears first in FIG. 1). In functional block diagrams, rectangles generally indicate functional elements and parallelograms generally indicate data. In method flow charts, rectangles generally indicate method steps and diamond shapes generally indicate decision elements. All of these conventions, however, are intended to be typical or illustrative, rather than limiting.

DETAILED DESCRIPTION

The description below is designed to present specific embodiments and not to be construed as limiting in any way. Also, reference will be made to articles and patents to show general features that are incorporated into the present disclosure, but the invention is not limited by these descriptions. Many scanner designs may be used in order to provide excitation and emission signals appropriate for the acquisition of experimental data derived from probe array 240.

Figure 1:
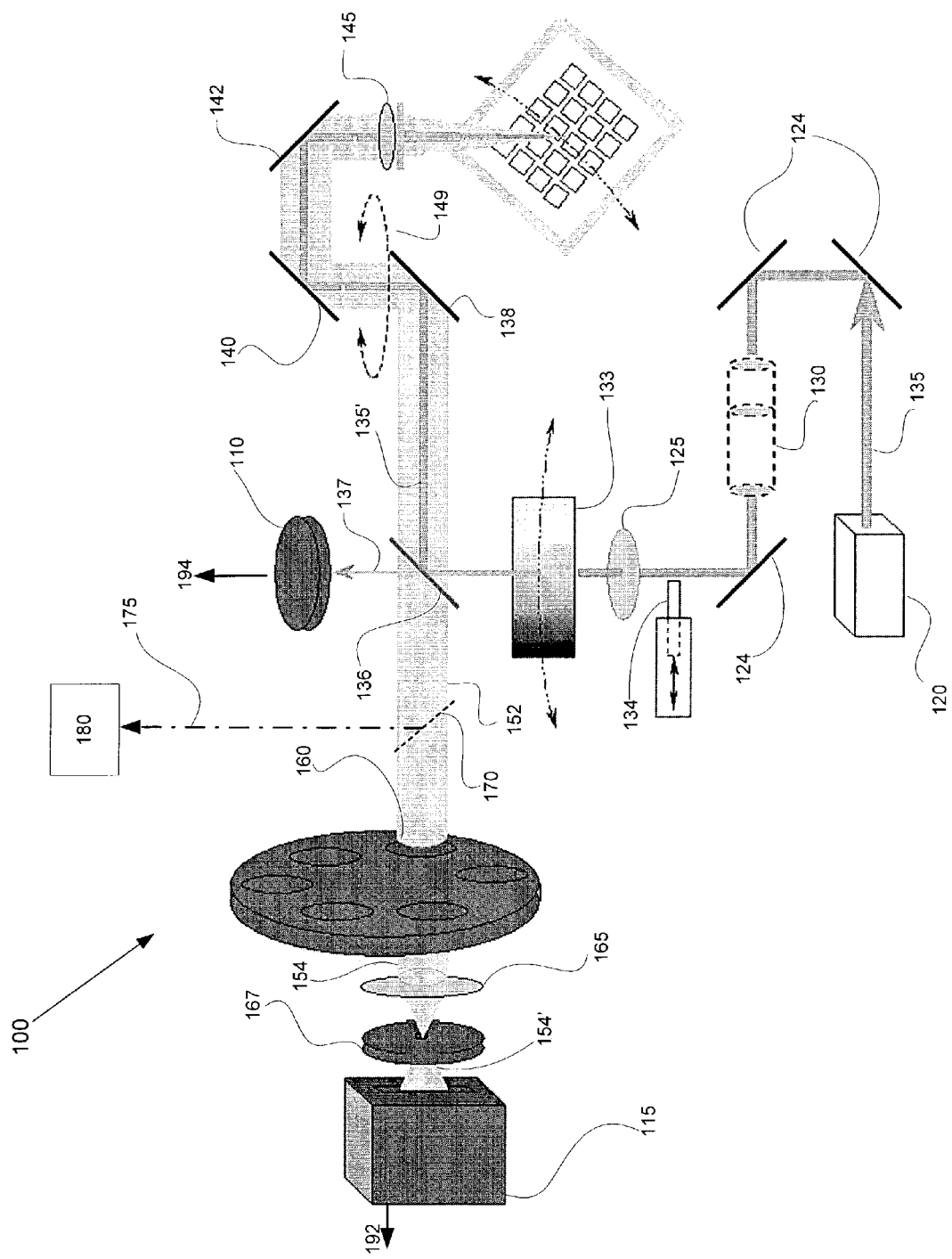
FIG. 1 is a simplified graphical representation of an arrangement of scanner optics and detectors suitable for providing excitation and emission signals.

In reference to the illustrative implementation of FIG. 1, the term "excitation beam" refers to light beams generated by lasers. However, excitation sources other than lasers may be used in alternative implementations. For example, other implementations may use light emitting diodes, an incandescent light source, or any other light or other electromagnetic source of energy having a wavelength in the excitation band of an excitable label, or capable of providing detectable transmitted, reflective, or diffused radiation. Thus, the term "excitation beam" is used broadly herein. The term "emission beam" also is used broadly herein. A variety of conventional scanners detect fluorescent or other emissions from labeled target molecules or other material associated with biological probes. Other conventional scanners detect transmitted, reflected, or scattered radiation from such targets. These processes are sometimes generally and collectively referred to hereafter for convenience simply as involving the detection of "emission beams." Various detection schemes are employed depending on the type of emissions and other factors. A typical scheme employs optical and other elements to provide an excitation beam, such as from a laser, and to selectively collect the emission beams. Also generally included are various light-detector systems employing photodiodes, charge-coupled devices, photomultiplier tubes, or similar or other conventional devices to register the collected emission beams. For example, a scanning system for use with a fluorescently labeled target is described in U.S. Pat. Nos. 5,143,854 and 6,225,625, hereby incorporated by reference in their entireties for all purposes. Other scanners or scanning systems are described in U.S. Pat. Nos. 5,578,832; 5,631,734; 5,834,758; 5,936,324; 5,981,956; 6,025,601; 6,141,096; 6,185,030; 6,201,639; 6,207,960; 6,218,803; 6,252,236; 6,335,824; 6,490,533; 6,407,858; and 6,403,320; and in PCT Application PCT/US99/06097 (published as WO99/47964), each of which also is hereby incorporated by reference in its entirety for all purposes.

One embodiment of a scanning system as described above may serve a variety of functions. For example, some functions could include what those of ordinary skill in the related art refer to as expression analysis and/or genotyping. Genotyping could further include functions such as identification of single nucleotide polymorphisms, DNA sequencing, loss of heterozygosity identification, or transcriptome analysis. The previous examples are for the purposes of illustration only and it will be appreciated to those of ordinary skill in the art that many additional functions may exist. An additional example of a function could include diagnostic or other type of clinical uses. For instance, the diagnostic function could include the analysis of patient samples for the purpose of identifying the existence or potential threat of health problems.

Additionally, a particularly embodiment of a scanning system as described herein is constructed and arranged to accurately image features of a probe array that may include feature sizes of 18 μm, 10 μm, or smaller in a dimension (such as the side of a square or side of a rectangle). Accurately imaging very small feature sizes generally requires that tolerances for error associated with the hardware and software elements of a scanning system be similarly small such as, for instance, allowable position error may not exceed +/−1 pixel of an acquired image. Due to a variety of factors, multiple pixels are generally collected for every feature; for example, a range of 4-64 pixels may be acquired for each feature depending upon feature size of the particular implementation of probe array 240.

Scanner Optics and Detectors 100: FIG. 1 is a simplified graphical representation of illustrative scanner optics and detectors (hereafter, simply "scanner optics") 100. Although only one excitation source 120 is shown in the illustrated examples, any number of one or more excitation sources 120 may be used in alternative embodiments. In the present example, source 120 is a laser; in this embodiment a solid state, diode pumped, frequency doubled Nd: YAG (Neodymium-doped Yttrium Aluminum Garnet) or YVO₄ laser producing green laser light having a wavelength of 532 nm. Only one laser and accordingly, only one illumination beam is used during each scan. Further references herein to source 120 generally will assume for illustrative purposes that they are lasers, but, as noted, other types of sources, e.g., x-ray sources, may be used in other implementations. The *Handbook of Biological Confocal Microscopy* (James B. Pawley, ed.) (2.ed.; 1995; Plenum Press, NY), includes information known to those of ordinary skill in the art regarding the use of lasers and associated optics, is hereby incorporated herein by reference in its entirety.

FIG. 1 further provides an illustrative example of the paths of excitation beam 135 and emission beam 152 and a plurality of optical components that comprise scanner optics 100. In the present example, excitation beam 135 is emitted from source 120 and is directed along an optical path by one or more turning mirrors 124 toward a three-lens beam conditioner/expander 130. Turning mirrors are used in the optics module to provide the necessary adjustments to the optical path to allow for alignment of the excitation beam at the objective lens and to allow for alignment of the emission beam at the fluorescent detection module. The turning mirrors also serve to "fold" the optical path into a more compact size & shape to facilitate overall scanner packaging. The number of turning mirrors may vary in different embodiments and may depend on the requirements of the optical path. For instance, if the optical path is required to turn a number of corners, such as 2 or more, then a corresponding number of turning mirrors 124 may be required to meet the optical path requirements.

In some embodiments it may be desirable that excitation beam 135 has a known diameter. Beam conditioner/expander 130 may provide one or more optical elements that adjust a beam diameter to a value that could, for instance, include a diameter of 1.076 mm±10%. For example, the one or more optical elements could include a three-lens beam expander that may increase the diameter of excitation beam 135 to a desired value. Alternatively, the one or more optical elements may reduce the diameter of excitation beam 135 to a desired value. Additionally, the one or more optical elements of beam conditioner/expander 130 may further condition one or more properties of excitation beam 135 to provide other desirable characteristics, such as providing what those of ordinary skill in the related art refer to as a plane wavefront to objective lens 145. Excitation beam 135 with the desirable characteristics may then exit beam conditioner/expander 130 and continue along the optical path that may again be redirected by one or more turning mirrors 124 towards excitation filter 125.

Filter 125 may be used to remove light at wavelengths other than excitation wavelengths, and generally need not be included if, for example, source 120 does not produce light at these extraneous wavelengths. However, it may be desirable in some applications to use inexpensive lasers and often it is cheaper to filter out-of-mode laser emissions than to design the laser to avoid producing such extraneous emissions. In some embodiments, filter 125 allows all or a substantial portion of light at the excitation wavelengths to pass through without affecting other characteristics of excitation beam 135, such as the desirable characteristics modified by beam conditioner/expander 130. For example, an excitation wavelength may include 532 nanometer (nm) that may excite one or more fluorophores including, for instance, R-phycoerythrin.

After exiting filter 125 excitation beam 135 may then be directed along the optical path to laser attenuator 133. Laser attenuator 133 may provide a means for adjusting the level of power of excitation beam 135. In some embodiments, attenuator 133 may, for instance, be comprised of a variable neutral density filter. Those of ordinary skill in the related art will appreciate that neutral density filters, such as absorptive, metallic, or other type of neutral density filter, may be used for reducing the amount of light that is allowed to pass through. The amount of light reduction may depend upon what is referred to as the density of the filter, for instance, as the density increases the amount of light allowed to pass through decreases. The neutral density filter may additionally include a density gradient. For example, the presently described embodiment may include laser attenuator 133 that includes a neutral density filter with a density gradient. Attenuator 133, acting under the control of scanner firmware executables 672 using one or more parameters supplied by scanner control and analysis executables 572, may use a step motor that alters the position of the neutral density filter with respect to the optical path. Attenuator 133 may make adjustments to the level of laser power delivered to the probe array based, at least in part, upon instructions from firmware executables 672. The adjustments may be made by placing a specific density of the neutral density filter gradient, associated with a desired laser power, in the optical path. The neutral density filter thus reduces the amount of light allowed to pass through to a desired level, as measured by laser power monitor 110, described in detail below.

Some embodiments may include one or more implementations of shutter 134. Some implementations may include positioning shutter 134 in one or more locations within scanner 400, along the optical path such that shutter 134 provides a means to block all laser light from reaching probe array 240, and in some implementations additionally blocking all laser light from reaching laser power monitor 110. Shutter 134 may use a variety of means to completely block the light beam. For example shutter 134 may use a motor under the control of scanner firmware executables 672 to extend/retract a solid barrier that could be constructed of metal, plastic, or other appropriate material capable of blocking essentially all of the laser light beam, such as excitation beam 135. Shutter 134 may be used for a variety of purposes such as, for example, for blocking all light from one or more photo detectors or monitors, including emission detector 115 and laser power monitor 110. In the present example, blocking the light may be used for calibration methods such as methods implemented by auto-zero executables 674 and/or calibration executables and data 676 that measure and make adjustments to what is referred to as the "dark current" or background noise of the photo detectors.

Components of scanner optics and detectors 100 placed in the optical path after elements such as attenuator 133 and/or shutter 134 may include dichroic beam splitter 136. Those of ordinary skill in the related art will appreciate that a dichroic beam splitter, also commonly referred to as a dichroic mirror, may include an optical element that is highly reflective to light of a certain wavelength range, and allow transmission of light through the beam splitter or mirror at one or more other wavelength ranges. Alternatively, the beam splitter or mirror may reflect a certain percentage of light at a particular wavelength and allow transmission of the remaining percentage. For example, dichroic beam splitter 136 may direct most of the excitation beam, illustrated as excitation beam 135', along an optical path towards objective lens 145 while allowing the small fractional portion of excitation beam 135 that is not reflected to pass through beam splitter 136, illustrated in FIG. 1 as partial excitation beam 137 For example, partial excitation beam 137 passes through dichroic beam splitter 136 to laser power monitor 110 for the purpose of measuring the power level of excitation beam 135 and providing feedback to scanner firmware executables 672. Firmware executables 672 may then makes adjustments, if necessary, to the power level via laser attenuator 133.

Detector 110 may be any of a variety of conventional devices for detecting partial excitation beam 137, such as a silicon detector for providing an electrical signal representative of detected light, a photodiode, a charge-coupled device, a photomultiplier tube, or any other detection device for providing a signal indicative of detected light that is now available or that may be developed in the future. As illustrated in FIG. 1, detector 110 generates excitation signal 194 that represents the detected signal from partial excitation beam 137. In accordance with known techniques, the amplitude, phase, or other characteristic of excitation signal 194 is designed to vary in a known or determinable fashion depending on the power of excitation beam 135. The term "power" in this context refers to the capability of beam 135 to evoke emissions. For example, the power of beam 135 typically may be measured in milliwatts of laser energy with respect to the illustrated example in which the laser energy evokes a fluorescent signal. Thus, excitation signal 194 has values that represent the power of beam 135 during particular times or time periods. Scanner firmware executables 672 may receive signal 194 for evaluation and, as described above, if necessary make adjustments.

After reflection from beam splitter 136, excitation beam 135' may continue along an optical path that is directed via periscope mirror 138, turning mirror 140, and arm end turning mirror 142 to objective lens 145. In the illustrated implementation mirrors 138, 140, and 142 may have the same reflective properties as turning mirrors 124, and could, in some implementations, be used interchangeably with turning mirrors 124. As described in greater detail below in relation to FIGS. 2A and 2B, lens 145 in the illustrated implementation is a small, light-weight lens located on the end of an arm that is driven by a galvanometer around an axis perpendicular to the plane represented by galvo rotation 149. In one embodiment, lens 145 focuses excitation beam 135' down to a specified spot size at the best plane of focus that could, for instance, include a 3.5 µm spot size. Galvo rotation 149 results in objective lens 145 moving in an arc over a substrate, illustrated in FIG. 2 as arcuate path 250 that may also be referred to herein as a "scanning line", upon which biological materials typically have been synthesized or have been deposited. Arcuate path 250 may, for instance, move in a 36 degree arc over a substrate. Fluorophores associated with these biological materials emit emission beam 152 at characteristic wavelengths in accordance with well-known principles. The term "fluorophore" commonly refers to a molecule that produces fluorescent light by energy transfer from light, chemical, or other types of energy sources.

Emission beam 152 in the illustrated example follows the reverse optical path as described with respect to excitation beam 135 until reaching dichroic beam splitter 136. In accordance with well known techniques and principles, the characteristics of beam splitter 136 are selected so that beam 152 (or a portion of it) passes through the mirror rather than being reflected. Emission beam 152 is then directed along a desired optical path to filter wheel 160.

In one embodiment, filter wheel 160 may be provided to filter out spectral components of emission beam 152 that are outside of the emission band of the fluorophore. The emission band is determined by the characteristic emission frequencies of those fluorophores that are responsive to the frequency of excitation beam 135. Thus, for example, excitation beam 135 from source 120, which is illustratively assumed to have a wavelength of 532 nanometers, excites certain fluorophores to a much greater degree than others. The characteristic emission wavelength of a first illustrative fluorophore (not shown in FIG. 1) when excited by beam 135 may be assumed to be 551 nanometers. Emission beam 152 in this example typically will also include wavelengths above and below 551 nanometers in accordance with distributions that are known to those of ordinary skill in the relevant art. The result may include filtered emission beam 154 that is a representation of emission beam 152 that has been filtered by a desired filter of filter wheel 160.

In some implementations filter wheel 160 is capable of holding a plurality of filters that each could be tuned to different wavelengths corresponding to the emission spectra from different fluorophores. Filter wheel 160 may include a mechanism for turning the wheel to position a desired filter in the optical path of emission beam 152. The mechanism may include a motor or some other device for turning that may be responsive to instructions from scanner firmware executables 672. For example, biological probe array experiments could be carried out on the same probe array where a plurality of fluorophores with different emission spectra are used that could be excited by a single or multiple lasers. Dyes that use the same excitation wavelengths but have differing emission spectral properties could be produced by methods such as those known to those in the art as fluorescent resonant energy transfer (FRET) where two fluorophores are present in the same molecule. The emission wavelength of one fluorophore overlaps the excitation wavelength of the second fluorophore and results in the emission of a wavelength from the second fluorophore that is atypical of the class of fluorophores that use that excitation wavelength. Thus by using one excitation beam it is possible to obtain distinctly different emissions so that different features of a probe array could be labeled in a single experiment.

In the present example the probe array could be scanned using a filter of one wavelength, then one or more additional scans could be performed that each correspond to a particular fluorophore and filter pair. Scanner control and analysis executables 572 could then process the data so that the user could be presented with a single image or other format for data analysis. In other implementations, multiple excitation sources 120 (or one or more adjustable-wavelength excitation sources) and corresponding multiple optical elements in optical paths similar to the illustrated one could be employed for simultaneous scans at multiple wavelengths. Other examples of scanner systems that utilize multiple emission wavelengths are described in U.S. patent application Ser. No. 09/683,216 titled "System, Method, and Product For Dynamic Noise Reduction in Scanning of Biological Materials", filed Dec. 3, 2001; U.S. patent application Ser. No. 09/683,217 titled "System, Method, and Product for Pixel Clocking in Scanning of Biological Materials", filed Dec. 3, 2001; and U.S. patent application Ser. No. 09/683,219 titled "System, Method, and Product for Symmetrical Filtering in Scanning of Biological Materials", filed Dec. 3, 2001 each of which are hereby incorporated by reference in their entireties for all purposes.

In accordance with techniques well known to those of ordinary skill in the relevant arts, including that of confocal microscopy, beam 154 may be focused by various optical elements such as lens 165 and passed through illustrative pinhole 167, aperture, or other element. In accordance with known techniques, pinhole 167 is positioned such that it rejects light from focal planes other than the plane of focus of objective lens 145 (i.e., out-of-focus light), and thus increases the resolution of resulting images. After passing through pinhole 167, the portion of filtered emission beam 154 that corresponds to the plane of focus, represented as filtered emission beam 154', continues along a desired optical path and impinges upon emission detector 115.

Similar to excitation detector 110, emission detector 115 may be a silicon detector for providing an electrical signal representative of detected light, or it may be a photodiode, a charge-coupled device, a photomultiplier tube, or any other detection device that is now available or that may be developed in the future for providing a signal indicative of detected light. Detector 115 generates emission signal 192 and/or calibration signal 196 that represents filtered emission beam 154' in the manner noted above with respect to the generation of excitation signal 194 by detector 110. Emission signal 192 and excitation signal 194 are provided to scanner firmware executables 672 for processing, as described below in relation to FIG. 5.

In the same or other implementations, one or more additional dichroic mirrors may be placed in the optical path of emission beam 152 represented in FIG. 1 as dichroic mirror 170. Each of the one or more mirrors 170 could be tuned to select specific wavelengths of emission beam 152 to reflect. The reflected beam of the selected wavelength is represented in FIG. 1 as selected emission beam 175. Selected emission beam 175 could, in some implementations, be directed to additional detection devices that may be the same type of detection device as emission detectors 110 or 115 represented as selected beam detection device 180. Device 180 may also be associated with implementations of the above described optical elements, such as filter wheel 160, lens 165, and pinhole 167. For example, biological probe array experiments could be carried out on the same probe array where a plurality of fluorophores with different emission spectra is used. Each of the fluorophores may have a distinct emission spectra that has an associated implementation of mirror 170 tuned to reflect the distinct emission spectra and allow all other spectra to pass through as previously described with respect to beam splitter 136. In the present example, each of mirrors 170 has an associated filter wheel 160, lens 165, and pinhole 167, as well as detector 180. Each of detectors 180 associated generates a signal similar to emission signal 192 that is specific to the detected spectra reflected by mirror 170. Each of signals 192 may then be forwarded to scanner firmware and additionally sent to scanner control an analysis executables for further processing. Additionally, in the present example a single scan may be performed where the fluorophores are excited by the excitation beam and the distinct emission spectra associated with the fluorophores could be selected for by dichroic mirrors 170, as opposed to the situation where a separate scan may need to be performed for each fluorophore using a single implementation of detector 115 and associated optical elements. Benefits from this configuration could include a reduced amount of what is referred to by those in the art as photobleaching. Photobleaching is a characteristic of fluorescent emissions according to which the amount of time that a fluorophore is exposed to the excitation light corresponds to a reduction in emission intensity until it is reduced to a value that may be zero. Additionally, the implementation described in the example may require less time to scan an array using multiple fluorophores because it performs a single scan as opposed to multiple scans.

A method for aligning the optical paths within scanner 400 such as, excitation beam 135 and emission beam 152 may include the use of a plurality of optical barriers. In a similar fashion as with respect to shutter 134, the plurality of optical barriers could be constructed of metal, plastic, or other appropriate material capable of blocking essentially all of the laser light beam. Each of the optical barriers may include a pinhole type aperture that allows for a beam of light to pass completely through the optical barrier, and where each of the pinhole type apertures is slightly larger than either of beams 135 or 152. Each pinhole type aperture may be located at a known position in the optical barrier such as, for instance, in the center of the optical barrier, although it is not necessary that the known position of the pinhole type aperture be the same position for each optical barrier. The method may include placing each optical barrier with associated pinhole type aperture in successive positions in the optimal desired optical path within scanner 400. In one embodiment of the method, the first step of aligning may include placing a first optical barrier with an associated pinhole type aperture in a fixed position close to laser 120, or alternatively close to a turning mirror, such as turning mirror 124. The pinhole type aperture must be placed in the optical path that the beam must travel through to be properly aligned. Adjustment of the optical path of the beam may be required if the beam does not pass through the pinhole type aperture. Adjustment may be accomplished either by adjusting the aim and/or position of laser 120, and/or adjustments to one or more turning mirrors may be made, until the beam passes through the pinhole type aperture. The method may be repeated with optical barriers being placed at successive positions within the optical path, where each successive position is farther away from laser 120 than the last position, until the entire optical path has been aligned. In the presently described method, the fixed positions may be located so that each optical barrier may be supported by some fixed, rigid structure within scanner 400. Additionally, the number of optical barriers may vary as needed by the complexity of the light path within the scanner.

Figure 2A:
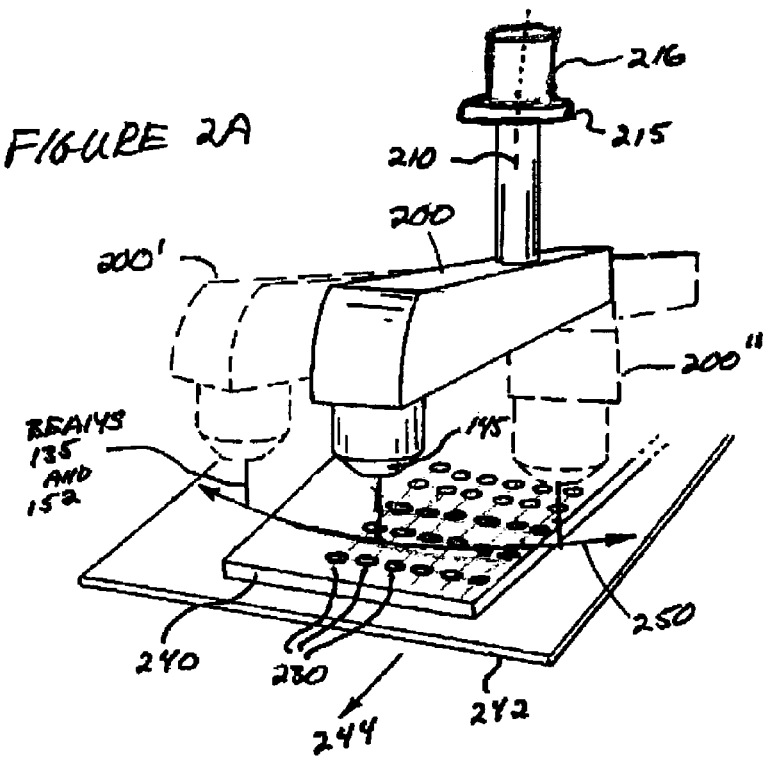
FIG. 2A is a perspective view of a simplified exemplary configuration of a scanning arm portion of the scanner optics and detectors of FIG. 1.

FIG. 2A illustrates an example of a perspective view of a simplified representation of a scanning arm portion of scanner optics 100 in accordance with this particular, non-limiting, implementation. Arm 200 moves in arcs around axis 210, which is perpendicular to the plane of galvo rotation 149. A position transducer may also be associated with arm 200. A possible benefit of this construction may be that the position of the oscillating arm itself is determined at each instant of data collection. Exact position data from the position transducer may be used for the construction of linearity correction tables and used for image correction methods that will be described in greater detail below in reference to calibration and image-correction methods. The position transducer, in accordance with any of a variety of known techniques, provides an electrical signal indicative of the radial position of arm 200. Certain non-limiting implementations of position transducers for galvanometer-driven scanners are described in U.S. Pat. No. 6,218,803 that is hereby incorporated by reference in its entirety for all purposes.

Figure 2B:
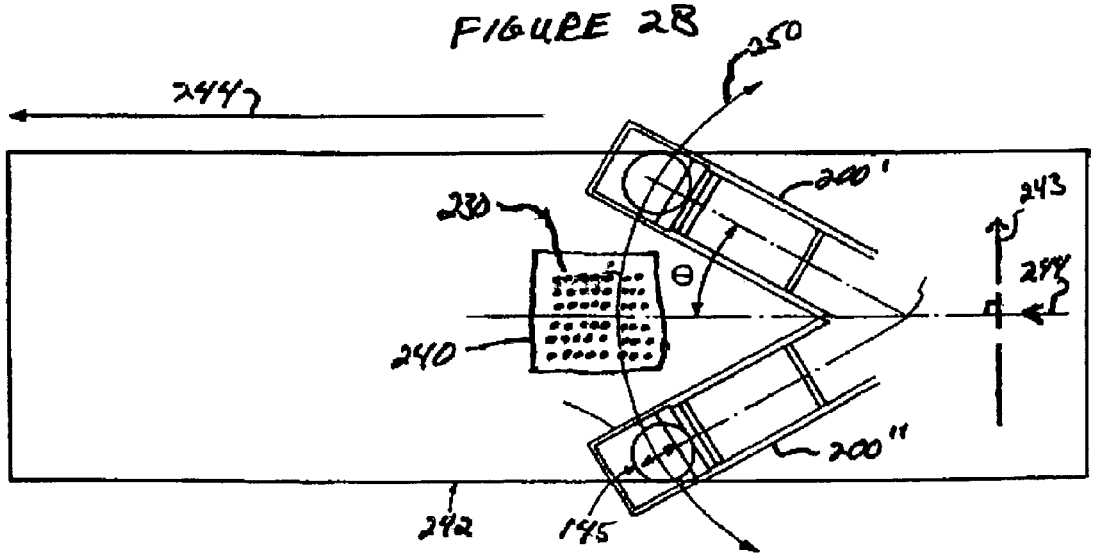
FIG. 2B is a top planar view of the scanning arm of FIG. 2A as it scans biological features on one embodiment of a probe array being moved by a translation stage under the arm's arcuate path.

Arm 200 is shown in alternative position 200' and 200" as it moves back and forth in scanning arcs about axis 210. Excitation beams 135 pass through objective lens 145 on the end of arm 200 and excite fluorophores that may be contained in hybridized probe-target pairs in features 230 on a substrate of probe array 240, as further described below. The arcuate path of excitation beams 135 over probe array 240 is schematically shown for illustrative purposes as path 250. Emission beams 152 pass up through objective lens 145 as noted above. Probe array 240 of this example is disposed on translation stage 242 that is moved in direction 244 so that arcuate path 250 repeatedly crosses the plane of probe array 240. The example of stage 242 is presented for the purposes of illustration only, and will be understood that other embodiments exist such as, for instance, one or more elements of cartridge transport frame 505 that will be discussed in detail below. As is evident, the resulting coverage of excitation beams 135 over the plane of probe array 240 in this implementation is therefore determined by the footprint of beam, the speed of movement in direction 244, and the speed of the scan. FIG. 2B is a top planar view of arm 200 with objective lens 145 scanning features 230 on probe array 240 as translation stage 242 is moved under path 250. As shown in FIG. 2B, arcuate path 250 of this example is such that arm 200 has a radial displacement of θ in each direction from an axis parallel to direction 244. For convenience of reference below, a direction 243 perpendicular to direction 244 is also shown in FIG. 2B. For illustrative purposes, direction 243 may hereafter be referred to herein as the "x" direction, and direction 244 as the "y" direction.

In this implementation, the scan arm moves through a constant arc regardless of the array being scanned. As a result, the lens traverses the same distance over the array, and accordingly, the same number of pixels, regardless of where over the array the lens is traveling or the fluorescent material that may be present in the array. In addition, the time it takes in this implementation for the lens to complete one pass and return back to a starting position is the same, for example in one possible implementation ⅕₀th of a second, regardless of the array being scanned or the fluorescent materials that may be present. Alternatively, some implementations may include the scan arm moving in an arc that is dependant upon the size of probe array 240. For example, the width of the arc for a particular probe array may be stored in scanner parameter data 677 that may be used by scanner firmware executables 672 to define the size of the arc.

Further details of confocal, galvanometer-driven, arcuate, laser scanning instruments suitable for detecting fluorescent emissions are provided in PCT Application PCT/US99/06097 (published as WO99/47964) and in U.S. Pat. Nos. 6,185,030; 6,201,639; and 6,225,625, all of which have been incorporated by reference above.

Probe Array 240: Various techniques and technologies may be used for synthesizing dense arrays of biological materials on or in a substrate or support. For example, Affymetrix GeneChip® arrays are synthesized in accordance with techniques sometimes referred to as VLSIPS™ (Very Large Scale Immobilized Polymer Synthesis) technologies. Some aspects of VLSIPS™ and other microarray and polymer (including protein) array manufacturing methods and techniques have been described in U.S. patent Ser. No. 09/536,841, International Publication No. WO 00/58516; U.S. Pat. Nos. 5,143, 854, 5,242,974, 5,252,743, 5,324,633, 5,445,934, 5,744,305, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846, 6,022,963, 6,083,697, 6,291,183, 6,309,831 and 6,428,752; and in PCT Applications Nos. PCT/US99/00730 (International Publication No. WO 99/36760) and PCT/US01/04285, which are all incorporated herein by reference in their entireties for all purposes.

Patents that describe synthesis techniques in specific embodiments include U.S. Pat. Nos. 6,486,287, 6,147,205, 6,262,216, 6,310,189, 5,889,165, 5,959,098, and 5,412,087, all hereby incorporated by reference in their entireties for all purposes. Nucleic acid arrays are described in many of the above patents, but the same techniques generally may be applied to polypeptide arrays or other types of probe arrays.

Generally speaking, an "array" typically includes a collection of molecules that can be prepared either synthetically or biosynthetically. The molecules in the array may be identical, they may be duplicative, and/or they may be different from each other. The array may assume a variety of formats, e.g., libraries of soluble molecules; libraries of compounds tethered to resin beads, silica chips, or other solid supports; and other formats.

The terms "solid support," "support," and "substrate" may in some contexts be used interchangeably and may refer to a material or group of materials having a rigid or semi-rigid surface or surfaces, which may be, or have coverings that are, porous or not and that may provide two or three dimensions for the securing of probes. In many embodiments, at least one surface of a solid support will be substantially flat, although in some embodiments it may be desirable to physically separate synthesis regions for different compounds with, for example, wells, raised regions, pins, etched trenches or wells, or other separation members or elements. In some embodiments, the solid support(s) may take the form of beads, resins, gels, microspheres, or other materials and/or geometric configurations.

Generally speaking, a "probe" typically is a molecule that can be recognized by a particular target. To ensure proper interpretation of the term "probe" as used herein, it is noted that contradictory conventions exist in the relevant literature. The word "probe" is used in some contexts to refer not to the biological material that is synthesized on a substrate or deposited on a slide, as described above, but to what is referred to herein as the "target."

A target is a molecule that has an affinity for a given probe. Targets may be naturally-occurring or man-made molecules. Also, they can be employed in their unaltered state or as aggregates with other species. The samples or targets are processed so that, typically, they are spatially associated with certain probes in the probe array. For example, one or more tagged targets may be distributed over the probe array.

Targets may be attached, covalently or noncovalently, to a binding member, either directly or via a specific binding substance. Examples of targets that can be employed in accordance with this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term target is used herein, no difference in meaning is intended. Typically, a "probe-target pair" is formed when two macromolecules have combined through molecular recognition to form a complex.

The probes of the arrays in some implementations comprise nucleic acids that are synthesized by methods including the steps of activating regions of a substrate and then contacting the substrate with a selected monomer solution. The term "monomer" generally refers to any member of a set of molecules that can be joined together to form an oligomer or polymer. The set of monomers useful in the present invention includes, but is not restricted to, for the example of (poly) peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer. The term "monomer" also refers to a chemical subunit that can be combined with a different chemical subunit to form a compound larger than either subunit alone. In addition, the terms "biopolymer" and "biological polymer" generally refer to repeating units of biological or chemical moieties. Representative biopolymers include, but are not limited to, nucleic acids, oligonucleotides, amino acids, proteins, peptides, hormones, oligosaccharides, lipids, glycolipids, lipopolysaccharides, phospholipids, synthetic analogues of the foregoing, including, but not limited to, inverted nucleotides, peptide nucleic acids, Meta-DNA, and combinations of the above. "Biopolymer synthesis" is intended to encompass the synthetic production, both organic and inorganic, of a biopolymer. Related to the term "biopolymer" is the term "biomonomer" that generally refers to a single unit of biopolymer, or a single unit that is not part of a biopolymer. Thus, for example, a nucleotide is a biomonomer within an oligonucleotide biopolymer, and an amino acid is a biomonomer within a protein or peptide biopolymer; avidin, biotin, antibodies, antibody fragments, etc., for example, are also biomonomers.

As used herein, nucleic acids may include any polymer or oligomer of nucleosides or nucleotides (polynucleotides or oligonucleotides) that include pyrimidine and/or purine bases, preferably cytosine, thymine, and uracil, and adenine and guanine, respectively. An "oligonucleotide" or "polynucleotide" is a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA), which may be isolated from natural sources, recombinantly produced or artificially synthesized and mimetics thereof. A further example of a polynucleotide in accordance with the present invention may be peptide nucleic acid (PNA) in which the constituent bases are joined by peptides bonds rather than phosphodiester linkage, as described in Nielsen et al., *Science* 254:1497-1500 (1991); Nielsen, *Curr. Opin. Biotechnol.*, 10:71-75 (1999), both of which are hereby incorporated by reference herein. The invention also encompasses situations in which there is a nontraditional base pairing such as Hoogsteen base pairing that has been identified in certain tRNA molecules and postulated to exist in a triple helix. "Polynucleotide" and "oligonucleotide" may be used interchangeably in this application.

Additionally, nucleic acids according to the present invention may include any polymer or oligomer of pyrimidine and purine bases, preferably cytosine (C), thymine (T), and uracil (U), and adenine (A) and guanine (G), respectively. See Albert L. Lehninger, PRINCIPLES OF BIOCHEMISTRY, at 793-800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be deoxyribonucleic acid (DNA) or ribonucleic acid (RNA), or a mixture thereof, and may exist permanently or transitionally in single-stranded or double-stranded form, including homoduplex, heteroduplex, and hybrid states.

As noted, a nucleic acid library or array typically is an intentionally created collection of nucleic acids that can be prepared either synthetically or biosynthetically in a variety of different formats (e.g., libraries of soluble molecules; and libraries of oligonucleotides tethered to resin beads, silica chips, or other solid supports). Additionally, the term "array" is meant to include those libraries of nucleic acids that can be prepared by spotting nucleic acids of essentially any length (e.g., from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleotide sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired. Nucleic acid arrays that are useful in the present invention include those that are commercially available from Affymetrix, Inc. of Santa Clara, Calif., under the registered trademark "GeneChip®." Example arrays are shown on the website at affymetrix.com.

In some embodiments, a probe may be surface immobilized. Examples of probes that can be investigated in accordance with this invention include, but are not restricted to, agonists and antagonists for cell membrane receptors, toxins and venoms, viral epitopes, hormones (e.g., opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies. As non-limiting examples, a probe may refer to a nucleic acid, such as an oligonucleotide, capable of binding to a target nucleic acid of complementary sequence through one or more types of chemical bonds, usually through complementary base pairing, usually through hydrogen bond formation. A probe may include natural (i.e. A, G, U, C, or T) or modified bases (7-deazaguanosine, inosine, etc.). In addition, the bases in probes may be joined by a linkage other than a phosphodiester bond, so long as the bond does not interfere with hybridization. Thus, probes may be peptide nucleic acids in which the constituent bases are joined by peptide bonds rather than phosphodiester linkages. Other examples of probes include antibodies used to detect peptides or other molecules, or any ligands for detecting its binding partners. Probes of other biological materials, such as peptides or polysaccharides as non-limiting examples, may also be formed. For more details regarding possible implementations, see U.S. Pat. No. 6,156,501, hereby incorporated by reference herein in its entirety for all purposes. When referring to targets or probes as nucleic acids, it should be understood that these are illustrative embodiments that are not to limit the invention in any way.

Furthermore, to avoid confusion, the term "probe" is used broadly herein to refer, for example, to probes such as those synthesized according to the VLSIPS™ technology; the biological materials deposited so as to create spotted arrays; and materials synthesized, deposited, or positioned to form arrays according to other current or future technologies. Thus, microarrays formed in accordance with any of these technologies may be referred to generally and collectively hereafter for convenience as "probe arrays." Moreover, the term "probe" is not limited to probes immobilized in array format. Rather, the functions and methods described herein may also be employed with respect to other parallel assay devices. For example, these functions and methods may be applied with respect to probe-set identifiers that identify probes immobilized on or in beads, optical fibers, or other substrates or media.

In accordance with some implementations, some targets hybridize with probes and remain at the probe locations, while non-hybridized targets are washed away. These hybridized targets, with their tags or labels, are thus spatially associated with the probes. The term "hybridization" refers to the process in which two single-stranded polynucleotides bind non-covalently to form a stable double-stranded polynucleotide. The term "hybridization" may also refer to triple-stranded hybridization, which is theoretically possible. The resulting (usually) double-stranded polynucleotide is a "hybrid." The proportion of the population of polynucleotides that forms stable hybrids is referred to herein as the "degree of hybridization." Hybridization probes usually are nucleic acids (such as oligonucleotides) capable of binding in a base-specific manner to a complementary strand of nucleic acid. Such probes include peptide nucleic acids, as described in Nielsen et al., Science 254:1497-1500 (1991) or Nielsen Curr. Opin. Biotechnol., 10:71-75 (1999) (both of which are hereby incorporated herein by reference), and other nucleic acid analogs and nucleic acid mimetics. The hybridized probe and target may sometimes be referred to as a probe-target pair. Detection of these pairs can serve a variety of purposes, such as to determine whether a target nucleic acid has a nucleotide sequence identical to or different from a specific reference sequence. See, for example, U.S. Pat. No. 5,837,832, referred to and incorporated above. Other uses include gene expression monitoring and evaluation (see, e.g., U.S. Pat. No. 5,800,992 to Fodor, et al.; U.S. Pat. No. 6,040,138 to Lockhart, et al.; and International App. No. PCT/US98/15151, published as WO99/05323, to Balaban, et al.), genotyping (U.S. Pat. No. 5,856,092 to Dale, et al.), or other detection of nucleic acids. The '992, '138, and '092 patents, and publication WO99/05323, are incorporated by reference herein in their entireties for all purposes.

The present invention also contemplates signal detection of hybridization between probes and targets in certain embodiments. See U.S. Pat. Nos. 5,143,854; 5,578,832; 5,631,734; 5,936,324; 5,981,956; 6,025,601 incorporated above, and U.S. Pat. Nos. 5,834,758, 6,141,096; 6,185,030; 6,201,639; 6,218,803; and 6,225,625, U.S. Patent application 60/364,731, and PCT Application PCT/US99/06097 (published as WO99/47964), each of which also is hereby incorporated by reference in its entirety for all purposes.

A system and method for efficiently synthesizing probe arrays using masks is described in U.S. patent application Ser. No. 09/824,931, filed Apr. 3, 2001, that is hereby incorporated by reference herein in its entirety for all purposes. A system and method for a rapid and flexible microarray manufacturing and online ordering system is described in U.S. patent application, Ser. No. 10/065,868 filed Nov. 26, 2002, that also is hereby incorporated herein by reference in its entirety for all purposes. Systems and methods for optical photolithography without masks are described in U.S. Pat. No. 6,271,957 and in U.S. patent application Ser. No. 09/683,374 filed Dec. 19, 2001, both of which are hereby incorporated by reference herein in their entireties for all purposes.

As noted, various techniques exist for depositing probes on a substrate or support. For example, "spotted arrays" are commercially fabricated, typically on microscope slides. These arrays consist of liquid spots containing biological material of potentially varying compositions and concentrations. For instance, a spot in the array may include a few strands of short oligonucleotides in a water solution, or it may include a high concentration of long strands of complex proteins. The Affymetrix® 417™ Arrayer and 427™ Arrayer are devices that deposit densely packed arrays of biological materials on microscope slides in accordance with these techniques. Aspects of these and other spot arrayers are described in U.S. Pat. Nos. 6,040,193 and 6,136,269 and in PCT Application No. PCT/US99/00730 (International Publication Number WO 99/36760) incorporated above and in U.S. patent application Ser. No. 09/683,298 hereby incorporated by reference in its entirety for all purposes. Other techniques for generating spotted arrays also exist. For example, U.S. Pat. No. 6,040,193 to Winkler, et al. is directed to processes for dispensing drops to generate spotted arrays. The '193 patent, and U.S. Pat. No. 5,885,837 to Winkler, also describe the use of micro-channels or micro-grooves on a substrate, or on a block placed on a substrate, to synthesize arrays of biological materials. These patents further describe separating reactive regions of a substrate from each other by inert regions and spotting on the reactive regions. The '193 and '837 patents are hereby incorporated by reference in their entireties. Another technique is based on ejecting jets of biological material to form a spotted array. Other implementations of the jetting technique may use devices such as syringes or piezo electric pumps to propel the biological material. It will be understood that the foregoing are non-limiting examples of techniques for synthesizing, depositing, or positioning biological material onto or within a substrate. For example, although a planar array surface is desirable in some implementations of the foregoing, a probe array may be fabricated on a surface, or in a three-dimensional space, of virtually any shape or even a multiplicity of shapes and/or surfaces. Arrays may comprise probes synthesized or deposited on beads, fibers such as fiber optics, glass, silicon, silica or any other appropriate substrate, see U.S. Pat. No. 5,800,992 referred to and incorporated above and U.S. Pat. Nos. 5,770,358, 5,789,162, 5,708,153 and 6,361,947 all of which are hereby incorporated in their entireties for all purposes. Arrays may be packaged in such a manner as to allow for diagnostics or other manipulation in an all inclusive device, see for example, U.S. Pat. Nos. 5,856,174 and 5,922,591 hereby incorporated in their entireties by reference for all purposes.

Probes typically are able to detect the expression of corresponding genes or EST's by detecting the presence or abundance of mRNA transcripts present in the target. This detection may, in turn, be accomplished in some implementations by detecting labeled cRNA that is derived from cDNA derived from the mRNA in the target.

The terms "mRNA" and "mRNA transcripts" as used herein, include, but not limited to pre-mRNA transcript(s), transcript processing intermediates, mature mRNA(s) ready for translation and transcripts of the gene or genes, or nucleic acids derived from the mRNA transcript(s). Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

In general, a group of probes, sometimes referred to as a probe set, contains sub-sequences in unique regions of the transcripts and does not correspond to a full gene sequence. Further details regarding the design and use of probes and probe sets are provided in PCT Application Serial No. PCT/US 01/02316, filed Jan. 24, 2001 incorporated above; and in U.S. Pat. No. 6,188,783 and in U.S. patent applications Ser. No. 09/721,042, filed on Nov. 21, 2000, Ser. No. 09/718,295, filed on Nov. 21, 2000, Ser. No. 09/745,965, filed on Dec. 21, 2000, and Ser. No. 09/764,324, filed on Jan. 16, 2001, all of which patent and patent applications are hereby incorporated herein by reference in their entireties for all purposes.

Figure 3:
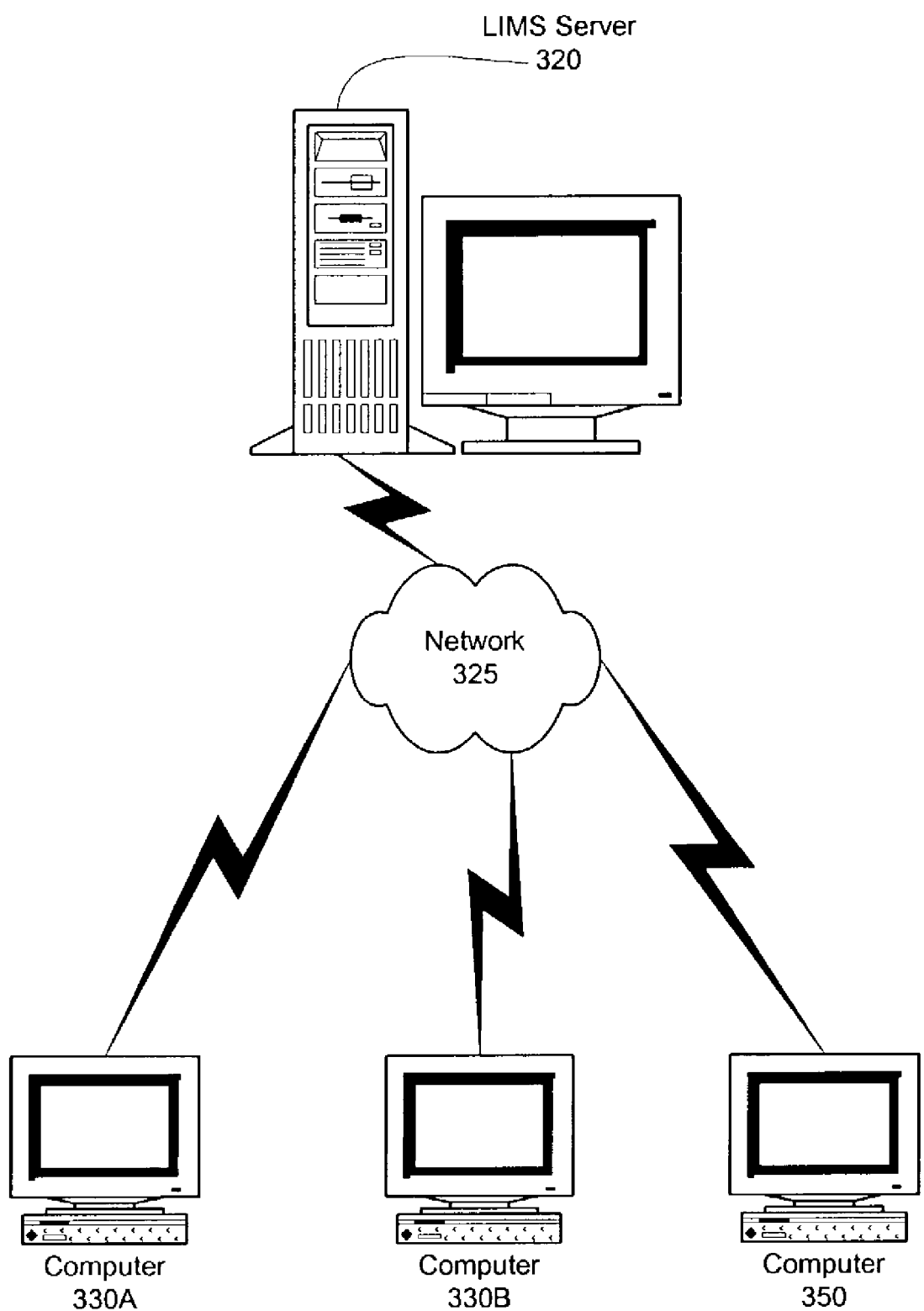
FIG. 3 is a functional block diagram of one embodiment of a computer network system including user computers coupled to a server suitable for execution of information management, and array-image-acquisition and analysis, software applications in accordance with one embodiment of the present invention.
Figure 4:
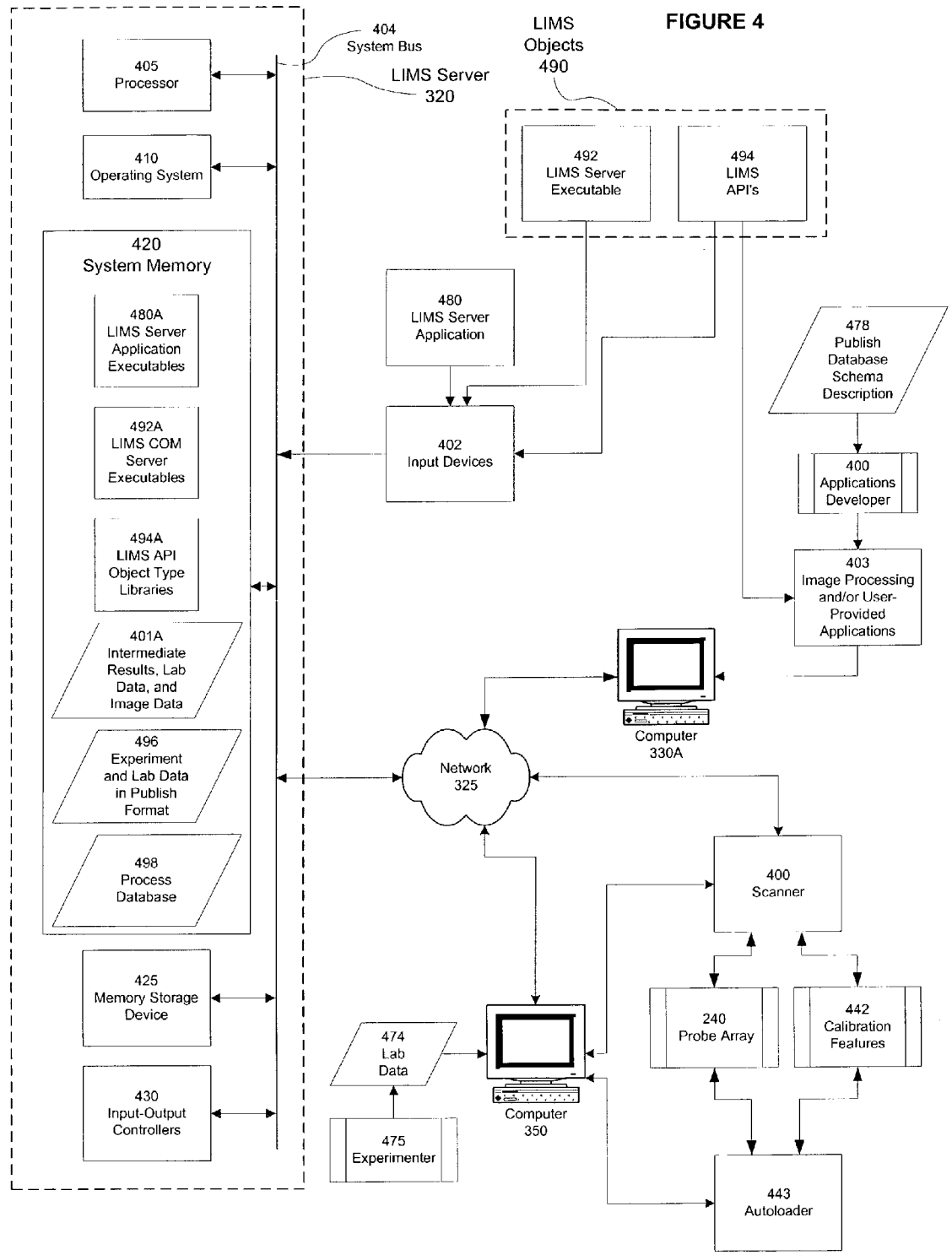
FIG. 4 is a functional block diagram of the server of FIG. 3 including illustrative embodiments of the software application, auto-loader, scanner, and connections to user computers.

LIMS Server 320: FIGS. 3 and 4 show a typical configuration of a server computer connected to a workstation computer via a network. For convenience, the server computer is referred to herein as LIMS server 320, although this computer may carry out a variety of functions in addition to those described below with respect to the implementations of Affymetrix® LIMS, Affymetrix® AIMS, Affymetrix® GDAC, and Affymetrix® LIMS-SDK software applications. Moreover, in some implementations any function ascribed to LIMS server 320 may be carried out by one or more other computers, and/or the functions may be performed in parallel by a group of computers. Network 325 may include a local area network, a wide area network, the Internet, another network, or any combination thereof.

An illustrative embodiment of LIMS server 320 is shown in greater detail in FIG. 4. Typically, LIMS server 320 is a network-server class of computer designed for servicing a number of workstations or other computer platforms over a network. However, server 320 may be any of a variety of types of general-purpose computers such as a personal computer, workstation, main frame computer, or other computer platform now or later developed. Server 320 typically includes known components such as a processor 405, an operating system 410, a system memory 420, memory storage devices 425, and input-output controllers 430. It will be understood by those skilled in the relevant art that there are many possible configurations of the components of server 320 and that some components that may typically be included are not shown, such as cache memory, a data backup unit, and many other devices. Similarly, many hardware and associated software or firmware components that may be implemented in a network server are not shown in FIG. 4. For example, components to implement one or more firewalls to protect data and applications, uninterruptible power supplies, LAN switches, web-server routing software, and many other components are not shown. Those of ordinary skill in the art will readily appreciate how these and other conventional components may be implemented.

Processor 405 may include multiple processors; e.g., multiple Intel Xeon® 700 MHz processors. As further examples, processor 405 may include one or more of a variety of other commercially available processors such as Pentium® processors from Intel, SPARC® processors made by Sun Microsystems, or other processors that are or will become available. Processor 405 executes operating system 410, which may be, for example, a Windows®-type operating system (such as Windows® 2000 with SP 1, Windows NT® 4.0 with SP6a) from the Microsoft Corporation; the Solaris operating system from Sun Microsystems, the Tru64 Unix from Compaq, other Unix® or Linux-type operating systems available from many vendors; another or a future operating system; or some combination thereof. Operating system 410 interfaces with firmware, such as scanner firmware 510, and hardware in a well-known manner. Operating system 410 also facilitates processor 405 in coordinating and executing the functions of various computer programs that may be written in a variety of programming languages. Operating system 410, typically in cooperation with processor 405, coordinates and executes functions of the other components of server 320. Operating system 410 also provides scheduling, input-output control, file and data management, memory management, and communication control and related services, all in accordance with known techniques.

System memory 420 may be any of a variety of known or future memory storage devices. Examples include any commonly available random access memory (RAM), magnetic medium such as a resident hard disk or tape, an optical medium such as a read and write compact disc, or other memory storage device. Memory storage device 425 may be any of a variety of known or future devices, including a compact disk drive, a tape drive, a removable hard disk drive, or a diskette drive. Such types of memory storage device 425 typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory 420 and/or the program storage device used in conjunction with memory storage device 425.

In some embodiments, a computer program product is described comprising a computer usable medium having control logic (computer software program, including program code) stored therein. The control logic, when executed by processor 405, causes processor 405 to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers 430 could include any of a variety of known devices for accepting and processing information from a user, whether a human or a machine, whether local or remote. Such devices include, for example, modem cards, network interface cards, sound cards, or other types of controllers for any of a variety of known input or output devices. In the illustrated embodiment, the functional elements of server 320 communicate with each other via system bus 404. Some of these communications may be accomplished in alternative embodiments using network or other types of remote communications.

Figure 12:
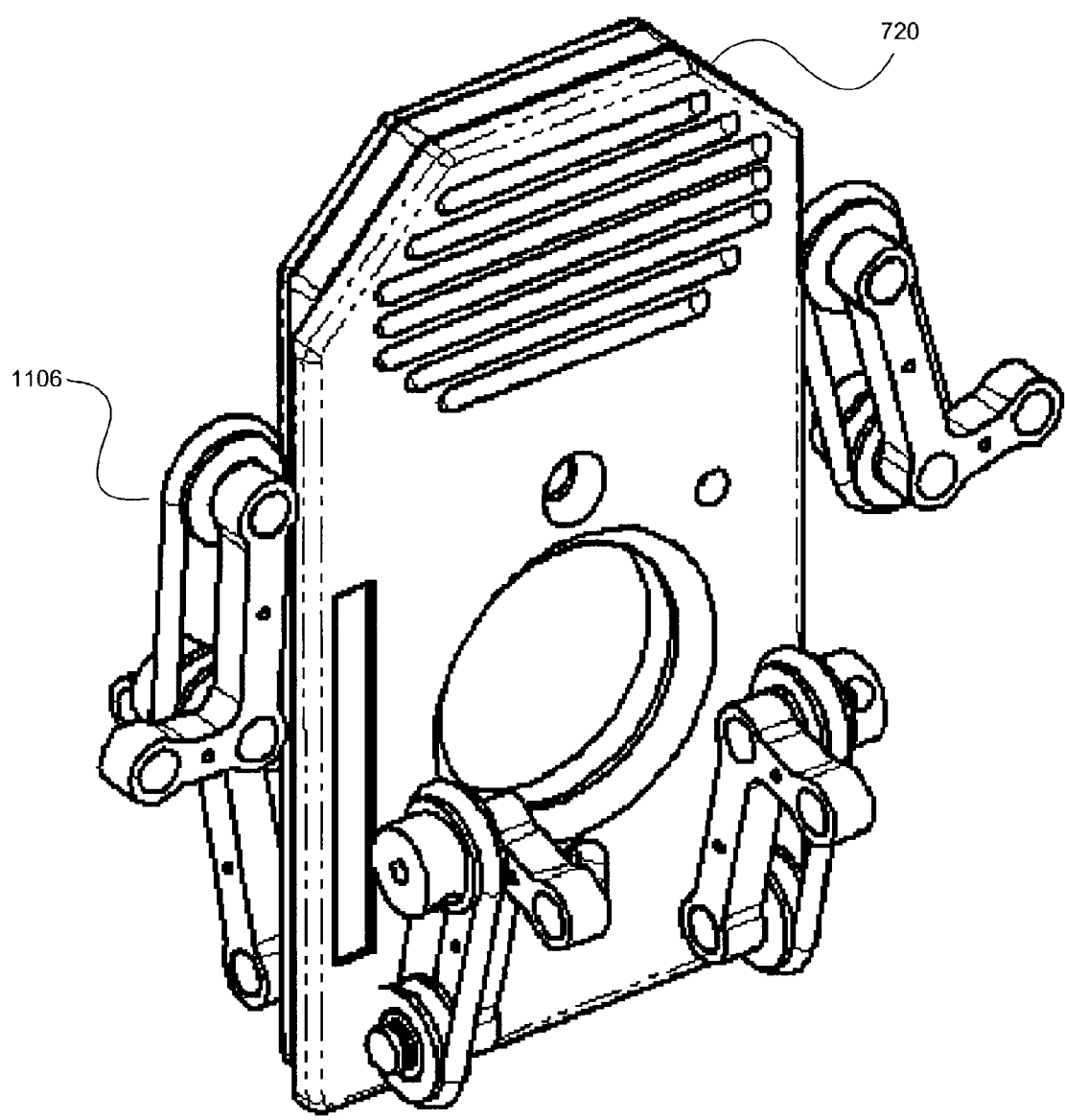
FIG. 12 is a graphical representation of one embodiment of a probe array cartridge and the reversible rollers of FIG. 11.

As will be evident to those skilled in the relevant art, LIMS server application 480, as well as LIMS Objects 490 including LIMS servers 492 and LIMS API's 494 (described below), if implemented in software, may be loaded into system memory 420 and/or memory storage device 425 through one of input devices 402. LIMS server application 480 as loaded into system memory 420 is shown in FIG. 12 as LIMS server application executables 480A. Similarly, objects 490 are shown as LIMS server executables 492A and LIMS API object type libraries 494A after they have been loaded into system memory 420. All or portions of these loaded elements may also reside in a read-only memory or similar device of memory storage device 425, such devices not requiring that the elements first be loaded through input devices 402. It will be understood by those skilled in the relevant art that any of the loaded elements, or portions of them, may be loaded by processor 405 in a known manner into system memory 420, or cache memory (not shown), or both, as advantageous for execution.

LIMS Server Application 480: Details regarding the operations of illustrative implementations of application 480 are provided in U.S. patent applications Ser. Nos. 09/682,098; 10/219,882; and 10/370,442 (entitled System and Method for Programmatic Access to Biological Probe Array Data, filed Feb. 19, 2003), each of which is hereby incorporated by reference herein in its entirety for all purposes. It will be understood that the particular LIMS implementation described in this patent application is illustrative only, and that many other implementations may be used with LIMS objects 490 and other aspects of the present or alternative embodiments.

Application 480, and other software applications referred to herein, may be implemented using Microsoft® Visual C++ or any of a variety of other programming languages. For example, applications may also be written in Java, C++, Visual Basic, any other high-level or low-level programming language, or any combination thereof. As noted, certain implementations may be illustrated herein with respect to a particular, non-limiting, implementation of application 480, one implementation of application 480 is Affymetrix® LIMS. Full database functionality is intended to provide a data streaming solution and a single infrastructure to manage information from probe array experiments. Application 480 provides the functionality of database storage and retrieval system for accessing and manipulating all system data. A database server provides an automated and integrated data management environment for the end user. All process data, raw data and derived data may be stored as elements of the database, providing an alternative to a file-based storage mechanism. A database back end may also provide integration of application 480 into a customer's overall information system infrastructure. Data typically is accessible through standard interfaces and can be tracked, queried, archived, exported, imported and administered.

Application 480 of the illustrated implementation supports process tracking for a generic assay; adds enhanced administration functionality for managing synthesized probe arrays, spotted probe arrays, and data from these or other types of probe arrays that typically are published to a database schema standard such as Affymetrix' AADM standard; provides a full Oracle® database management software or SQL Server solution; supports publishing of genotype and sequence data; and provides a high level of security for the LIMS system.

In particular, application 480 of the illustrated example provides processes for enabling sample definition, experiment setup, hybridization, scanning, grid alignment, cell intensity analysis, probe array analysis, publishing, and a variety of other functions related to experimental design and implementation. Application 480 supports multiple experiments per sample definition via a re-queuing process, multiple hybridization and scan operations for a single experiment, data re-analysis, and publishing to more than one database. The process database, which may be implemented either as an Oracle or SQL Server database management system in the illustrated implementation, typically is supported by a COM communication layer to the process database. A gene-information database may also be provided to store chromosome and probe sequence information about the biological item on the probe array, and related information. Another feature, as noted, is publication of data in accordance with a database schema that typically is made public to enable third-party access and software interface development. For example, the AADM database schema provides for publication of Affymetrix® GeneChip® data with support for either an Oracle or SQL server database management system. Among other structures, tables are provided in the AADM implementation that provide support for genotype data.

In particular implementations, a LIMS security database implements a role-based security level that is integrated with Windows NT® user authentication security. The security database supports role definition, functional access within a role, and assignment of NT groups and users to those roles. A role is a collection of users who have a common set of access rights to probe array data. In an illustrative implementation, roles may be defined per server/database, and a role member may be a member of multiple roles. The software determines a user's access rights based on predetermined rules governing such rights as a function of role or other variable. A function is a pre-determined action that is common to all roles. Each role is defined by the functions it can and cannot perform. Functions explicitly describe the type of action that a member of the role can perform. The functions supported by a newly created role include, but are not limited to, read process data, delete process data, update process data, archive process data, assume ownership of process data, import process data, export process data, delete AADM data, create a AADM database, and maintaining roles. When a new user is added to a role, they typically have access privileges for their data and read only access privilege for other user data within the same role. All non-role members are denied all access privileges to role member's data. When application 480 of the illustrated implementation is installed, at least two roles are created: administration and system user. The installer of the system software is added as a user to the administration role and a selected Windows NT® group is added as a user to the system user role.

In accordance with some implementations, a stand-alone application may be provided to enable user management capabilities. These capabilities include but are not limited to the following: AADM database creation, publish data deletion, process data deletion, taking ownership of process data, archiving and de-archiving of process data, data export, data import, role management, filter based find, managing expression analysis parameter sets, and managing sample and experiment attribution templates. Further details are provided in U.S. patent application Ser. No. 09/682,098, incorporated by reference above.

LIMS Objects 490: In the illustrated implementation, LIMS Objects 490 is an object oriented programmers interface into LIMS server application 480. In the illustrated embodiment, LIMS objects 490 includes a number of Application Programmers Interfaces (APIs), generally and collectively represented as LIMS API's 494, and a number of LIMS servers, generally and collectively represented as LIMS servers 492. LIMS servers 492 may be distributed as out of process executables ("exe's") and LIMS API's 494 may be distributed as object type libraries ("tlb's"). Those of ordinary skill in the art will appreciate that various other distribution schemes and arrangements are possible in other implementations.

LIMS Objects 490 typically may be used by an application developer (represented in FIG. 4 as applications developer 400) who wishes to integrate in-house or third-party software systems with a LIMS such as LIMS server application 480. For example, it is illustratively assumed that applications developer 400 works in an enterprise that employs LIMS server application 480 to manage data related to experiments conducted on probe arrays, which may include any type of probe arrays such as GeneChip® probe arrays or spotted arrays (illustratively represented in FIGS. 2 and 4 as probe array 240). It further is assumed for illustrative purposes that LIMS server application 480 is not a full-service system in that it does not provide functions such as laboratory process scheduling, sample management, instrument control, batch processing, and/or various data mining, processing, or visualization functions. Alternatively, application 480 may provide some or all of these functions, but applications developer 400 may wish to develop alternative or supplementary software applications to perform all or portions of any of these or other functions, and/or to integrate third-party software applications for these purposes. LIMS objects 490 provides developer 400 with tools to customize both the input of data into, and output of data from, LIMS server application 480.

LIMS objects 490 includes LIMS API's 494. API's 494, in the particular implementation of LIMS COM API's, includes the following classes: loading list of objects, reading an object, updating/writing an object, deleting an object, processing data, creating AADM-compliant databases, and invoking the analysis controller. API's are also included for objects, which are used by the previously listed classes.

Some implementations may include, as one of many possible examples of data schemes, the AADM database schema. This particular implementation may be divided for illustrative purposes into four sub-schemas: chip design, experiment setup, analysis results, and protocol parameters. The chip design sub-schema contains the overall chip description including the name, number of rows and columns of cells, the number of units, and a description of the units. The experiment setup sub-schema contains information on the chip used and the target that was applied. The analysis results sub-schema stores the results from expression analyses. The protocol parameters sub-schema contains parameter information relating to target preparation, experiment setup, and chip analysis. The AADM database can be queried for analysis results, protocol parameters, and experiment setup. Similar queries are enabled by Affymetrix® Data Mining Tool software, described in U.S. patent application, Ser. No. 09/683,980, which is hereby incorporated herein by reference in its entirety for all purposes. The Affymetrix Data Mining Tool also uses a supplementary database called the Data Mining Info database, which stores user preferences, saved queries, frequently asked queries, and probe set lists. The Gene Info database, used by Affymetrix Microarray Suite, stores probe set information such as descriptions of probe sets, sequences that are tiled on an expression array, and user defined annotations. This database also stores lists of external database links that allow users to add links to internal/external databases, which could be public or private. The SPT, or "spot" file, contains the results of the image quantification and CSV information integrated together.

Computer 350: User computer 350, shown in FIGS. 3, 4, and 5, may be a computing device specially designed and configured to support and execute some or all of the functions of scanner control and analysis executables 572. Computer 350 also may be any of a variety of types of general-purpose computers such as a personal computer, network server, workstation, or other computer platform now or later developed. Computer 350 typically includes known components such as a processor 555, an operating system 560, a system memory 570, memory storage devices 581, and input-output controllers 575. It will be understood by those skilled in the relevant art that there are many possible configurations of the components of computer 350 and that some components that may typically be included in computer 350 are not shown, such as cache memory, a data backup unit, and many other devices. Processor 555 may be a commercially available processor such as a Pentium® processor made by Intel Corporation, a SPARC® processor made by Sun Microsystems, or it may be one of other processors that are or will become available. Processor 555 executes operating system 560, which may be, for example, a Windows®-type operating system (such as Windows NT® 4.0 with SP6a) from the Microsoft Corporation; a Unix® or Linux-type operating system available from many vendors; another or a future operating system; or some combination thereof. Operating system 560 interfaces with firmware and hardware in a well-known manner, and facilitates processor 555 in coordinating and executing the functions of various computer programs that may be written in a variety of programming languages. Operating system 560, typically in cooperation with processor 555, coordinates and executes functions of the other components of computer 350. Operating system 560 also provides scheduling, input-output control, file and data management, memory management, and communication control and related services, all in accordance with known techniques.

System memory 570 may be any of a variety of known or future memory storage devices. Examples include any commonly available random access memory (RAM), magnetic medium such as a resident hard disk or tape, an optical medium such as a read and write compact disc, or other memory storage device. Memory storage device 581 may be any of a variety of known or future devices, including a compact disk drive, a tape drive, a removable hard disk drive, or a diskette drive. Such types of memory storage device 581 typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory 570 and/or the program storage device used in conjunction with memory storage device 581.

In some embodiments, a computer program product is described comprising a computer usable medium having control logic (computer software program, including program code) stored therein. The control logic, when executed by processor 555, causes processor 555 to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers 575 could include any of a variety of known devices for accepting and processing information from a user, whether a human or a machine, whether local or remote. Such devices include, for example, modem cards, network interface cards, sound cards, or other types of controllers for any of a variety of known input devices. Output controllers of input-output controllers 575 could include controllers for any of a variety of known display devices for presenting information to a user, whether a human or a machine, whether local or remote. If one of the display devices provides visual information, this information typically may be logically and/or physically organized as an array of picture elements, sometimes referred to as pixels. A Graphical user interface (GUI) controller may comprise any of a variety of known or future software programs for providing graphical input and output interfaces between computer 350 and a user, and for processing user inputs. In the illustrated embodiment, the functional elements of computer 350 communicate with each other via system bus 590. Some of these communications may be accomplished in alternative embodiments using network or other types of remote communications.

As will be evident to those skilled in the relevant art, executables 572, if implemented in software, may be loaded into system memory 570 and/or memory storage device 581 through one of the input devices. All or portions of executables 572 may also reside in a read-only memory or similar device of memory storage device 581, such devices not requiring that executables 572 first be loaded through the input devices. It will be understood by those skilled in the relevant art that executables 572, or portions of it, may be loaded by processor 555 in a known manner into system memory 570, or cache memory (not shown), or both, as advantageous for execution.

Scanner Computer 510: Scanner 510 may include elements such as processor 655, operating system 660, input-output controllers 575, system memory 670, memory storage devices 681, and system bus 690 that may, in some implementations, have the same characteristics of corresponding elements in computer 350. Other elements of scanner computer 510 may include scanner firmware executables 672, auto-focus/auto-zero executables 674, calibration executables and data 676, and scanner parameter data 677 that will each be described in detail below.

Figure 5:
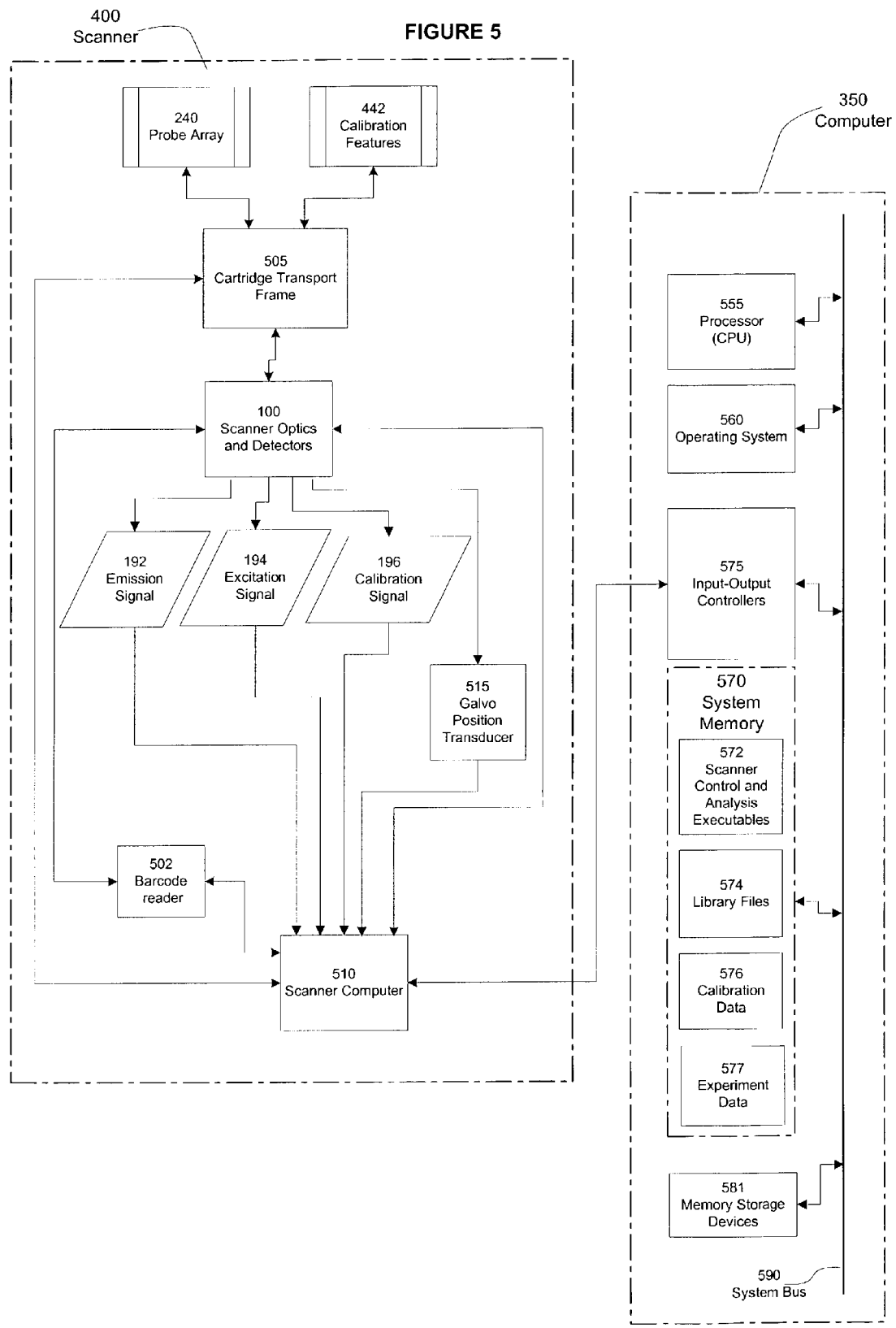
FIG. 5 is a functional block diagram of one embodiment of the scanner-computer system of FIG. 4 including a barcode reader, a cartridge transport frame, a scanner computer, and scanner control operations.

Scanner firmware executables 672 may, in many implementations, be enabled to control all functions of scanner 400 based, at least in part, upon data stored locally in scanner parameter data 677 or remotely in one or more data files from one or more remote sources. For example as illustrated in FIG. 5, the remote data source could include computer 350 that includes library files 574, calibration data 576, and experiment data 577 stored in system memory 570. In the present example, the flow of data to scanner computer 510 may be managed by scanner control and analysis executables 572 that may be responsive to data requests from firmware executables 672.

A possible advantage of including scanner computer 510 in a particular implementation is that scanner 400 may be network based and/or otherwise arranged so that a user computer, such as computer 350, is not required. Input-output controllers 675 may include what is commonly referred to by those of ordinary skill in the related art as a TCP/IP network connection. The term "TCP/IP" generally refers to a set of protocols that enable the connection of a number of different networks into a network of networks (i.e. the Internet). Scanner computer 510 may use the network connection to connect to one or more computers, such as computer 350, in place of a traditional configuration that includes a "hardwire" connection between a scanner instrument and a single computer. For example, the network connection of input-output controllers 675 may allow for scanner 400 and one more computers to be located remotely from one another. Additionally, a plurality of users, each with their own computer, may utilize scanner 400 independently. It some implementations it is desirable that only a single computer is allowed to connect to scanner 400 at a time. Alternatively, a single computer may interact with a plurality of scanners. In the present example, all calibration and instrument specific information may be stored in one or more locations in scanner computer 510 that may be made available to the one or more computers as they interface with scanner computer 510.

The network based implementation of scanner 400 described above may include methods that enable scanner 400 to operate unimpaired during averse situations that, for instance, may include network disconnects, heavy network loading, electrical interference with the network connection, or other types of adverse event. In some implementations, scanner 400 may require a periodic signal from computer 350 to indicate that the connection is intact. If scanner 400 does not receive that signal within an expected period of time, scanner 400 may operate on the assumption that the network connection has been lost and start storing data that would have been transmitted. When the network connection has been reacquired to scanner 400, all collected data and related information may be transferred to computer 350 that would have normally been transferred if the network connection remained intact. For example, during the occurrence of an adverse situation scanner 400 may lose the network connection to computer 350. The methods enable scanner 400 to operate normally including the acquisition of image data and other operations without interruption. Scanner 400 may store the acquired image data of at least one complete scanned image in memory storage devices 681 to insure that the data is not lost.

In some embodiments, scanner computer 510 may also enable scanner 400 to be configured as a standalone instrument that does not depend upon a controlling workstation. Scanner computer 510 may acquire and store image data as well as function as a data server to multiple clients for efficient data transfer. For example, scanner 400 may include a hard disk or other type of mass storage medium that may be enabled to hold large volumes of image, calibration, and scanner parameter data. Scanner 400 may additionally include barcode reader 502 that reads one or more barcode identifiers from barcode label 1500. Scanner computer 510 may execute the scan operations based, at least in part, upon one or more data files associated with the barcode identifiers, and store the acquired image data on the hard disk. Additionally, scanner 400 may provide a network file system or FTP service enabling one or more remote computers to query and upload scanned images as well as providing an interface enabling the computer to query scanner data and statistics.

It will be understood by those of ordinary skill in the related art that the operations of scanner computer 510 may be performed by a variety of other servers or computers, such as for instance computer 350 or LIMS server 320, or that computer 510 may not necessarily reside in scanner 400.

Barcode reader 502: FIG. 5 is a functional block diagram of a simplified example of a scanner-computer system showing scanner 400 under the control of computer 350. An element of scanner 400 may include barcode reader 502 that, among other things, is capable of reading or scanning a barcode that uniquely identifies probe array 240 when it is loaded into scanner 400 either manually or from auto-loader 443. In some implementations, barcode reader 502 may be located within scanner 400 and disposed so that it reads one or more barcodes associated with probe array 240 when the array is loaded into the scanner. Alternative embodiments may include an external location of barcode reader 502 that could, for instance, include a portable and/or hand-held version that a user could employ to manually scan a variety of barcodes. Each of the one or more barcodes may contain one or more barcode identifiers. Each of the barcode identifiers read by reader 502 may be used by scanner firmware 672 and/or by scanner control and analysis executables 572, a particular implementation of which is illustrated at times herein by reference to Affymetrix® MicroArray Suite software or Affymetrix® GeneChip® Operating System. The barcode identifiers may be used to correlate probe array 240 to scanner parameter data 677, experiment data 577 created by the experimenter, and/or one or more library files 574 or other data. Library files 574 may, in certain implementations, contain information including, but not limited to probe array type, lot, expiration date, and scanning parameters that could include the size of the probe array, feature size, chrome border dimensions, one or more excitation/emission wavelengths, or other data. Library files 574 may be received by computer 350 from a variety of sources including one or more remote sources via network 325 that could include an internet web portal such as, for example, the Affymetrix.com web portal provided by Affymetrix, Inc.

A barcode, as is known to those of ordinary skill in the relevant art, represents characters by combinations of bars and spaces and may be represented in a one or multi dimensional format each having a variety of possible symbologies. The term "symbology" generally refers to a bar code symbol that includes a pattern of bars and spaces that follow specific standards. A multi-dimensional barcode has the advantage of being able to store a greater capacity of information than a one-dimensional format. For example, one format for use with probe arrays may include a widely used two-dimensional barcode format. The two-dimensional barcode format may include a symbology that is well supported and may also have built-in error detection. Additionally, a two-dimensional format may be capable of achieving a sufficient symbology density to accommodate the amount of information associated with a probe array, and furthermore have sufficient built in redundancy to make the probability of a false read negligible. Other type of media may also be used to store machine-readable information at a higher capacity than that typically available using one-dimensional barcodes, such as magnetic strips and other magnetic or non-magnetic media known to those of ordinary skill in the relevant arts. Although the use of barcodes is described herein with respect to illustrative implementations, it will be understood that various alternative media, symbology, and techniques may be employed in alternative implementations.

Figure 15:
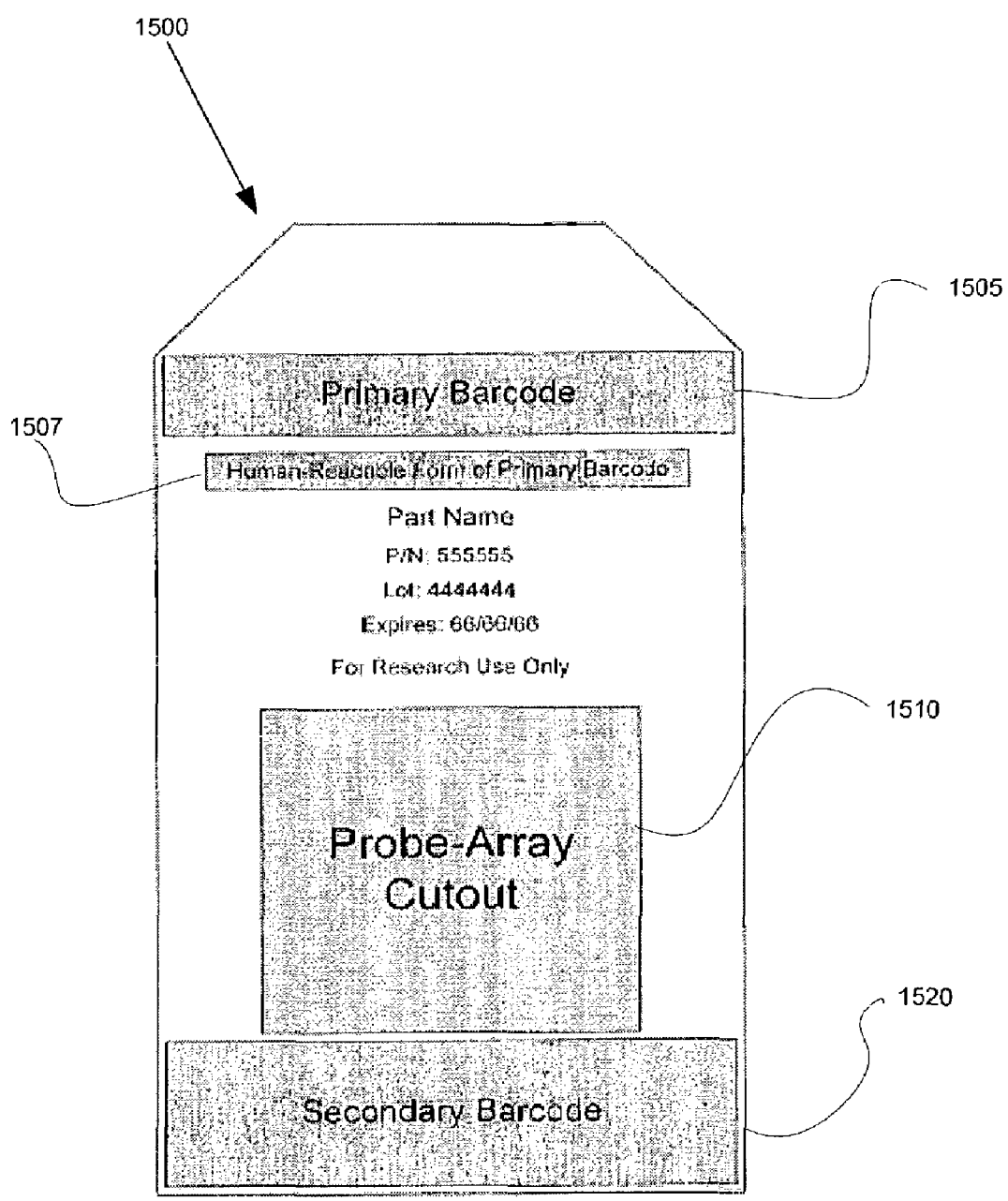
FIG. 15 is a graphical representation of one embodiment of a barcode label including a primary and secondary barcode.

An illustrative example of a label that contains barcode information is presented in FIG. 15. Barcode label 1500 may be made of a variety of materials and affixed to the probe array cartridge 720 (illustrated in FIG. 7) by a variety of methods. In the presently described example, the label may be constructed of white polyester, and affixed to the probe array cartridge with a permanent acrylic or other appropriate adhesive. Additionally, label 1500 may be constructed so that it demonstrates a resistance to aging, temperature extremes, and moisture to insure that the label remain in place and the integrity of the data is maintained for extended periods of time as well as to endure the conditions of probe array processing and data acquisition.

In one embodiment, barcode label 1500 may be positioned so that it is centered in a label pocket located on the front face of probe array cartridge 720. Label 1500 may in one implementation conform to the shape of the pocket that could, for instance, include a rectangular outer border with two adjacent corners on a short side cut off symmetrically at 45 degree angles. Label 1500 may also have one or more areas of material removed from within the area defined by the outside boundary, such as probe-array cutout 1510, to accommodate associated raised, depressed, or other type of features on probe array cartridge 720. It will be appreciated by those of ordinary skill in the art that many different positions and shapes of label 1500 are possible, and that the examples presented are for illustration only and should not be limiting in any way.

Barcode label 1500 may have a variety of possible features that could include primary barcode 1505, human readable form of primary barcode 1507, probe array cutout 1510, and secondary barcode 1520. In one implementation, the primary barcode may include information encoded in barcode symbology such as manufacturer identification, part number, design identification number, expiration date, lot number, and sequence number (e.g., a number that is incremented by one each time a label is printed). Barcode 1505 may also include other information possibly relating to experimental data such as experiment number or other information defined by the user for experimental purposes. In some embodiments secondary barcode 1520 may be present and may include information encoded in barcode symbology relating to various parameters for scanning the probe array, e.g., the size or location of the area to be scanned, the types of labels that will be emitting radiation from the scanned array, the type or intensity of excitation beam to use in scanning the array, the speed at which to scan or the length of time to dwell on the features, and so on. Those of ordinary skill in the related art will appreciate that information encoded in barcodes 1507 and 1520 are not restricted to the examples presented here and should not be limiting in any way. Probe-array cutout 1510 may represent a part of the label that is removed, as described above, so that the probe array is not obscured by the label. Human readable form of primary barcode 1507 may contain one or more data elements from primary barcode 1505 and/or secondary barcode 1520 so that a user may understand and use the data elements such as, for instance to manually enter the one or more data elements. For example, one embodiment may include a raised feature on probe array cartridge 720 that surrounds the location of the probe array. Probe-array cutout 1510, in this example, may be slightly larger than the area of the raised feature and of similar shape, so that the label may be affixed to the probe array cartridge with the raised feature protruding through the label.

Other features that may be included in barcode label 1500 include what are commonly referred to by those of ordinary skill in the relevant art as quiet zones. The term "quiet zone" generally refers to an area around a barcode that has the same color and reflectivity as the spaces within the barcode. The quiet zone enables the barcode reader to detect the boundaries of the barcode and individual elements of the barcode symbology. A quiet zone may be any of a variety of widths, and may be considered to be a component a barcode symbology. Those of ordinary skill in the art will appreciate that the features of the quiet zones need not be the same for the primary and secondary barcodes.

It will be understood by those of ordinary skill in the relevant art that many possible methods exist for incorporating barcode information onto a cartridge or other types of packaging. For example a barcode could be printed directly onto a cartridge, or alternatively be manufactured as part of the cartridge itself, or as part of the array either incorporated into probes, into or on the substrate, and so on. Other systems and methods of barcode readers are also possible. One such example is described in U.S. patent application Ser. No. 10/063,284, entitled "SYSTEM AND METHOD FOR SCANNING OF BIOLOGICAL MATERIAL USING BARCODED INFORMATION," filed Apr. 8, 2002 that is incorporated by reference herein in its entirety for all purposes.

Cartridge Transport frame 505: Another element of scanner 400 includes cartridge transport frame 505 that provides all of the degrees of freedom required to manipulate probe array 240 or calibration features 442 for the purposes of auto-focus, scanning, and calibration. Those of ordinary skill in the related art will appreciate that the term "degrees of freedom" generally refers to the number of independent parameters required to specify the position and orientation of an object. Illustrated in FIG. 7 is an example of probe array cartridge 720 that, in one embodiment, houses probe array 240 or calibration features 442. In one embodiment, transport frame 505 is capable of manipulating the cartridge in four of six possible degrees of freedom (roll 700, pitch 703, Z 705 and Y 707). In the illustrated embodiment, it generally is not necessary to manipulate cartridge 720 for yaw 715 and X 717.

Figure 16:
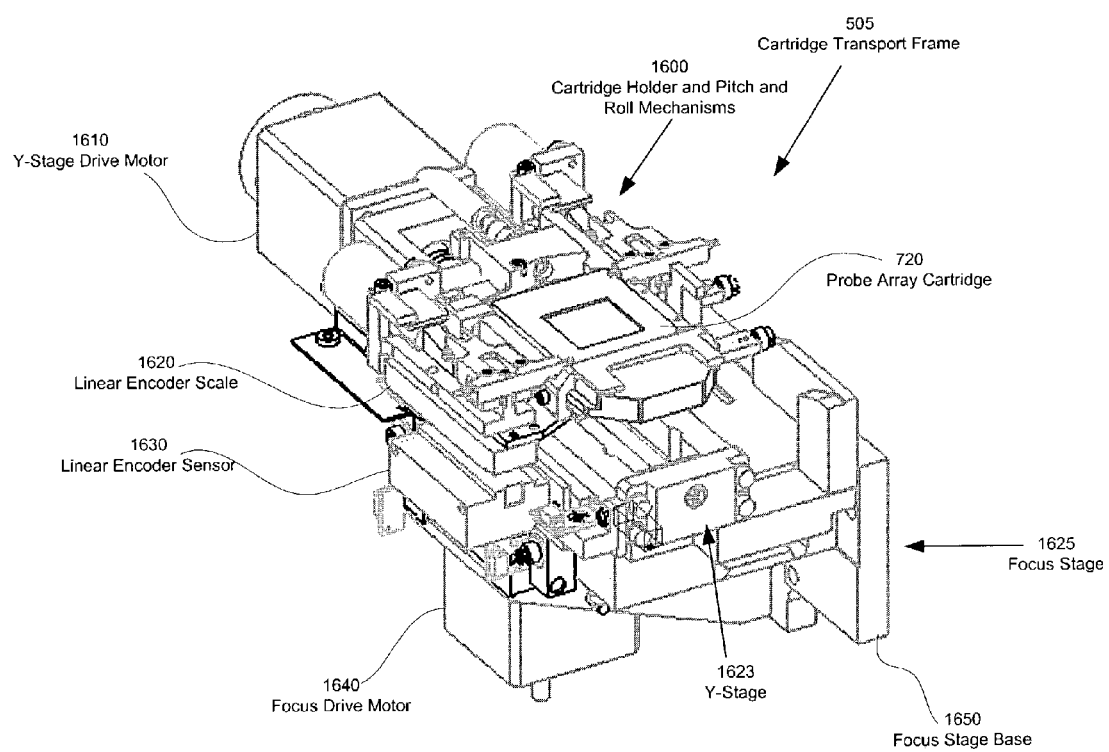
FIG. 16 is a graphical representation of one embodiment of the cartridge transport frame of FIG. 5 that includes a cartridge holder, pitch and roll mechanisms, Y-stage, and a focus stage.

Further examples of cartridge transport frame 505 are illustrated in FIGS. 16-19. FIG. 16 illustrates an example of the entire cartridge transport frame that is comprised of several elements. The main elements include cartridge holder and pitch and roll mechanisms 1600, Y-stage 1623, and Focus stage 1625. Elements of transport frame 505 may be constructed of a variety of materials that unless otherwise stated may, for instance, include A6061 T6 aluminum, alloy or other type of metal with similar properties. Each of the main elements will be described in detail below.

Figure 17:
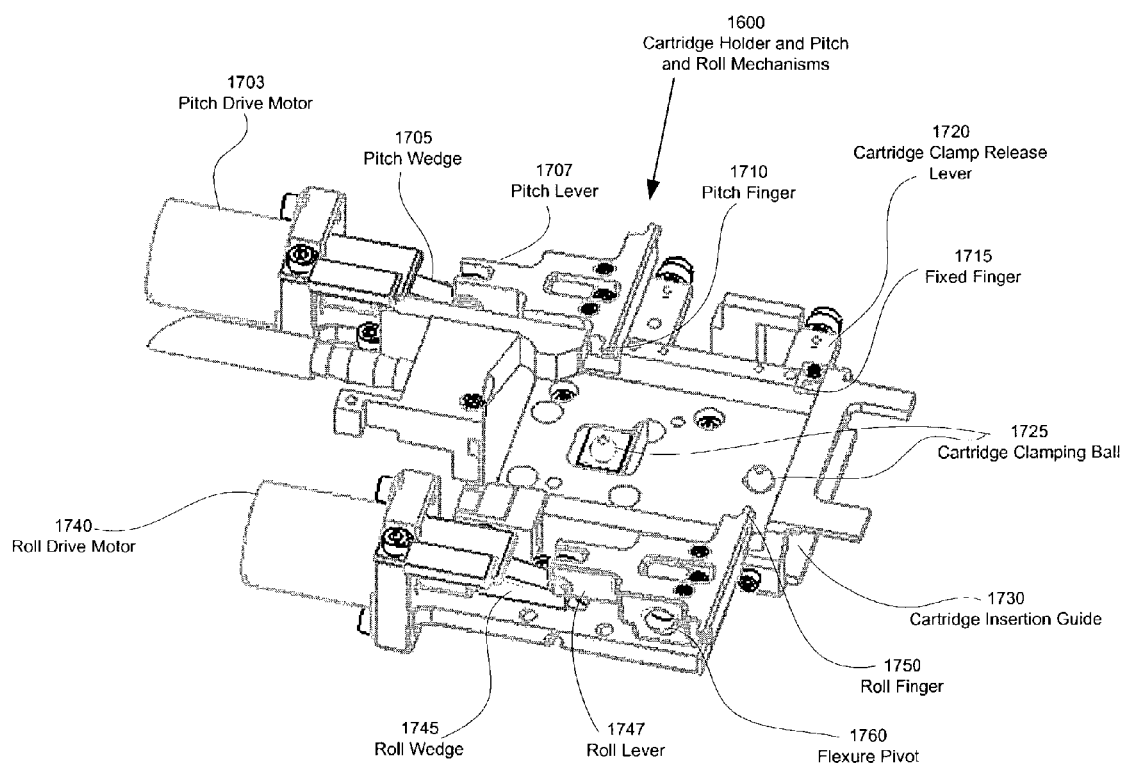
FIG. 17 is a graphical representation of one embodiment of the cartridge holder and pitch and roll mechanisms of FIG. 16 including a pitch finger and a roll finger.

An example of cartridge holder and pitch and roll mechanisms 1600 is further illustrated in FIG. 17. Probe array cartridge 720 is slidably inserted via cartridge insertion guide 1730 into holder 1600. An optical switch may be included that is activated when probe array cartridge 720 is inserted into the holder 1600. The optical switch may signal scanner firmware executables 672 when probe array cartridge 720 has been inserted. Upon receiving a cartridge present signal, firmware executables 672 may send instructions to engage cartridge clamping balls 1725 by actuation of cartridge clamp release lever 1720. Cartridge clamping balls 1725 may engage conical depressions located on the rear surface (i.e. side opposite the probe array 240) of probe array cartridge 720 and may employ leaf springs to apply some degree of pressure to apply and maintain the integrity of the engagement. The leaf springs may be made from a variety of materials including 400 series full hard stainless steel, or other type of full hardened steel. The pressure applied by the leaf springs via clamping balls 1725 acts to press cartridge 720 up against pitch finger 1710, fixed finger 1715, and roll finger 1750, thereby holding cartridge in place and enabling control of cartridge position as will be described below with respect to roll and pitch. A possible advantage may include making positional adjustments to bring all of the features of probe array 240 housed in probe array cartridge 720 into focus by manipulating the position of probe array cartridge 720 without changing the positions of other hardware elements such as the mechanical elements of cartridge holder and pitch and roll mechanisms 1600. After scanning or calibrations have been completed, firmware executables 672 may send instructions to disengage cartridge 720 by actuation of lever 1720 to reversibly retract clamping balls 1725 employing a lever cam mechanism driven by one or more motors, or alternatively by the movement of Y-stage 1623. Once released by clamping balls 1725, cartridge 720 may be removed from holder 1600 manually or by elements of auto-loader 443 such as reversible rollers 1106 as will be described in detail below.

As described in the example above, three fingers may support and mechanically reference the front surface of (i.e. side where probe array 240 or calibration feature 442 may be viewed and/or scanned) probe array cartridge 720. With a probe array cartridge engaged in holder 1600, fixed finger 1715 may be located at the upper left corner of probe array cartridge 720, pitch finger 1710 at the lower left corner, and roll finger 1750 at the upper right corner. Each of fingers 1710, 1715, and 1750 may be arranged orthoganally with respect to one another. In one implementation, pitch finger 1710 and roll finger 1750 are moveable via their associated pitch and roll mechanisms respectively. The pitch and roll mechanisms may be implemented as linear step-motor driven wedge-levers. As illustrated in the example of FIG. 17, the pitch mechanism includes pitch drive motor 1703, pitch wedge 1705, pitch lever 1707, and pitch finger 1710, and the roll mechanism is similarly constructed with elements 1740, 1745, 1747, and 1750. In the presently described embodiment, pitch 703 and roll 700 may be adjusted in order to bring all of the features of probe array 240 or calibration features 442 into the same plane with respect to the axis of rotation of galvo rotation 149, galvo arm 200, and objective lens 145. For example, one possible implementation of step-motor driven wedge-levers may yield at least a twelve to one reduction in the magnitude of the input stroke from motors 1703 or 1740. The reduction in magnitude provides the capability to make very accurate micro adjustments to the position of cartridge 720 in the pitch 703 and roll 700 axes respectively. In the present example, very small roll 700 and pitch 703 adjustments may be necessary to bring all of the features contained on probe array 240 or calibrations features 442 into the same plane of focus. Further details of roll and pitch adjustment are described below with respect to auto-focus/auto-zero executables 674.

Figure 19:
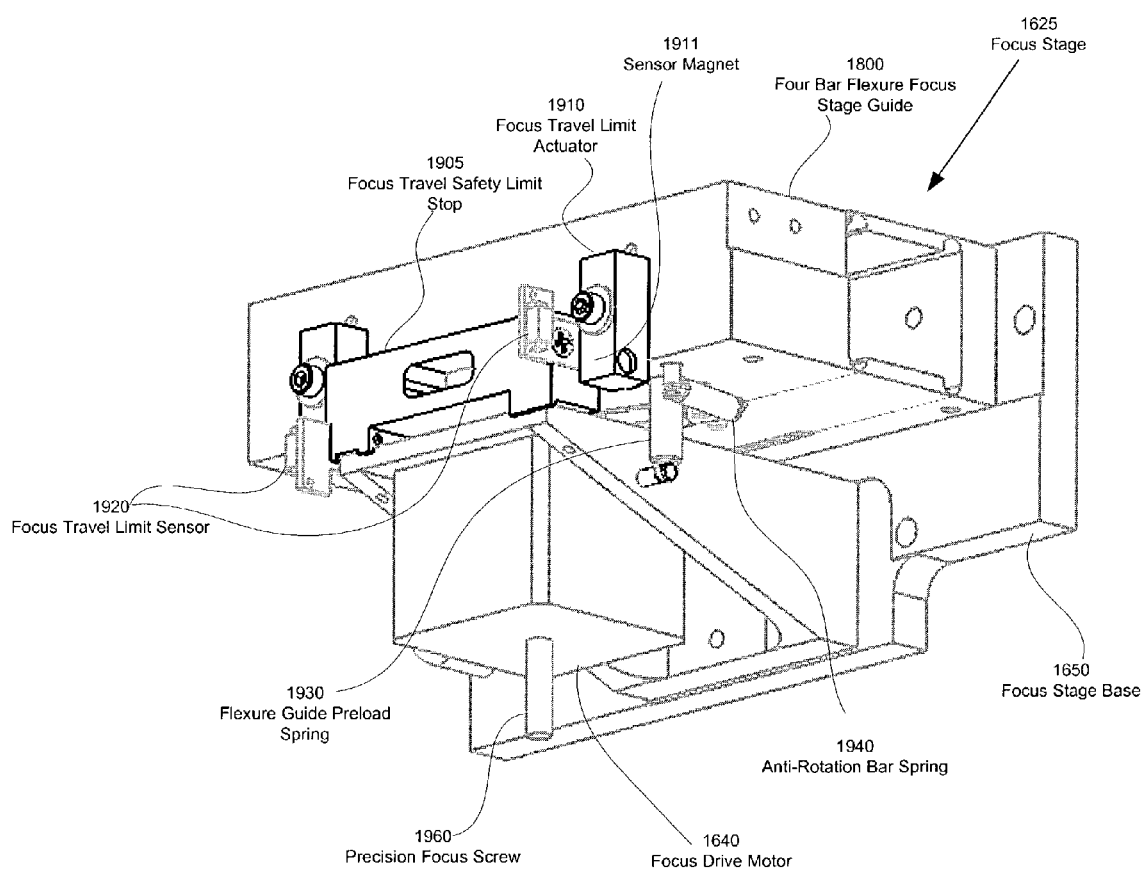
FIG. 19 is a graphical representation of one embodiment of the four-bar flexure focus stage guide of FIG. 18 assembled as a component of the focus stage of FIG. 16.

Probe array 240 or calibration features 442 may be brought into best focus by adjusting the distance of probe array 240 or calibration features 442 from objective lens 145. In some implementations, the distance adjustment may be employed by moving the position of focus stage 1625 in the Z 705 axis. As illustrated in FIG. 19, Z 705 motion may be achieved, under the control of scanner firmware executables 672, by rotation of precision focus screw 1960 driven by focus drive motor 1640. Focus Screw 1960 may be coupled to a solid hinge four bar flexure focus stage guide 1800 via a free floating nut. In one embodiment, guide 1800 is capable of motion transverse to the plane of best focus while maintaining the orientation of the probe array with respect to the pitch 703 and roll 700 axes. The maintenance of the orientation may be aided further by one or more anti-rotation bar springs 1940 that may apply a measure of force to guide 1800 if guide 1800 moves in a rotational axis with respect to the Z 705 axis. For example, the free floating nut may include an anchor bar that is attached to spring 1940. The other side of spring 1940 may be attached to a fixed stop positioned on guide 1800, where spring 1940 applies pressure against rotational movement of guide 1800 but allows movement in a desired axis. Alternatively, the maintenance of the orientation may be aided by a stabilizing anchor arm such as, for instance, the anchor bar of the floating nut that is caused to engage a fixed pin by spring 1940.

In one possible implementation, focus screw 1960 acts upon Y-stage 1623 to push it in a first direction opposed to a force applied by a plurality of flexure guide preload springs 1930. The movement may be accomplished by focus drive motor 1640 rotating screw 1960 threaded to the free floating nut. As will be appreciated by those of ordinary skill in the related art, rotating screw 1960 in a first direction results in the free floating nut moving an a first direction, such as for instance in a direction opposite the force applied by springs 1930. In some implementations, it may not be desirable that screw 1960 and the free floating nut interact directly with Y-stage 1623 and/or guide 1800. Various implementations may include an intermediate element such as, for instance, a ball-shaped element that may have the advantage of allowing for proper interaction when the components are not positioned at right angles with respect to one another. The ball-shaped element may be constructed of hardened steel or other similar material. Y-stage 1623 may also be reversibly moved in the opposite direction to the first direction by reversing the rotation of focus screw 1960 where the movement of Y-stage 1623 may be aided by the force applied by the plurality of springs 1930. For example, Y-stage 1623 may be attached to the top of moving load carrier 1820 via bolts, screws, or other method commonly used by those in the art, thus load carrier 1820 moves with Y-stage 1623 in the Z 705 axis as one unit.

Figure 18:
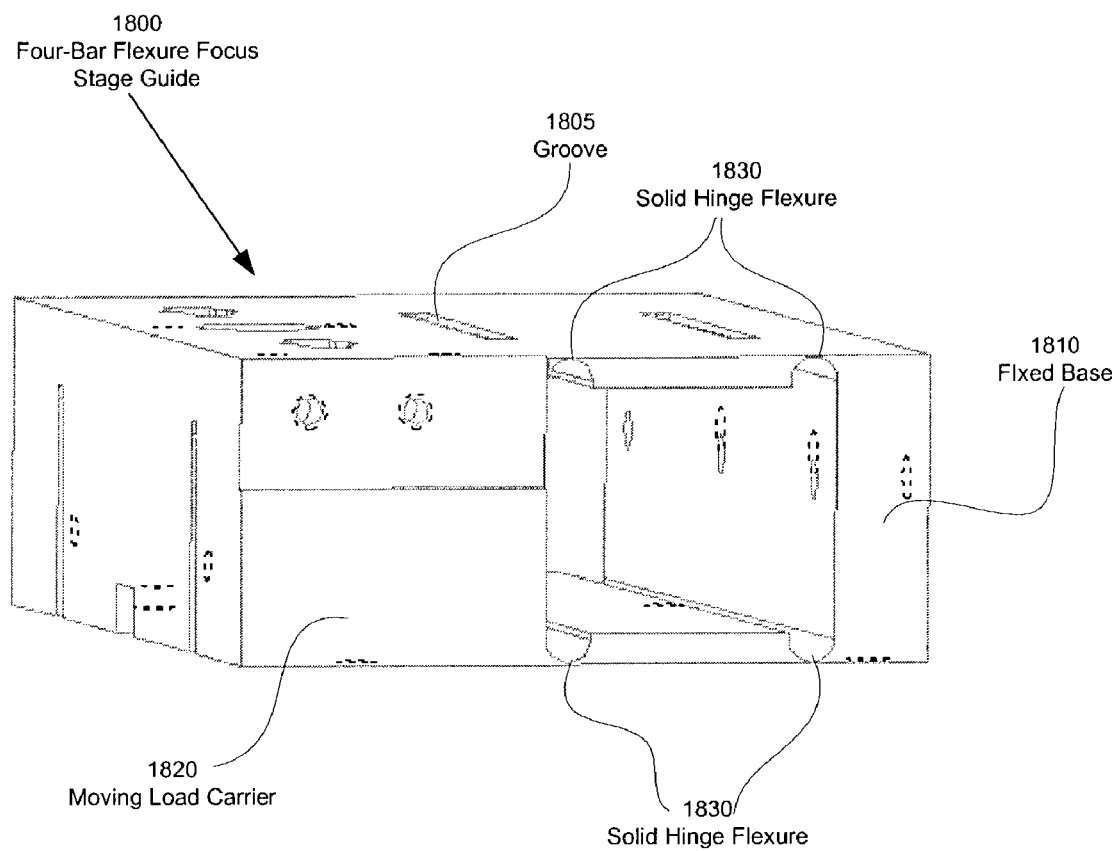
FIG. 18 is a graphical representation of one embodiment of a four-bar flexure focus stage guide.

Other elements of an illustrative embodiment of four bar flexure focus stage guide 1800 are illustrated in FIG. 18. Guide 1800 may be constructed out of a variety of materials including what those of ordinary skill in the related art may refer to as fully annealed steel or fully annealed tool steels. The elements may include one or more grooves 1805 that are machined into guide 1800. The length and number of grooves 1805 defines the spring rate of flexure guide 1805 that may be optimized to reliably deliver a desired spring rate. Another element may include solid hinge flexure 1830 that hingedly connects moving load carrier 1820 with fixed base 1810 to allow for movement in one axis without movement in other axes. In one embodiment, flexure 1830 is constructed of a single piece material using what those of ordinary skill in the related art refer to as a solid hinge. The solid hinge has no friction or stiction (a term commonly understood by those of ordinary skill in the relevant art to refer, generally speaking, to strong interfacial adhesion present between contacting crystalline microstructure surfaces) thus there is no wear or mechanical play in the flexure.

Returning to the illustrative example of FIG. 19, focus travel limit sensors 1920 may be provided to signal scanner firmware executables 672 of the relative position of flexure 1800 and/or that a limit of travel has been reached. Sensors 1920 may include what are commonly referred to by those of ordinary skill in the related art as Hall effect sensors. Hall effect sensors generally refer to magnetic position sensors that respond to the presence or the interruption of a magnetic field by producing either a digital or an analog output proportional to the magnetic field strength. Limit actuator 1910 may include sensor magnet 1911 and be attached to guide 1800 by commonly used methods, and thus moves in the Z 705 axis as guide 1800 and transport frame 505 moves. Sensor magnet 1911 may then be used to reference the position of guide 1800 with respect to the position of sensor 1920. Limits of travel may be further imposed upon flexure 1800 by focus travel safety limit stop 1905. Limits to the range of motion allowed for guide 1800 may be desirable in many implementations because damage to the flexure guide or other components could occur if the focus stage were to be extended too far. Thus the range of travel allowed may be predetermined, stored in scanner parameter data 677, and defined by the placements of the actuators and stop.

Translation of probe array 240 along the Y-axis may in one embodiment be accomplished by a precision linear stage, illustrated in FIGS. 16 and 17 as Y-stage 1623, coupled to what is referred to as a micro-stepped motor/driver, open loop drive mechanism or other type of motorized mechanism, referred to hereafter as Y-stage drive motor 1610. Y-stage 1623 may be constructed of a variety of materials including hardened tool steel, or other types metals designed to resist wear. Additionally, Y-stage 1623 may include a guide element to support and guide cartridge holder 1600 using various elements such as, for instance, what may be referred to by those of ordinary skill in the related art as a quad ball bearing track and carriage as well as a recirculating ball screw and nut. Y-stage 1623 may, for example, be positioned so that it rests above focus stage 1625, and have cartridge holder and pitch and roll mechanisms positioned above. In the present example, holder 1600 is fixed to Y-stage 1625 so that movement of Y-stage 1625 in the Y-axis will move the entire holder 1600 assembly, including probe array cartridge 720. One possible advantage may include independence of the mechanisms for position adjustment such that adjustment in one axis is less likely to affect the adjustments in other axes.

Linear encoder scale 1620 may, in some embodiments, be included that employs a graduated scale of measurement that is readable by linear encoder sensor 1630. Linear encoder sensor 1630 may be an optical, magnetic, or other type of sensor enabled to read position information from scale 1620. The position information may then be provided to firmware executables 672 that may be used for accurate control of Y-stage motion reducing the probability of position errors relating to the Y-axis, as will be described in detail below. For example, during fluorescence acquisition, the Y-stage may translate probe array 240 of probe array cartridge 720 underneath arcuate path 250 of objective lens 145. The translation distance for each pass of arcuate path 250 may include 2.5 µm increments that in many implementations of probe array 240 enable the complete acquisition of all of the required pixels in the Y-axis. In the present example, the Y-stage position information provided by sensor 1630 may be used for one or more methods to reduce Y-axis position error, including correcting acquired image data by adjusting pixel position placement based, at least in part, upon calculated error values from measured position information. In the described example, pixel position placement may refer to a computational method for image generation of acquired pixel data, where software, such as firmware 672, generates an image by placing the acquired pixel data in an appropriate position based on one or more parameters including y-axis error, to generate an image that accurately reflects the scanned probe array.

Figure 28:
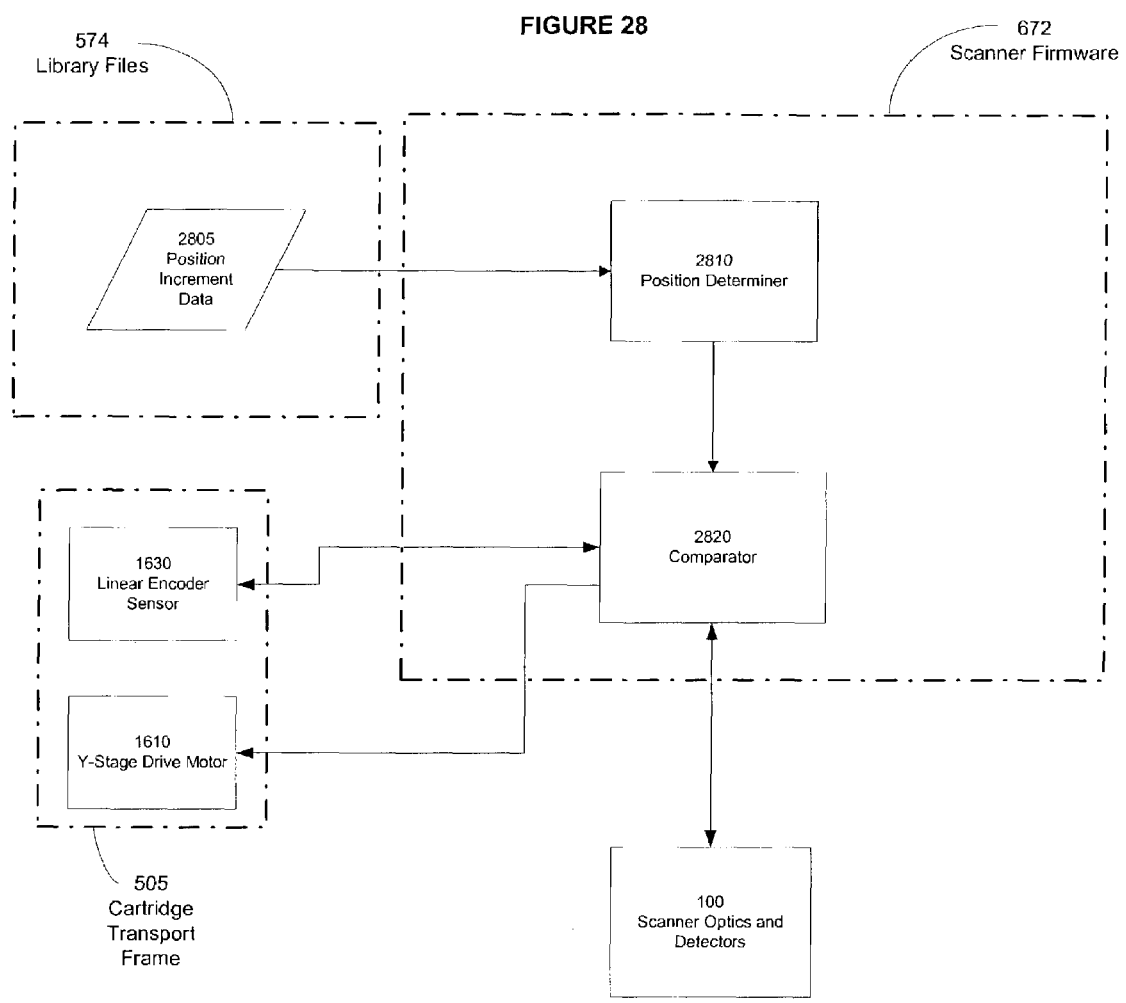
FIG. 28 is a functional block diagram of one embodiment of the scanner firmware interaction with linear encoder for control of the Y-Stage motor of FIG. 16.
Figure 29:
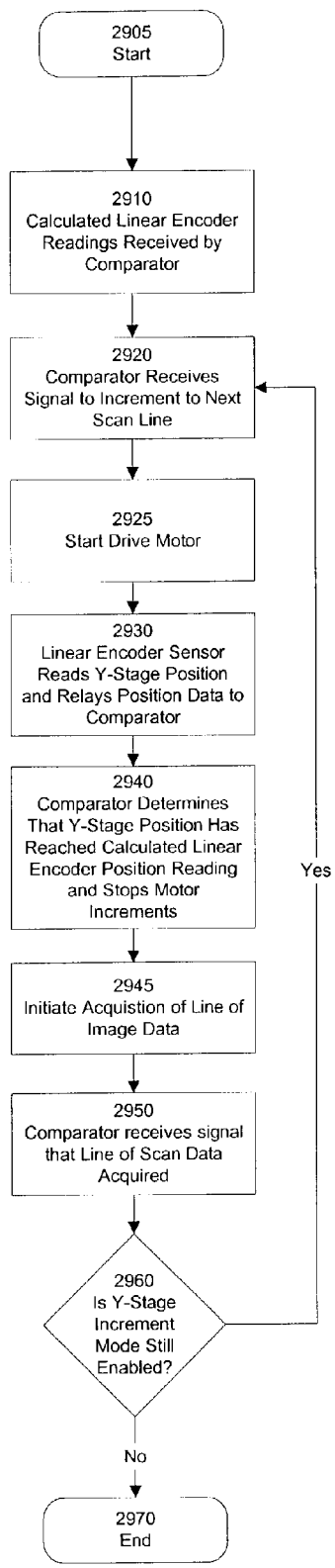
FIG. 29 is a functional block diagram of one embodiment of a method for linear encoder control of Y-Stage motor of FIG. 16.

Another implementation of a method for reducing Y-axis position error is illustrated in FIGS. 28 and 29. The implementation includes a method for firmware 672 control of Y-stage motion using position information provided by sensor 1630 that enables very fast interruption of Y-stage drive motor 1610. As illustrated in FIG. 29, step 2905 enables a Y-Stage increment mode and identifies a scan line increment. Position determiner 2810 receives position increment data 2805, according to step 2905, in order to calculate the next desired position according to linear encoder scale 1620. Each calculated position corresponds to the line acquisition positions that Y-stage 1623 must stop at for the appropriate acquisition of a line of image data. For example, the Y-stage position increments could include 2.5 µm as in a previous example or some other distance relative to the features of the scanner and probe array 240. In the present example, the line acquisition positions according to linear encoder scale 1620 could be 2.5, 5, 7.5 µm, etc. until the entire probe array has been scanned in the Y-axis.

Each calculated position may be received by comparator 2820 as illustrated in step 2910. Comparator 2820 receives a signal to increment to the next scan line position from scanner optics and detectors 100, illustrated as step 2920, and instructs Y-stage drive motor 1610 to move in the desired direction as illustrated in step 2925. Encoder Sensor 1630 reads the position of the Y-stage as illustrated in step 2930, by linear encoder sensor 1630 and relayed to comparator 2820. When the Y-stage 1623 has reached the next calculated position as illustrated in step 2940, comparator 2820 stops the motor increments and holds the Y-stage in position for example by using what is known to those in the art as a fixed holding current.

In steps 2945 and 2950, comparator 2820 signals scanner optics and detectors 100 to acquire a line of scan data and receives a signal when the acquisition is complete. Those of ordinary skill in the relevant art will appreciate that many possible methods of communication between components are possible and the example is presented for the purposes of illustration only. As an example, a third component that is independent of the comparator 2820 and scanner optics and detectors 100 may serve as an intermediary for the transmission of signals and commands. Alternatively, comparator 2820 may implement the incremental Y-stage movement within a desired period of time such as, for instance, 10 milliseconds. At the end of the desired period of time, scanner firmware 672 may automatically initiate the acquisition of a line of scan data by scanner optics and detectors 100.

As illustrated by decision element 2960, if position determiner 2810 signals comparator 2820 to remain in Y-stage increment mode, method steps 2910 through 2950 are repeated. Otherwise the method has finished as illustrated in step 2970, indicating that the probe array has been completely scanned.

In some implementations, probe array cartridge 720 generally remains in the same plane of orientation with respect to scanner 400 from the point that it is loaded into scanner 400 to the point at which it is ejected. This may apply to all operations of the scanner including the auto-focus and scan operations. For example, cartridge 720 may be received by the scanner at the load position in a vertical orientation, where probe array 240 would be located on one of the side faces of the cartridge. While remaining in the same vertical orientation the cartridge is placed into transport frame 505. Probe array 240, housed in probe array cartridge 720, is positioned into the best plane of focus by manipulating the probe array cartridge via the pitch 703, roll 700, and Z 705 mechanisms. The probe array is then scanned along Y 707 axis, and the probe array cartridge is returned upon completion to the load position via transport frame 505 in the same vertical orientation that it was received in.

Auto-Focus/Auto-Zero Executables and Data 674: In the illustrated implementation, auto-focus/auto-zero executables 674 occur prior to scanning what may be referred to as the active area of probe array 240. The term "active area" as used herein, generally refers to the area of probe array 240 that contains experimental probes. There may, in many implementations, be a variety of features located outside of the active area, including chrome border 710, one or more control features, or other elements not directly related to a biological experiment. In the illustrated implementation, auto-focus/auto-zero executables 674 may execute a number of operations for the purposes of measuring and adjusting the position of probe array 240 in a plurality of axes including pitch 703, roll 700, and Z 705 so that all probe features of probe array 240 are in the plane of best focus, and may herein be referred to as "auto-focuser". The term "plane of best focus" as used herein generally refers to an optical plane parallel to the plane of galvo rotation 149 where excitation beam 135 is focused to a spot size that may correspond to what is commonly referred to as the beam "waist". As will be described in greater detail below, a spot size in some non-limiting implementations is a 3.5 µm spot that may be optimal for fluorophore excitation and fluorescent emission detection. It will be understood that other spot sizes may be appropriate under the illustrated or alternative implementations and/or experimental conditions.

Figure 7A:
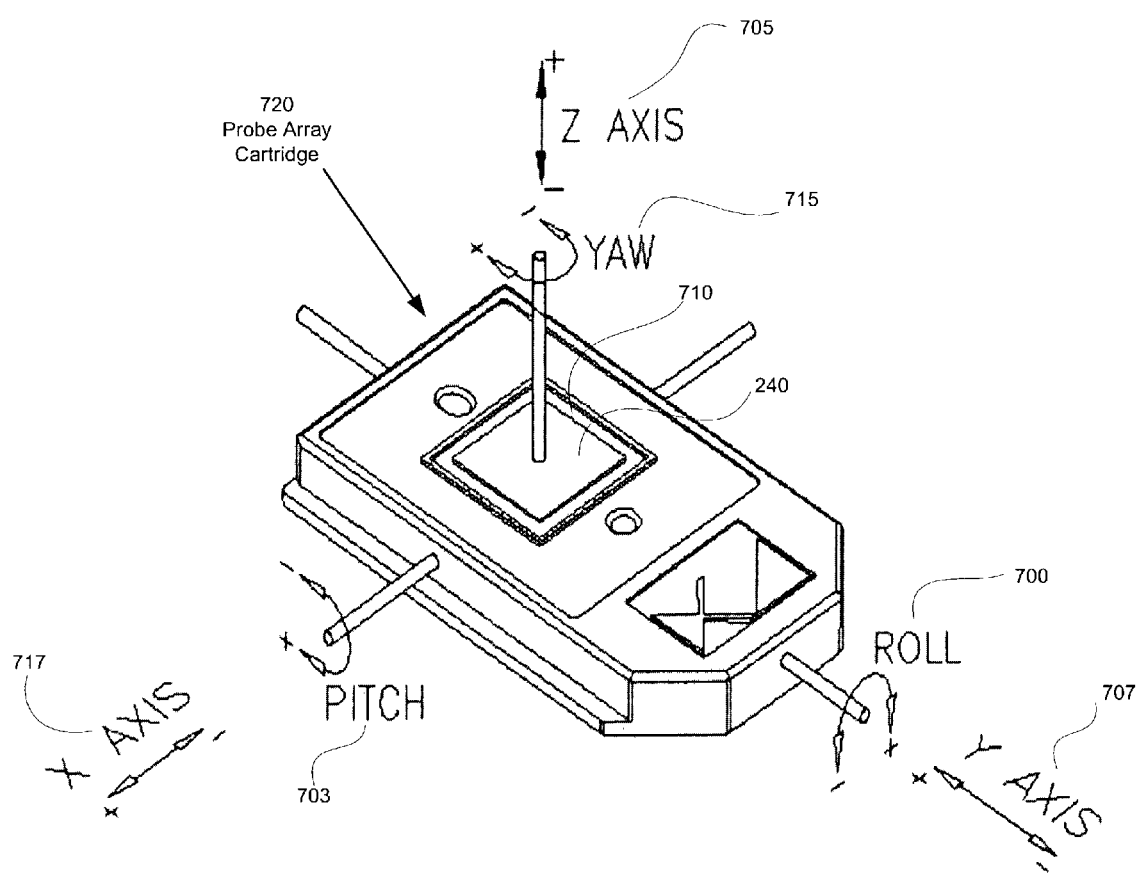
FIG. 7A is a graphical representation of one embodiment of the probe array of FIG. 2 housed in a cartridge, and illustrative examples of axes of movement.
Figure 7B:
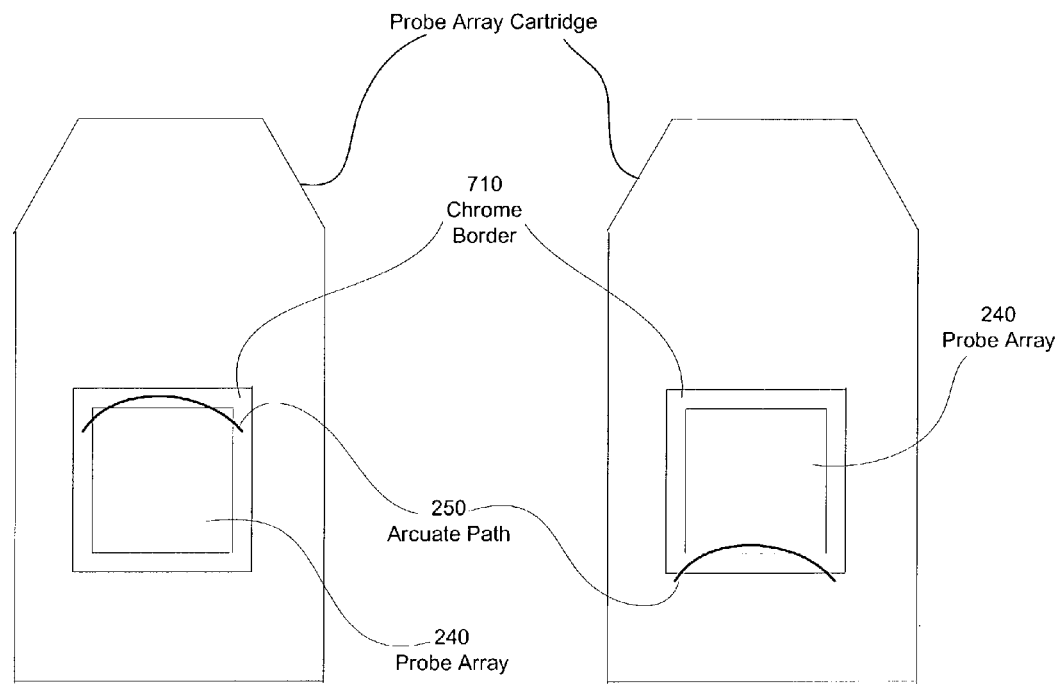
FIG. 7B is a graphical representation of one embodiment of a probe array cartridge such as in FIG. 7A including examples of an arcuate path crossing a chrome border for auto-focus methods.
Figure 7C:
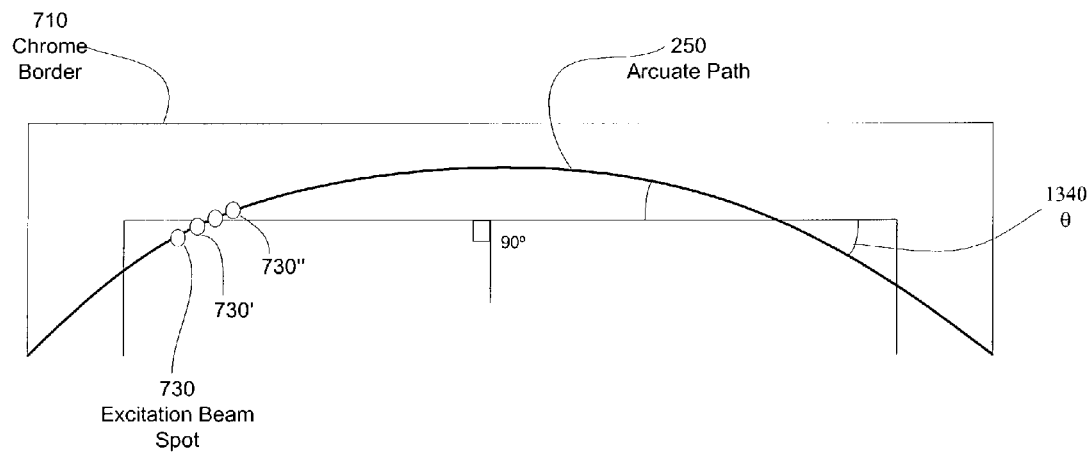
FIG. 7C is a graphical representation of one embodiment of the arcuate path crossing the chrome border of FIG. 7B including a plurality of excitation beam spots.

Illustrated in FIGS. 7A and 7B is an example of probe array 240 housed in cartridge 720 in which probe array 240 may be bounded by chrome border 710. In the present example, chrome border 710 may be located on the inside surface of the glass that covers probe array 240, where both the chrome border and probe array are in close proximity and are in the same plane of focus. In one embodiment chrome border 710 may have a minimum width that, for instance, could include a width larger than the diameter of a spot size associated with the focus plane at the maximum range of travel away from probe array 240 in the Z 705 axis. As those of ordinary skill in the related art will appreciate, a minimum spot size corresponds to the beam waist and as the distance increases from the best plane of focus (i.e. the beam waist), the associated spot size diameter increases. Thus, the size of a reflected spot may vary according to the plane of focus and are generally smallest at the waist, may herein be referred to as "reflection spots". An embodiment of auto-focus/auto-zero executables and data 674 may use a measure of the spot diameter to determine the best plane of focus, as will be described in detail below.

In some implementations of an auto-focus operation, the best plane of focus may be determined, at least in part, using a spot of reflected light of predetermined size produced by excitation beam 135 and focused onto chrome border 710. For example objective lens 145 focuses excitation beam 135 to a location, illustrated in FIG. 7C as spot 730, and scans along an arc in the direction of the X-axis, illustrated in FIG. 7B as arcuate path 250. Spot 730 is reflected from chrome border 710 that in the present example could illustratively be assumed to have a width of 100 µm, although a variety of different widths are possible. In the present example illustrated in FIGS. 7B and 7C, executables and data 674 may use data corresponding to the intensity of the reflected light from spot 730 from a single pass of arcuate path 250 across the top border of chrome border 710 and subsequently from a single pass across the bottom border. Spot 730 from may cross chrome border 710 at angle θ 1340, where θ 1340 may correspond to an angle between the ranges of 0 and 90 degrees, or 90 to 180 degrees, being more to the extremes of 0 and 180 degrees respectively. For example angle θ 1340 may be almost tangential to chrome border 710, creating a large number of data points and allowing for calculation of a slope value, as will be discussed in detail below. In the present example, the reflected intensity data used for calculating the slope value may correspond to a range of reflected intensity values starting from the point that spot 730 begins to cross chrome border 710, illustrated as spot 730', to the point that entire diameter of spot 730 has crossed and is completely reflected by border 710, illustrated as 730".

For the purposes of comparison, those of ordinary skill in the related art will appreciate that if, for example, spot 730 crosses the plane of the chrome border at an angle of 90 degrees, the duration of time between the point when the beam first crosses the plane to the point when the beam has completely crossed plane would be shorter than if the angle was almost tangential to the plane. In the present example, the result of the shorter time duration would be the collection of a smaller number of data points and would not allow for calculation of a slope value. As will be further described in detail below, having a large number of data points may be desirable for a variety of reasons including the reduction of error inherent in the reflected intensity data.

In one embodiment, the reflected intensity data collected by executables 674 may be representative, for instance, of the measured intensity of reflected spot 730 by detector 192. For example, those of ordinary skill in the related art will appreciate that the reflected intensity may be the greatest at the beam waist where the light from excitation beam 135 is the most concentrated, as will be described in greater detail below. Additionally, the low end of an intensity range from a set of collected data points from a single pass of arcuate path 250 over either the top or bottom portion of chrome border 710 may be representative of data collected when spot 730 partially overlaps the plane of chrome border 710 (i.e. spot 730') and peaks at the high end of the intensity range when the beam has completely crossed the plane of the chrome border 710 (i.e. 730").

Figure 7D:
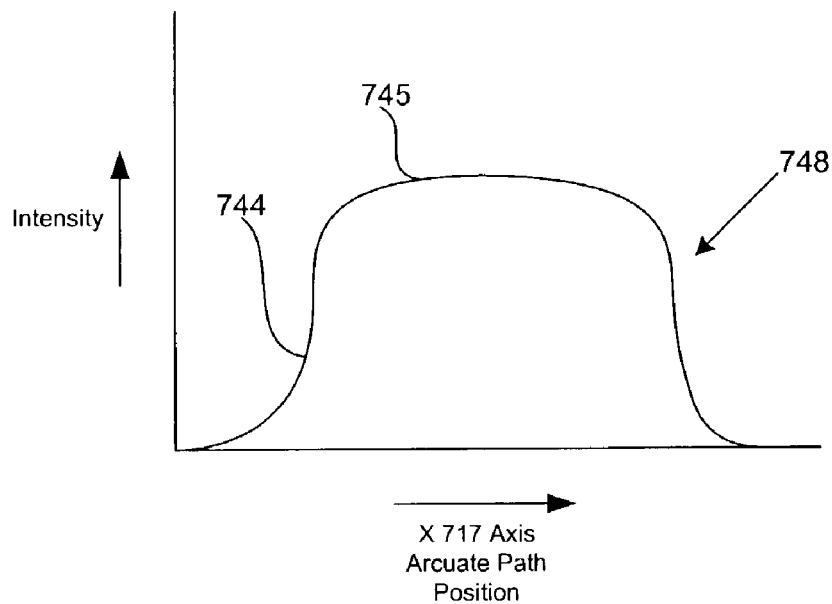
FIG. 7D is an illustrative example of one embodiment of reflected-beam intensity data from the plurality of excitation spots of FIG. 7C as plotted on a graph including slope values.

An illustrative example of a method that may be used by executables 674 is presented in FIG. 7D. The illustrative representation includes a set of collected data points from a single pass of arcuate path 250 over chrome border 710, plotted on a graph and fitted with a line that forms plateau shape 748. The collected data points on plateau 745 correspond to the level of maximum measured intensity as described above. Slope 744 of the fitted line may be calculated by executables 674 for the range between the point represented by spot 730' when the beam first crosses the plane of chrome border 710 and to the point maximum emission intensity 745 of plateau 748. Executables 674 may independently perform the method for the top border and the bottom border for a known position in the Z 705 axis. In the present example, executables 674 stores a plurality of values that may include slope 744 for the top and slope 744 for the bottom, and Z 705 position. Those of ordinary skill in the related art will appreciate that two smaller peaks in the X 717 axis may be associated with the graph for the collected data from the bottom chrome border due to arcuate path 250. In such a case, the calculation of slope 744 may be made from a single peak chosen either randomly or based upon one or more characteristics, or alternatively averaged from both peaks.

Figure 7E:
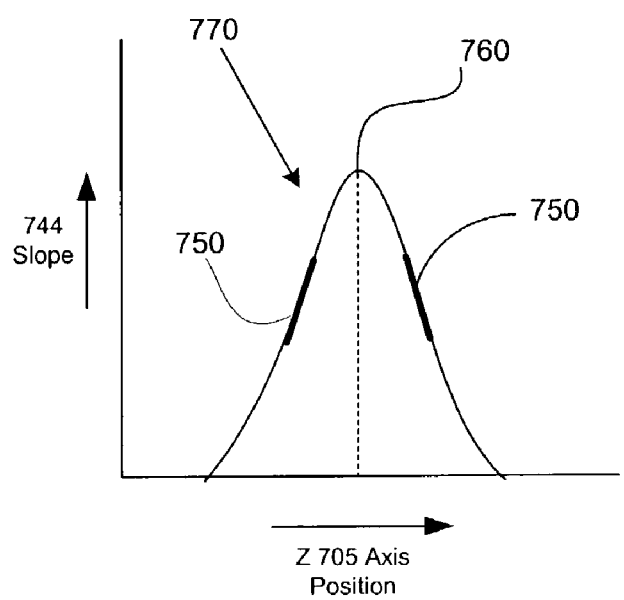
FIG. 7E is an illustrative example of one embodiment of slope values of FIG. 7D plotted on a graph including a point associated with the best plane of focus.
Figure 8:
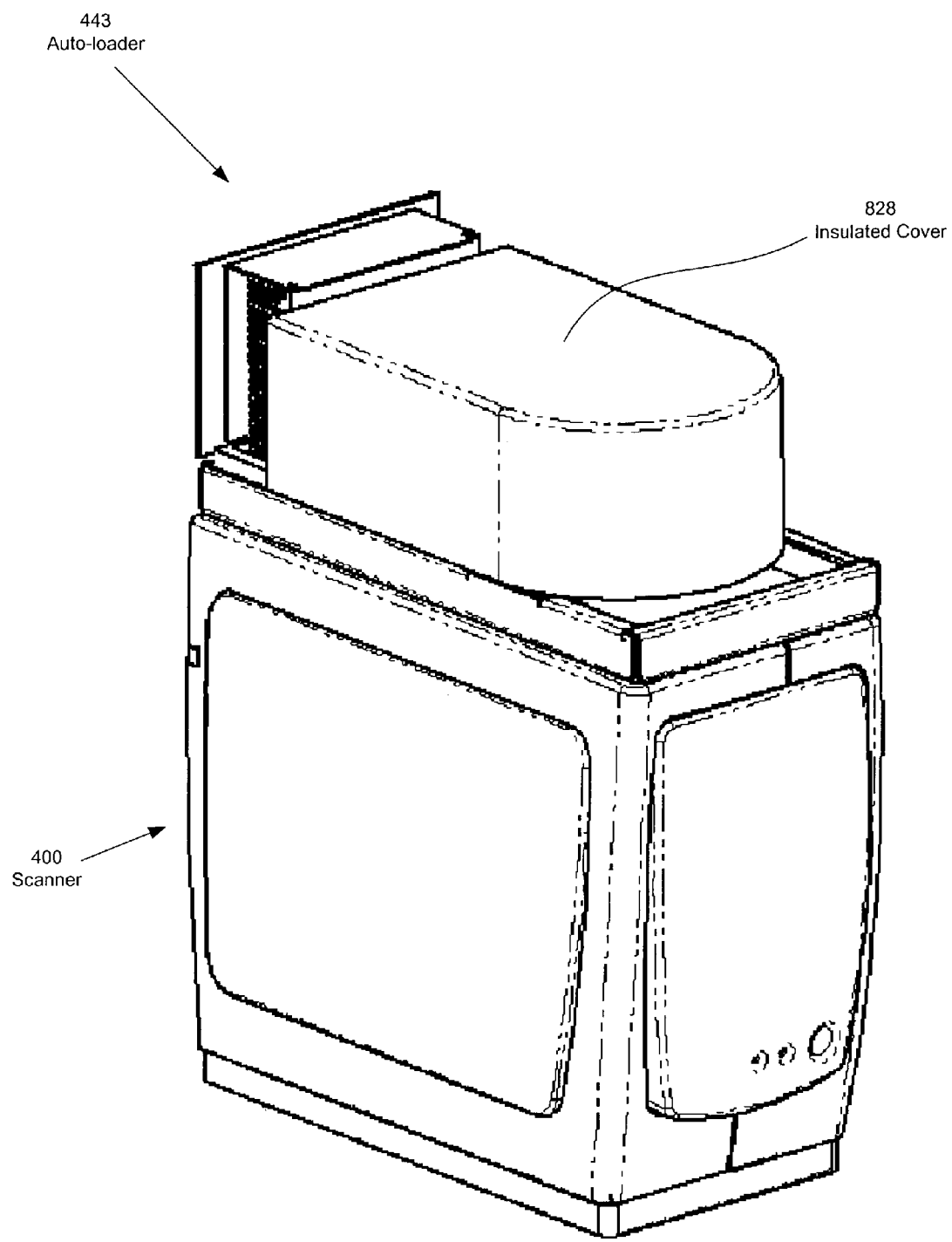
FIG. 8 is a simplified graphical representation of one embodiment of the scanner and auto-loader devices of FIG. 4.

In one embodiment, executables 674 may repeat the above described method for a number of successive Z 705 positions. For example, executables 674 may perform the first iteration of the method at a distance known to be outside the plane of best focus that could be useful as a reference. Executables 674 may iteratively perform the method at successive incremental distances in the Z 705 axis between objective lens 145 and probe array 240. Executables 674 may then plot calculated slope 744 for each Z 705 position on a new graph independently for the collected data from the top and bottom, as is illustrated in FIG. 7E. In the present example, it may be desirable for the purpose of reducing error to eliminate data points from the high and low extremes of the slope values and fit a line to the remaining data points. The data points used for calculations could, in one possible implementation, be located in range 750 that may, for instance, include a range between sixty and seventy percent of the maximum value. Executables 674 may then calculate and fit parabolic line 770 to the data points within range 750. In this example, the plane of best focus corresponds to the Z-axis position associated with the maximum height 760 of parabolic line 770 that represents the distance when the minimum beam spot size is achieved corresponding to the highest measured intensity. Alternatively, in some implementations the height at which the laser spot size is the smallest may not be the height at which the amount of reflected laser light collected is a maximum due to characteristics of one or more of the optical elements. Instead one or more of the pinholes may be positioned so that the focus height is one for which "best compromise" of light collection, light filtering, and PMT response for the range of wavelengths emitted by a particular fluorophore is achieved.

In some embodiments it may, for example, be desirable to first perform the auto-focus methods described above to bring a first chrome border that could be either the top or bottom chrome border, into the best plane of focus. Secondly, perform the methods to bring the second chrome border not adjusted in the first iteration of the method into the best plane of focus. Then, the auto-focus methods may be repeated upon the first chrome border to compensate for error introduced while adjusting the second border. Additionally, it may be desirable to use convolution methods that may, for instance, be used to compare the shape of line 770 to an expected shape associated with a desired result. The term "convolution" as used herein, generally refers to one or more methods that include an integral which expresses the amount of overlap of one function g as it is shifted over another function f, and therefore "blends" one function with another.

In many implementations, objective lens 145 forms what is referred to as a convergent/divergent beam that, for example, may resemble two cone shapes joined together at their points. The beam's waist (the location where the points of the cones join) correspond to the minimum spot size defined in the illustrated implementation as the plane of best focus. Executables 674 may adjust the Z 705, pitch 703 and roll 700 positions of the array individually or in a variety of combinations using the corresponding elements of transport frame 505 to achieve best focus. As probe array 240 is moved closer to best focus, the laser spot size approaches the minimum spot size for both the top and bottom borders. Once auto-focus executables 674 determines that the array is in best focus, no further motion is applied in Z 705, pitch 703 or roll 700. If, for example, after the completion of the auto focus operation modifications are made to the position of probe array cartridge 720, then executables 674 will perform the auto-focus operation again to position probe array 240 in the best plane of focus. In some embodiments, dynamic focusing of the array typically need not occur during scanning, as the plane of focus is not affected as cartridge 720 is translated along the Y 707 axis.

Auto-focus/auto-zero executables 674 may require number of data variables that for instance may be stored locally in scanner parameter data 677 to perform its operations. One or more elements of scanner parameter data may have been imported from a remote source such as from library files 574; intermediate results, lab data, and image data 401A; or other remote source of data. An example of one of the many possible data variables passed into executables 674 may be probe array type data that may define the physical parameters that executables 674 uses to accurately position the probe array in the best plane of focus. In the present example the probe array type data variable may be provided to executables 674 by barcode reader 502, or may alternatively be stored in one or more data files that, for instance, may have been created by experimenter 475 and identified by a barcode identifier. The data variables may be categorized by the routines they perform that could include, but are not limited to, Y 707 position of the top edge of the bottom chrome, Y 707 position of the bottom edge of the top chrome, nominal thickness of chrome border 710, distance from the inside edge of chrome border 710 to the edge of the active area, width of the scan, laser power, PMT gain, Z 705 step size, and Z 705 position used for searching for chrome. Those of ordinary skill in the relevant art will appreciate that variables may be involved in one or more categories, and that a variables use in one category may not limit its use in another category.

In some alternative implementations, variables and other aspects of the auto-focus operations may be stored and executed by scanner control and analysis executables 572, stored in system memory 570 of computer 350 and communicated to scanner 400 through input-output controllers 575. Variables and other related data may in some implementations also be stored in experiment data 577, or other memory storage located on computer 350 or remotely from it. For example, some auto-focus operations could include instructions that may be based in part on the probe array type, and sent to transport frame 505 for the purposes of maneuvering the probe array into the appropriate position. In the present example other auto-focus operations could also include the initiation and control of the movement of the scanning arm, laser activation and collection emitted light, calculation of emitted light intensities and the plane of best focus. The previous examples are presented for illustration only, and are not intended to be limiting in any way.

In one embodiment, executables 674 may additionally perform auto-zero operations prior to an active area scan of each probe array to maximize what is commonly referred to by those of ordinary skill in the related art as the signal to noise ratio. In other words enhance the difference between noise in the system and signal from detected emissions. There may be many sources of noise that could affect the resolution of an acquired signal (i.e. the noise may mask all or part of a signal) including local radio or television stations, equipment plugged into the same power source, nearby conductors carrying "dirty" signals, dark current of components within scanner 400 such as PMT detectors, or other sources of noise. In some implementations, the auto-zero operations may be carried out subsequent to the auto-focus operations or vice versa.

In the presently described embodiment, scanner 400 may have a large dynamic range capable of detecting very small and very large signals (i.e. detection of low and high levels of fluorescent emission). For example, scanner computer 510 may include what is referred to by those of ordinary skill in the related art as a 16-bit data acquisition system that allows for detection of over 65,000 different levels of fluorescence detection. Variations in signal output from noise may be measured and can range from 4-8 bits, commonly referred to as least significant bits (LSB) as opposed to the bits that are closer to 65,000, commonly referred to as Most Significant Bits. In the present example, adjusting what those of ordinary skill in the art commonly refer to as channel offset value of detectors 110, 115, and 180, may be made to modulate the output from a detector to compensate for such variations. Alternatively, in some implementations it may be desirable to adjust the channel offset value of laser 120. Those of ordinary skill in the related art will appreciate that the term "channel offset" generally refers to the constant frequency difference between a channel frequency and a reference frequency. In some implementations it is desirable that the channel offsets be adjusted so that the noise is close to, but measurably above, zero LSB because values below zero LSB cannot be measured.

For example, it can be assumed for illustrative purposes that the variation present at a given point in time follows a normal or gaussian distribution. Thus, most of the variation values are clustered close to an average value of all of the variation present. If plotted on a graph, the result would look like a bell shaped curve with the average value of the variation being the peak of the curve. In the present example, one standard deviation of a gaussian distribution may be equal to 32% of the pixels being below zero LSB. Three standard deviations from the average may results in less than about 0.3% of the pixels being below zero LSB and satisfies the desired embodiment of having most of the pixel variation close to zero but measurably above. Those of ordinary skill in the related art that the term "standard deviation" commonly refers to a statistic that tells you how tightly all the various examples are clustered around the mean in a set of data.

In one embodiment of the auto-zero operation performed by executables 674, shutter 134 is closed and in some cases filter wheel 160 is turned to a position where all light to detector 115 is blocked. Signal 192 is then representative of the variation or noise present in the system. Executables 674 then makes the calculations based, at least in part, upon that variation and adjusts signal 192 accordingly. For example, after all possible sources of light are blocked, the channel offset of detector 115 could be set to a position where the variation is theoretically calculated to be above 0 LSB. The detector could take the equivalent of 60,000 readings of fluorescence and the average value could then be calculated. If that value is less than or equal to zero, then the offset value is increased by a predetermined increment such as, for instance, one or more standard deviation values, and new readings are taken using the method described above. Otherwise the average value is above zero and the offset value may be further adjusted based upon a value calculated by executables 674 that may include the difference between the measured average and a value that is three times the calculated standard deviation value for the measured variation. Executables 674 may repeat the method and perform adjustments to the channel offset value until the channel offset settings have been reached. Additional examples of noise calculation and compensation may be found in U.S. Pat. No. 6,490,578; and in U.S. patent application Ser. No. 10/304,092, titled "System, Method, and Product for Dynamic Noise Reduction in Scanning of Biological Materials", filed Nov. 25, 2002, each of which is hereby incorporated by reference herein in it's entirety for all purposes.

Auto-Loader 443: FIGS. 8-14 provide an illustrative example of one possible embodiment of an automatic cartridge loader used in conjunction with some implementations of scanner 400. Auto-loader 443 may include a number of components such as cartridge magazine 1000, cartridge transport assembly 1105, cooled storage chamber 960, and warm thermal chamber 940. A implementation may include the construction of auto-loader 443 as a two piece structure that has upper and lower sections.

The upper structure may contain components including heat exchanger 925; fan 926; warm thermal chamber 940 including thermally insulated partition 927, and chamber heating element 950; cartridge magazine 1000 including hub 1003, compartments 1010, partitions 1002, and circumferential band 1004; and insulated cover 828 that encloses cooled storage chamber 960. The lower structure could contain components such as cartridge transport assembly 1105 including reversible rollers 1106, actuation components 1110, and 1113, and spur gears 1107; and electronics. It will be understood that various configurations and distributions of these and other elements are possible, and that some elements may be combined or split into separate elements in alternative implementations.

Auto-loader 443 may be covered by insulated cover 828, that for example could include elements such as a door with a solenoid actuated latch and vibration dampened hinge to allow access for a user to load or unload individual cartridges as well as magazine 1000. In some implementations the solenoid actuated latch may be responsive to instructions from firmware executables 672. For example, firmware executables 672 may instruct the solenoid actuated latch to allow access at any time when scanner 400 is not performing any scanning function or operation. Alternatively, the solenoid actuated latch may be responsive to instructions from computer 350 via firmware 672 that may be initiated by experimenter 475. In the present example, experimenter 475 may wish to interrupt the operations of scanner 400 for a variety of reasons such as, for instance, to add or remove one or more cartridges 720 or magazine 1000, or to introduce a probe array cartridge directly into scanner 400 for immediate scanning. Experimenter 475 may use computer 350 to instruct firmware executables to interrupt one or more operations and release the solenoid actuated latch. After experimenter 475 has completed the desired task, user 475 may make a selection via computer 350 enabling firmware executables 672 to resume the one or more operations.

Some features of the embodiment include the preservation of biological integrity of the probe arrays for a relatively long period of time, such as sixteen hours or more, by controlling one or more environmental parameters of the array storage environment. Also, in the event of a power failure or error condition that prevents normal operation of scanner 400, auto-loader 443 may indicate the failure to the user and maintain a storage temperature for all probe arrays within cooled storage chamber 960 and/or warm thermal chamber 940 using an uninterruptible power supply system. Other features of the embodiment may include pre-heating probe array cartridge 720 to the same temperature as the internal environment of scanner 400 prior to transport into scanner 400.

Figure 9:
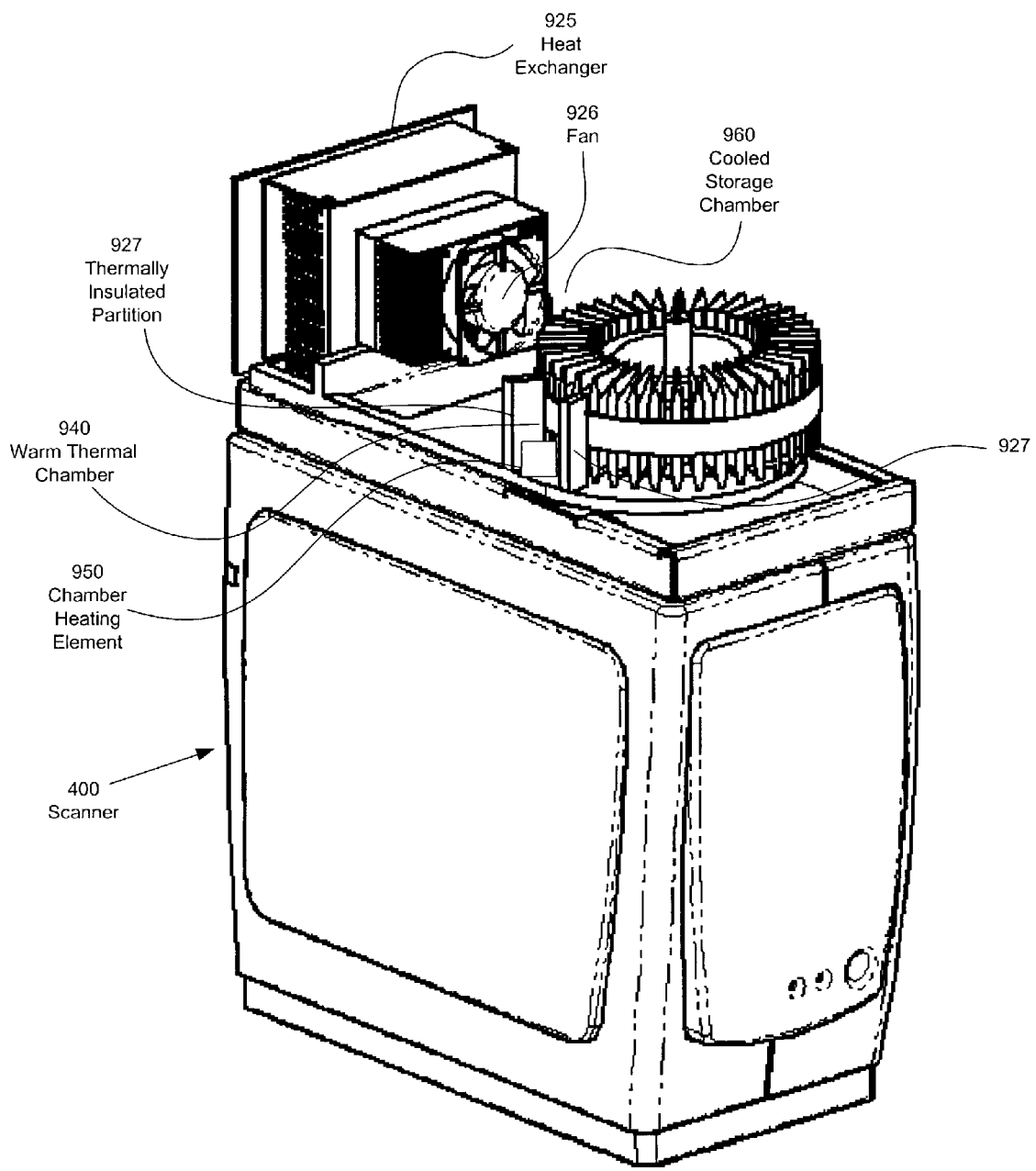
FIG. 9 is a simplified graphical representation of one embodiment of the scanner and auto-loader devices of FIG. 8 with the cover for the auto-loader removed, showing one embodiment of an internal configuration including a cartridge magazine.

The features described above provide optional equipment and techniques to transfer a plurality of probe array cartridges 720 from a temperature controlled storage environment into scanner 400 in an organized and efficient manner, and to return the cartridges to the temperature controlled storage environment following imaging. Optimal temperatures for storing cartridges may vary, but typically include temperatures preferably ranging from 2° C. to 15° C. FIG. 9 provides an illustrative example of auto-loader 443 positioned above scanner 400 secured by a plurality of mounting bosses that may be inserted through the scanner cover and fastened with self-retaining, floating hardware. In one embodiment, auto-loader 443 may be enabled to receive its electrical power from scanner 400. One possible method of electrical connection between scanner 400 and auto-loader 443 may include what is commonly referred to as a blind-mate connector that includes shielding that could be pass through a specialized opening in the scanner cover and connected to an internal power source within scanner 400. Alternative embodiments of auto-loader 443 could include an independent power supply dedicated to auto-loader 443 or other power supply method.

The embodiment may also include heat exchanger 925, enabled to provide cooling for cooled storage chamber 960. In many implementations it may be desirable to maintain a temperature range such as, for instance, a range between 2° C. to 15° C. to maintain the biological integrity of hybridized probe arrays. Fan 926 may be enabled to circulate the cooled air from heat exchanger 925 around one or more probe array cartridges 720 positioned in magazine 1000. In one embodiment of the invention, one or more thermostats may be included to provide temperature measurements to firmware executables 672 of the air surrounding the probe array cartridges 720 and/or the ambient air temperature associated with the internal environment of scanner 400. Firmware executables 672 may activate exchanger 925 as necessary to maintain a desired temperature, and additionally provide sufficient cooling so that probe array cartridge 720 could be cooled to the desired temperature in one hour or less. An alternative embodiment may include a more direct means of temperature measurement such as, for instance, measuring the temperature of probe array cartridge 720 using an infrared detector. An infrared detector, as it is known to those of ordinary skill in the relevant art, is enabled to detect temperature from a specific location and be tuned to a specific temperature range so that thermal noise from air or other sources will not affect it. For example, an infrared temperature detector may not require physical contact with a probe array cartridge to specifically read its temperature. The infrared detector may be aimed at a specific location on a probe array to detect the temperature at that location. In the present example, the infrared detector detects the infrared energy (i.e. heat energy) emitted by the probe array cartridge.

Also illustrated in FIG. 9 are thermally insulated partitions 927 that may be enabled to separate warm thermal chamber 940 from cooled storage chamber 960. In one implementation, thermally insulated partitions 927 are aligned radially with cartridge magazine hub 1003, and aligned with partitions 1002. When properly positioned a seal is formed between partitions 927, partitions 1002, and insulated cover 828, thus thermally isolating warm thermal chamber 940 and a plurality of compartments 1010 from the remainder of magazine 1000. Firmware executables 672 may provide temperature control to warm thermal chamber 940 using chamber heating element 950. For example heating element 950 may include a recirculating fan and what may be referred to as a heat sink or resistive heater to warm the air. In the present example, chamber 940 may be enabled to warm a plurality of probe array cartridges quickly so that, for instance, within a time period of ten minutes or less the one or more probe array cartridges within chamber 940 may be warmed to the temperature.

In the presently described embodiment, previously cooled air from cooled storage chamber 960 may be used by chamber heating element 950. The previously cooled air may enable warm thermal chamber 940 to prevent condensation from forming on the surface of probe array cartridge 720. It will be appreciated by those of ordinary skill in the related art that warm air is capable of holding more water vapor than cold air, thus cooling often forces the air to lose some measure of water vapor (i.e. become drier) depending upon how cold the air becomes. It may be desirable in many implementations to prevent condensation formation for a variety of reasons including the distortion of images and/or the obstruction of probe array features from the view of scanner optics and detectors 100.

Warm thermal chamber may, in one embodiment, be enabled to hold a plurality of probe array cartridges 720. Holding a plurality of cartridges may provide sufficient time for the temperature of a probe array cartridge to change from the temperature of cooled storage chamber 960 to the temperature of warm thermal chamber 940 prior to being loaded into scanner 400. For example, warm thermal chamber 940 may have the capacity to hold two probe array cartridges. In the present example a first cartridge may be positioned over the load point and loaded into scanner 400 by transport assembly 1105, while a second cartridge 720 remains in a waiting position in warm thermal chamber 940. The first cartridge may be loaded into scanner 400 via transport assembly 1105, and subsequently returned after the completion of scanning operations. Firmware executables 672 may then advance magazine 1000 by one position of compartment 1010 so that the first cartridge is now moved out of warm thermal chamber 940 and into cooled storage chamber 960. The second cartridge that was in the waiting position in chamber 940 has been warmed to the temperature of warm thermal chamber 940 and moved to the loading position. A new, third cartridge has entered warm chamber 940 into the waiting position from cooled storage chamber 960 and begins to warm. The previous example is for the purposes of illustration only and it will be appreciated to those of ordinary skill in the art that many variations may exist.

Warm thermal chamber may use similar methods of temperature measurement as those described above with respect to cooled storage chamber 960. Returning to the previous example of using an infrared detector for measuring the temperature of a probe array cartridge, the temperature of the probe array cartridge is precisely measured and the information immediately relayed to firmware executables 672. This enables firmware executables 672 to respond to minute temperature variations that may exceed ideal limits. Thus the potential of overheating a probe array cartridge may be reduced and higher air temperatures could be used to heat the probe array cartridge more quickly. In the present example, the infrared detector could be aimed at a plurality of possible locations on probe array cartridge 720 including the glass over the probe array, the top or bottom of the outer exposed edge of the probe array cartridge when loaded into the magazine 1000, the bottom edge of the probe array cartridge that could be viewed through an additional opening in base 1314, or other location on the probe array cartridge.

In one embodiment, firmware executables 672 may instruct auto-loader 443 to alter its mode of operations between a plurality of different modes, where each mode may have distinct utility and operating parameters. For example, auto-loader 443 may change from a scanning mode to a long-term storage mode after all probe array cartridges contained in magazine 1000 have been scanned. In the present example, when auto-loader 443 enters the long term storage mode, heating element 1550 is turned off and cartridge magazine 1000 periodically advances by one or more positions of compartments 1010 to bring all the probe arrays contained in magazine 1000 to an equal and cool temperature. The capability to change modes enables the user to set up one or more experiments and leave it for an extended period without compromising the data collection process or integrity of the biological samples. The user may use computer 350 to set up and store one or more experimental parameters in experiment data 577 that scanner control and analysis executables 572 may then provide to firmware executables 672.

Figure 10:
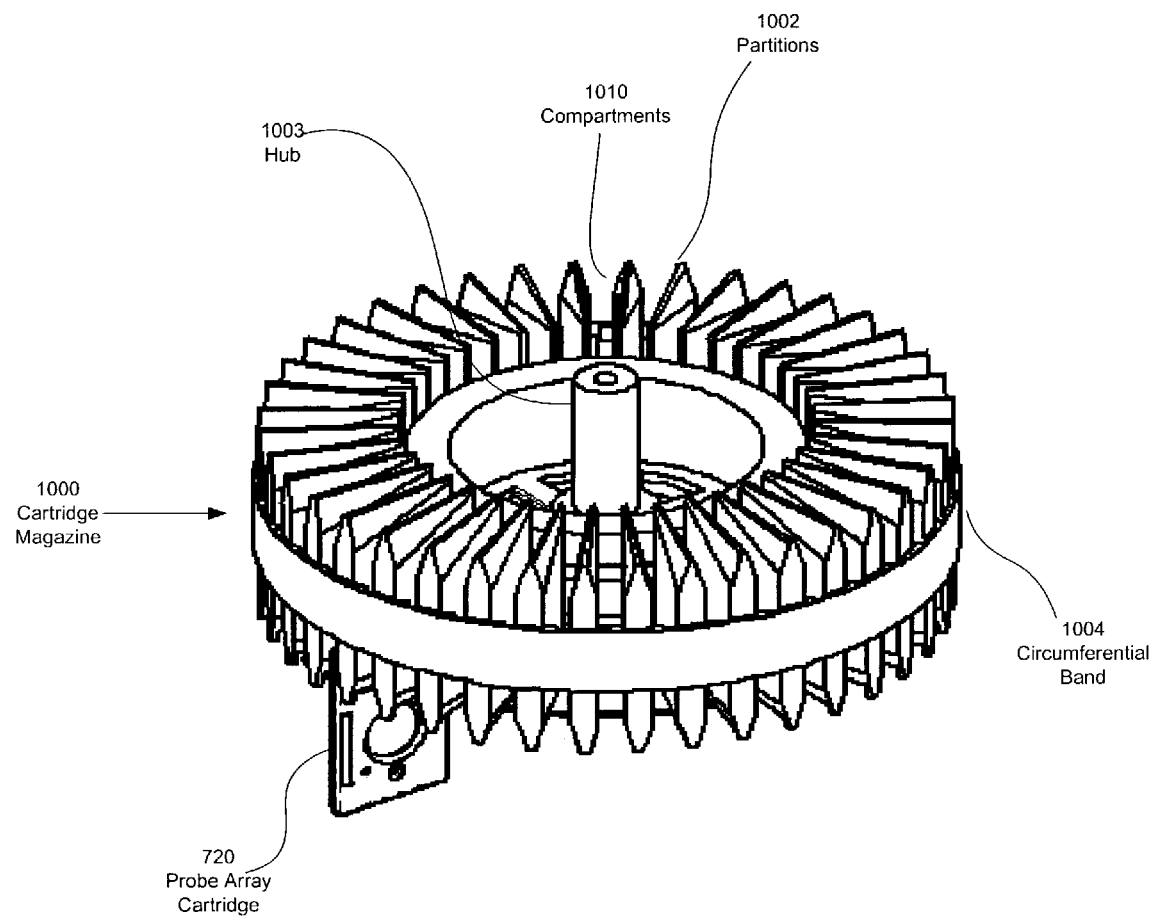
FIG. 10 is a graphical representation of one embodiment of the cartridge magazine of FIG. 9.

FIG. 10 illustrates an example of cartridge magazine 1000 that in one embodiment is removable from auto-loader 443. Magazine 1000 may be capable of holding a range of one or more cartridges, for instance, a range from 1 to 100 cartridges is possible. Although it is commonly understood that many other possible ranges exist. For example, some embodiments could include a cartridge magazine that holds up to 32 or 48 cartridges. Additional components and features of magazine 1000 may include partitions 1002 that hold and maintain separation between probe array cartridges 720. It may be desirable that magazine include a barcode with an associated barcode identifier that could, for instance, be used to identify one or more of the probe array cartridges contained in magazine 1000, identify experiments, or other type of information. In one embodiment each of compartments 1010 may hold a single probe array cartridge, although alternative implementations may include each of compartments 1010 holding 2, 3, or more probe array cartridges. The separation provided by partitions 1002 includes physical and thermal separation, where partition 1002 may act as a thermal barrier between the compartments. Another component includes hub 1603 in the center of magazine 1600 that is the center of rotation of the cartridges about the vertical axis of the magazine. Also, circumferential band 1604 encircles cartridge partitions 1602 providing structural support for magazine 1600.

Probe array cartridges 720 may be oriented vertically or horizontally in magazine 1000, and loaded with no sequential relationship to one another. For example, scanner 400 may include a barcode reader that is capable of reading one or more barcode identifiers from barcode label 1500 that firmware executables may use to identify the specific probe array cartridge 720. Also in the present example, it may not be required that each of compartments 1010 contain a probe array cartridge. Auto-loader 443 may include one or more sensors such as, for instance, an optical sensor that may enable firmware executables 672 to recognize and skip empty locations in magazine 1000.

In some embodiments, cartridge magazine 1000 may implement a variety of different methods for the orientation and movement of probe array cartridges 720. For example, probe array cartridges 720 may be oriented horizontally in magazine 1000 on one of the side edges of the cartridge. In a separate example, the cartridges may be in a different style of magazine where the cartridges could be positioned so that they lie flat on the front or back face of the cartridge. The magazine could be constructed such that the cartridges may be stacked vertically resembling a deck of cards. In the present example a cartridge from the bottom of the stack could be removed for scanning operations, advancing the remaining cartridges in the stack down by one position. The removed cartridge could then be placed back on the top of the stack, or alternatively be added to a different stack.

Cartridge magazine 1000, including partitions 1002, hub 1003, and band 1004, may be constructed of plastics, metals, or combinations thereof, or other appropriate materials. For example one embodiment could include cartridge magazine 1000, including the hub 1003, partitions 1002, and circumferential band 1004, comprised as a single piece of injection-molded plastic such as ABS.

Figure 11:
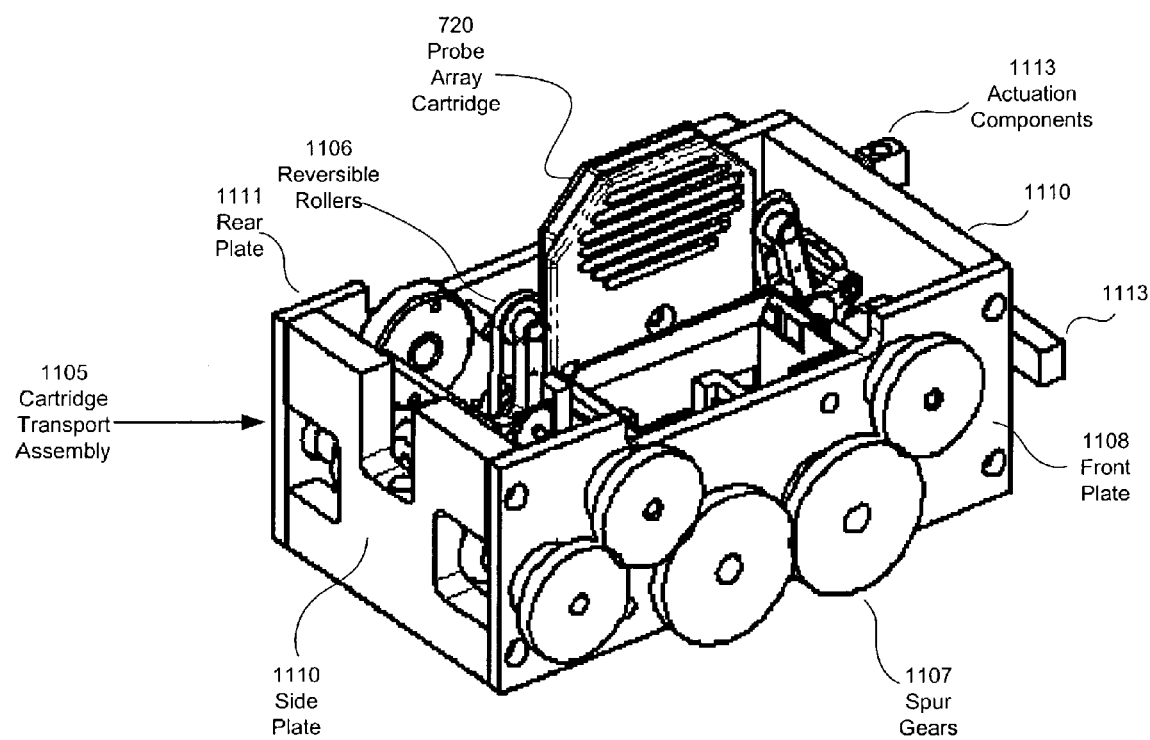
FIG. 11 is a graphical representation of one embodiment of a transport assembly that includes reversible rollers.

FIG. 11 is an illustration of cartridge 720 located within cartridge transport assembly 1105. Cartridge transport assembly 1105 includes reversible rollers 1106 that manipulate cartridge 720. Spur gears 1107 are driven by a motor (not shown) to power the motion of rollers 1106. A housing comprising a front plate 1108, side plates 1110, and rear plate 1111, as well as actuation components 1113 that activates the capture and release of cartridge 720 by rollers 1106. Similar to magazine 1000, cartridge transport assembly 1105 may be constructed of a variety of materials including plastics, metals, or combinations thereof, or other appropriate materials. For example, plates 1108, 1110, and 1111 as well as parts of rollers 1106 and actuation components may be constructed of aluminum or other type of metal while elements such as spur gears 1107 and/or parts of rollers 1106 may be constructed of plastic.

Illustrated further in FIG. 12 is an example of how cartridge 720 and rollers 1106 may interact. In the illustrated example rollers 1106 may be extended towards and engage one or more fiducial features of probe array cartridge 720 via actuation components 1113. Movement of the rollers in a first direction will impel the cartridge downwards, while movement of the rollers in the reverse direction will impel the cartridge upwards. Rollers 1106 may be disengaged and retracted from probe array cartridge 720 via actuation components 1113. In one embodiment, reversible rollers 1106 may reversibly translate probe array cartridge 720 across the distance between magazine 1100 and scanner 400.

Figure 13:
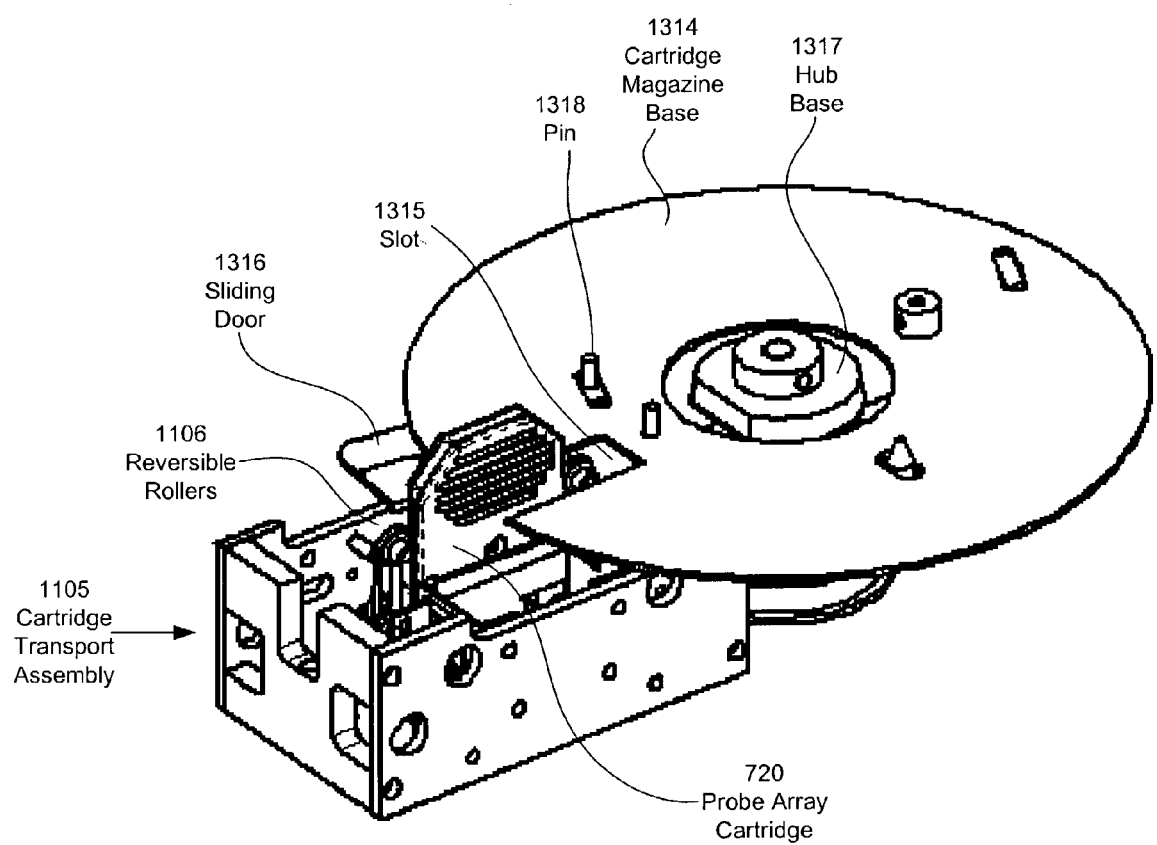
FIG. 13 is a graphical representation of one embodiment of the transport assembly of FIG. 11 including one embodiment of a cartridge magazine base.
Figure 14:
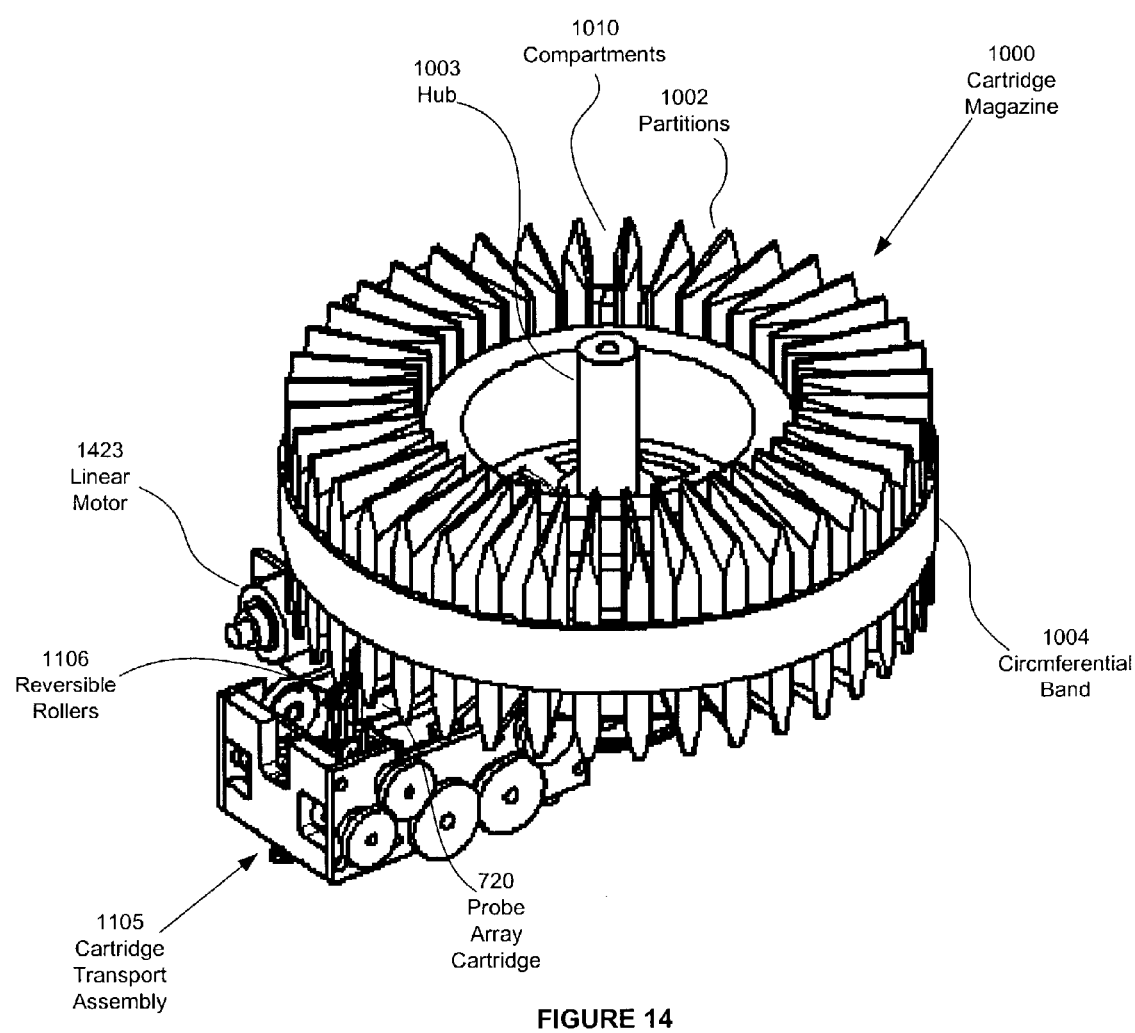
FIG. 14 is a graphical representation of one embodiment of the transport assembly of FIG. 11 and 13 and the cartridge magazine of FIG. 10 assembled together.

FIGS. 13 and 14 further provide an illustrative example of the interaction between cartridge transport assembly 1105, cartridge magazine base 1314, and cartridge magazine 1000. Cartridge magazine base 1314 includes slot 1315 that is associated with the loading position and may provide for through-passage of a selected probe array cartridge between magazine 1000 and cartridge holder 1600 of scanner 400. Cartridge magazine base 1314, in conjunction with partitions 1002 are enabled to support and hold the one or more probe array cartridges in place. When probe array cartridge 720 is positioned in the magazine loading position over slot 1315, it may be supported on the underside by sliding door 1316. Under the control of firmware executables 672, sliding door 1316 may block or allow passage of the probe array cartridge through transport assembly 1105. For example, firmware executables may extend reversible rollers 1106 and engage probe array cartridge 720. In the present example rollers 1106 may be enabled to reach above the level of cartridge magazine base 1914 with sliding door 1316 in the closed position and engage the one or more fiducial features of probe array cartridge 720. Firmware executables 672 may then instruct linear motor 1423 to actuate sliding door 1316, opening it and enabling rollers 1106 to positionally control the probe array cartridge. Firmware executables 672 then instructs rollers 1106 to impel the probe array cartridge through transport assembly 1105 to scanner 400. Once probe array cartridge 720 is properly positioned in scanner 400 and/or received by cartridge holder 1600, firmware executables 672 instructs rollers 1106 to disengage from the probe array cartridge and retract. Rollers 1106 may also be enabled to accept the probe array cartridge from scanner 400 in a similar manner to that described above, and return it to the same or different compartment 1010 of magazine 1000 as directed by firmware executables 672.

Further illustrated in FIGS. 13 and 14 is hub base 1317, positioned beneath hub 1003 that may further be attached to a shaft connected to a timing belt pulley (not shown). The timing belt pulley may be driven via a timing belt by a motor such as linear motor 1423 or some other motor, for the purposes of advancing magazine 1000. Additionally, pin 1318 may be provided to maintain the positional orientation of cartridge magazine base 1314 such that slot 1315, and hence the loading position, does not move when cartridge magazine 1000 is advanced.

For example, cartridge magazine 1000 advances a first selected cartridge into the loading position above slot 1315 by rotating cartridge magazine 1000 about its vertical axis. A sensor may be included such as, for instance, an optical or other type of sensor that establishes that a probe array cartridge is properly aligned in the loading position. The cartridge may be lowered through cartridge transport assembly 1105 and into scanner 400 by means of rollers 1106. After the operations of scanner 400 have been completed, the probe array cartridge is reversibly transported from the scanner to the loading position in magazine 1600. The magazine advances, moving the first probe array cartridge from the loading position and moving a second probe array cartridge into the loading position where the probe array cartridge is positioned above slot 1315 and rollers 1106.

Those of ordinary skill in the relevant art will appreciate that many possible methods and components exist for the storage and automatic transport of probe array cartridges. Two examples are described in U.S. Pat. No. 6,511,277 titled "CARTRIDGE LOADER AND METHODS"; and U.S. patent application Ser. No. 10/180,588, titled "Cartridge Loader and Methods", filed Jun. 26, 2002, both of which are hereby incorporated herein by reference in their entireties for all purposes.

In some embodiments it may be desirable and/or required that scanner 400 be operated without an implementation of auto-loader 443. One embodiment of scanner 400 includes elements that allow for a user to manually load/unload one or more probe array cartridges 720. The included elements also work in conjunction with an implementation of auto-loader 443. For example, the elements may include a passive door mechanism that does not use a motor to open or close the door. Instead, a user or an implementation of auto-loader 443 may manually actuate the door. Additionally, the door may also be recessed into the housing of the scanner limiting the possibility of opening at inappropriate times.

Calibration of Scanner: It is desirable in many embodiments to calibrate the scanner to compensate for variations in components that could affect the proper acquisition of image data. Such variations could include those caused by mechanical wear or changes to one or more optical elements. Those of ordinary skill in the related art will appreciate that many optical elements may be affected by a variety of factors including temperature fluctuation, mechanical wear, component imperfections, slight changes caused by physical insult, or other of a variety of possible factors. In one implementation, scanner 400 could be initially calibrated at the factory then again during routine service in the field. Alternatively or in addition to the previous implementation, the calibration operation could be automatically performed prior to or during each scan, during the power-up routine of the scanner, or at other frequent intervals. In one embodiment, scanner 400 is calibrated for the spatial characteristics of mechanical movement as well as optical characteristics that include calibration of light collection components and radius of the light path calculations. Additionally, in the same or other embodiment, scanner 400 could be calibrated frequently to provide the most accurate images where the calibration procedures would not require user initiation or intervention.

Examples of some possible compensation mechanisms for image intensity calibration could include gain adjustments of the photo multiplier tube, power adjustments to the laser, or other adjustments to the optics and detectors. Similarly mechanical compensation to reduce error to less than one pixel could include adjustments to the speed of the scanning arm at specific points in the arc, adjustments to the movement of transport frame 505, calculated corrections to the acquired image data by scanner firmware executables 672 or scanner control and analysis executables 572 such as the implementations, Affymetrix® Microarray Suite and Affymetrix® GeneChip® Operating System.

In one possible implementation, calibration features 442 may be used to calibrate scanner 400. For example, calibration features 442 could be housed in a cartridge and inserted into scanner 400 in a similar manner to probe array cartridge 720. Calibration features 442 could include a plurality of calibration arrays or configurations that may each include various geometric chrome, fluorescent, or other type of features deposited on the inside surface of the glass and/or on the substrate of probe array 240. For example, one embodiment may include the placement of calibration features 442 such that they are in the same plane as probe array 240. In the present example, calibration features 442 may include a pattern of chrome features where a fluorescing reference medium may be deposited on top of the pattern of chrome features and loaded into scanner 400. Scanner 400 performs a calibration operation by scanning at the excitation wavelength of the fluorescent reference medium through the glass cover. One or more detectors of scanner 400 receives the emitted light from the reference medium, where the reflected light from the chrome features masks the fluorescent emissions of the reference medium. Thus the chrome pattern may be used as a negative image for calibrating scanner 400. Scanner 400 may alternatively image the calibration features by detecting the reflected light from the chrome features at the excitation wavelength that allows the chrome pattern to be used as a positive image. Additionally, as scanner 400 performs the described calibration operation, both intensity data and position data are recorded as digital data in memory. The intensity data could be based on fluorescent emissions and/or diffuse reflected light and the position data may be include image data of the chrome features, data from galvo transducer 515, and/or the known position data of the chrome features that may for instance be stored in calibration data 576.

Those of ordinary skill in the relevant art will appreciate that the geometric features of calibration features 442 may be constructed in a variety of different configurations for a variety of calibration methods. For example, one possible implementation for what may be referred to as horizontal linearity calibration may include calibration features 442 being disposed on a substrate in a grating or ladder pattern. The ladder pattern may be constructed of chrome elements of known characteristics that may resemble a series of vertical bars arranged in a horizontal pattern with each bar spaced an equal distance apart. In the present example, it may be desirable that the position of the leading edge and width of each of the bars is exactly known. Alternatively a similar configuration may used for what is referred to as vertical linearity calibration that includes the grating or ladder pattern of bars oriented in a vertical pattern instead of or in addition to the horizontal pattern. Those of ordinary skill in the related art will appreciate that the term "linearity calibration" generally refers to methods for the correction of error in one or more linear axes. For instance, horizontal linearity correction methods may include correcting for X-axis pixel placement error in an acquired image.

Continuing the example described above, the one or more linearity calibration arrays may be scanned and an image of pattern acquired along with positional data from galvo position transducer 515. Calibration executables and data 676 may then compare the image positions of calibration features 442, galvo position, and the known positions of leading edge of calibration features 442, and generate an error table that include one or more image corrections values for each pixel position of an acquired image. Calibration executables and data 676 may correct the placement of each pixel in an acquired image of probe array 240 based, at least in part, upon the error table that may, for instance, specify that a particular pixel be "moved" (e.g., associated in a database or other data storage format with a different, often a displaced, position on the array) by whole or fractional pixel increments in the plus or minus direction in the X and or Y axes. Methods of linearity correction are described in greater detail below in reference to the methods illustrated in FIGS. 20 through 22.

Also, possible implementations may include calibration features 442 as incorporated elements of probe array 240. For example, some embodiments of probe array 240 may include one or more features used for the purpose of determining the efficiency of hybridization of the biological samples with specific probes. The specific probes may detect a target molecule that is added during the experimental protocol, or alternatively may detect an mRNA signal from one or more genes known to be expressed at high levels such as, for instance, a gene important for cell structure that could include β-actin. In the present example, the image quality of the one or more features may be associated with the hybridization conditions present during an experiment. Additionally, the one or more features could be used as anchor positions for methods of geometric calibration and/or methods of collected emission intensity calibration of one or more elements of optics and detectors 100 using the collected light emitted from the hybridized probes.

In an alternative example, the biological probes in the active area of probe array 240 may serve to calibrate scanner 400. One possible advantage includes calibrating scanner 400 by using the same fluorescent tags as used to collect experimental data. Thus, by utilizing the same fluorescent tags the accuracy of the calibration method is improved by eliminating the variation caused by the characteristic emission spectra of different fluorophores. A table for geometric calibration could be constructed by finding the center pixel location of the probe array features by known methods and plotting on a graph against the known location of that center pixel of the probe feature on the X and Y axes. The differences between the measured and known expected locations are calculated as error correction values and entered on a table that may for instance be stored in calibration executables 676. Intensity calibrations could be made in the present example by using the ratio of measured emissions from what may be referred to as the match and mismatch probes.

Additionally, calibration features 442 could include one or more calibration arrays used to validate the effectiveness of both the horizontal and vertical linearity calibration methods. For example, the one or more calibration arrays may include an array that provides a pattern that perfectly corresponds to the placement of a grid pattern such as, for instance, a grid pattern that similarly corresponds to the biological probe features of probe array 240. After the pattern is imaged by scanner 400 and image correction methods are applied, the grid pattern may be placed on the image. A user may then visually see if the grid is properly aligned to the image, and if, for instance, it is not properly aligned then scanner 400 may be recalibrated for horizontal and/or vertical linearity.

Calibration features 442 may also include one or more calibration arrays for calibration of mechanical or other type or error with respect to roll 700 and pitch 703. For example, roll 700 and pitch 703 calibration may be performed by a variety of methods. One such method includes using a calibration array disposed in a housing similar to probe array cartridge 720 that is either known to be perfectly flat or that the roll and pitch error associated with the test chip has been precisely measured. Methods of measurement may include using fiducial features of probe array 240 such as, for instance, chrome border 710 or placing additional reference targets in specific positions on or around probe array 240. The specific positions could include the corners of probe array 240 where the roll and pitch of the entire probe array may be measured in addition to other characteristics such as curvature of the array or other aspects that could produce error of a probe array being perfectly flat in a plane that is perpendicular to the plane of galvo arm rotation 149. In the present example, the measured calibration array could be placed in scanner 400 and used to calibrate the instrument to correct for roll and pitch error associated with the mechanical components of scanner 400.

In an alternative example, calibration features 442 could be disposed directly upon transport frame 505 such that they could be imaged when probe array cartridge 720 is not present. A durable fluorescent material that is resistant to wear and what is commonly referred to as photo bleaching could be used as a medium for the calibration features.

In some implementations, calibration features 442 could include a known concentration of fluorophores disposed on a calibration slide or calibration array that may be used as a reference medium. Calibration features 442 may be scanned by a plurality of scanners 400 for the purpose of calibrating each of scanners 400 with respect to one another. In one embodiment the fluorophores on a calibration array have the same fluorescent properties as fluorophores used in biological experiments. For example, the same fluorophores used in biological experiments that for instance could include phycoerythrin, may be used as a fluorescent standard on a calibration array. Alternatively, other types of fluorophores may be preferable for use on a calibration array because of a variety of factors that could include long term stability of the molecule, photobleaching characteristics, or other factors that may be desirable for use in calibration procedures. In the present example, the alternative fluorophores could include kapton, or, alternatively, what those of ordinary skill in the related art refer to as quantum dot nanocrystals. The term "quantum dots" in this context generally refers to inorganic fluorescent nanocrystals and may be preferable in some implementations because of their long term stability, low photobleaching qualities, as well as their fluorescent tunability. For example, arrays of uniformly distributed single quantum dots may be fabricated by methods known to those of ordinary skill in the related art that includes what may be referred to as a self-assembly method known as spin-casting. The number of quantum dots disposed on the calibration array may be calculated so that the number of emitted photons of fluorescent light per quantum dot may be calculated using the measured fluorescence. The emitted photon per quantum dot calculation may then be used for gain calibration, instrument to instrument calibration, or other calibration methods.

Additionally in some embodiments, measured intensity error may be acquired using methods known to those of ordinary skill in the art for the measurement of the amount of noise from the photo multiplier tube (as described above in reference to the auto-zero operation), measurement of the quantum efficiency of the laser, or measurements of the transmission efficiency of the dichroic mirror. Quantum efficiency can be briefly defined as a measurement of the ratio of the energy output versus the energy input to the laser, where the lower the ratio value the more efficient the laser is. The transmission efficiency of the dichroic mirror similarly could be defined as a measurement of the amount of light at a particular wavelength that is allowed to pass through or reflected by the mirror. Each component could be calibrated or replaced if need be in order to achieve the opitmal scanner performance.

An illustrative example of one embodiment for the acquisition, storage, and method of use of linearity calibration data are provided in FIGS. 20 through 24. It will be appreciated by those of ordinary skill in the related art that the illustrative methods may be applied the both the X axis in the case of horizontal linearity, and the Y axis in the case of vertical linearity. Additionally, it may be desirable in the present embodiment to apply linearity correction methods in order to achieve a standard position error of less than +/−1 pixel. The term "position error" as used herein, refers to an error value associated with the placement of pixel intensity data at the appropriate positions in an image. For example, a position error of one pixel means that the placement of pixel intensity data should not be placed more than one pixel away from the appropriate position in an image.

Figure 20A:
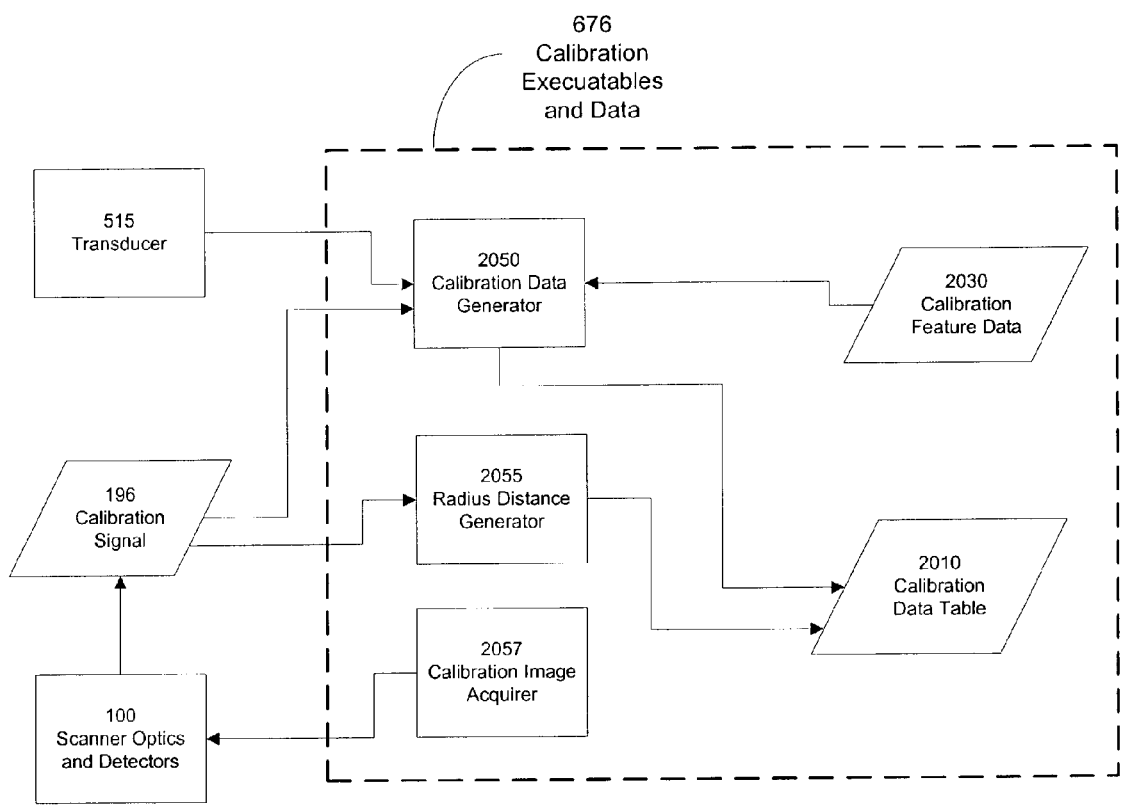
FIG. 20A is a functional block diagram of one embodiment of calibration executables of FIG. 6 including a calibration data generator, a radius distance generator, and an image correction correlator.
Figure 20B:
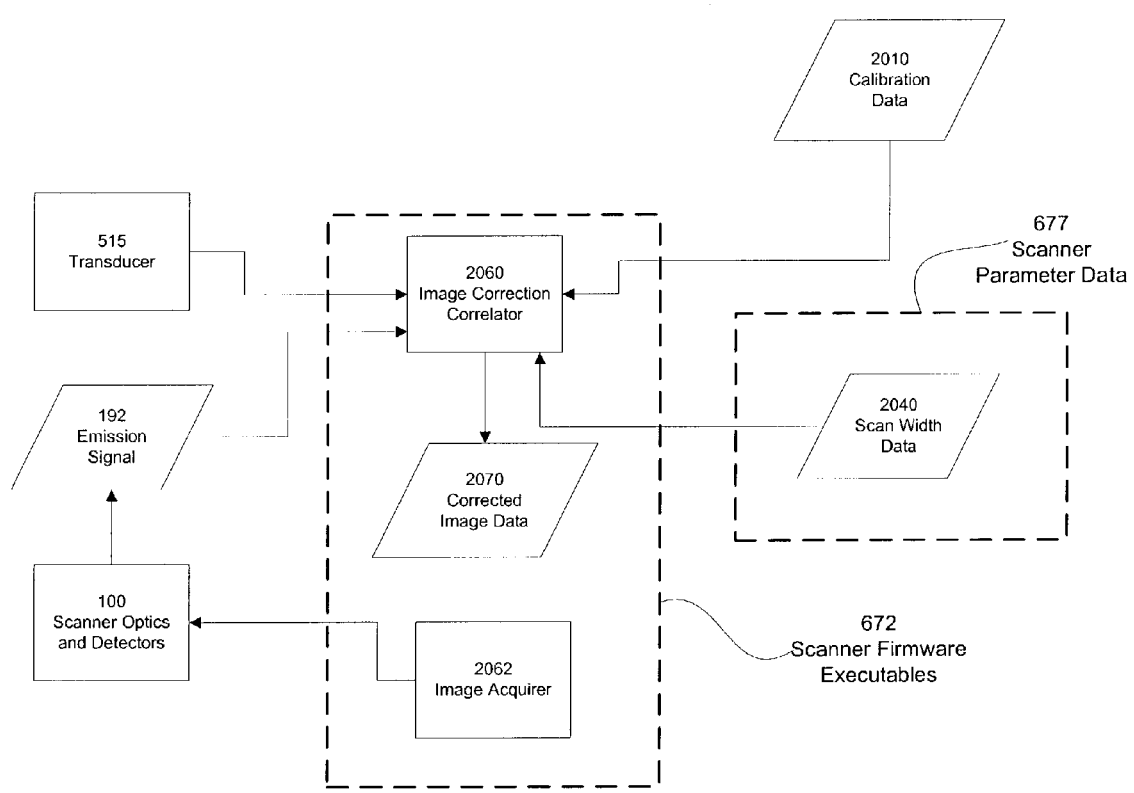
FIG. 20B is a functional block diagram of one embodiment of scanner firmware executables of FIG. 6 including an image correction correlator and an image acquirer.
Figure 21:
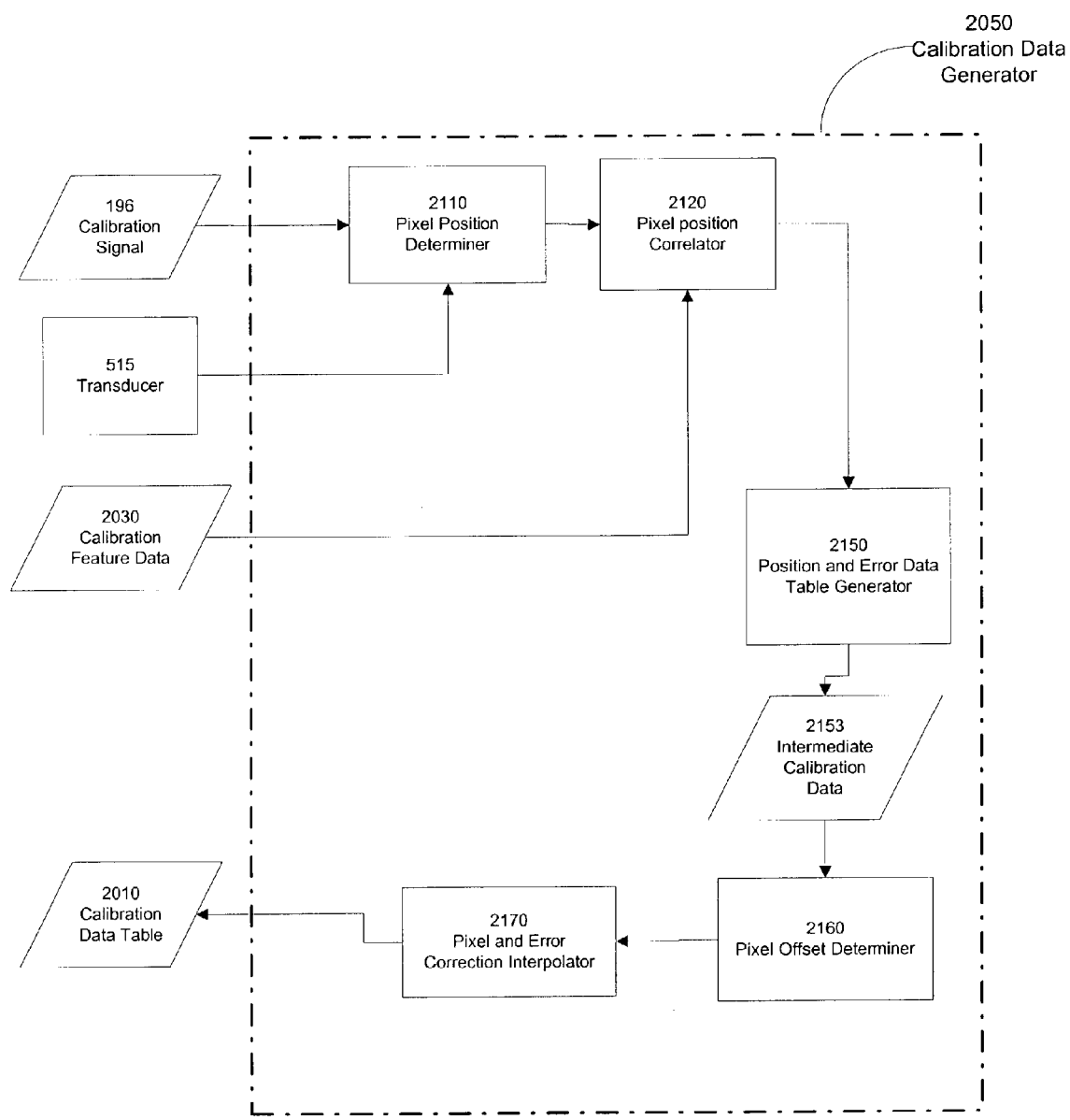
FIG. 21 is a functional block diagram of one embodiment of the calibration data generator of FIG. 20A.
Figure 22:
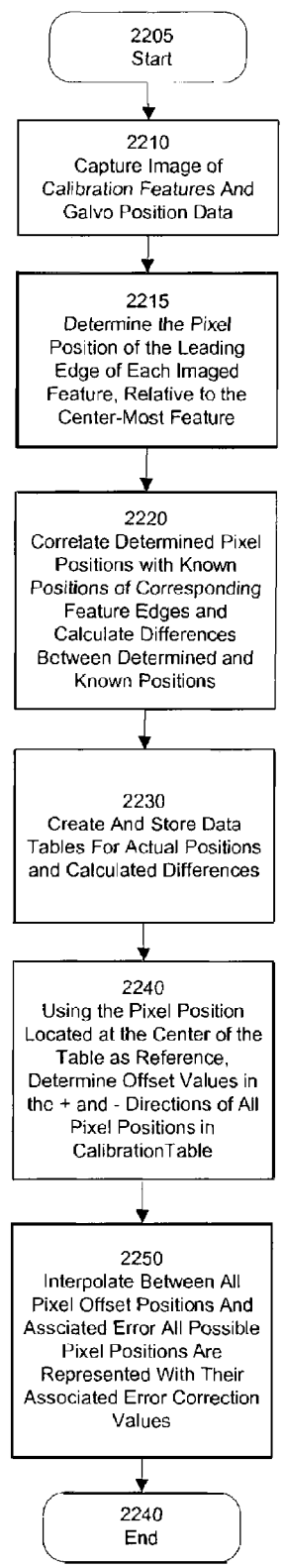
FIG. 22 is a functional block diagram of one embodiment of a method for the correction of image data using the calibration data table of FIG. 20A.
Figure 23:
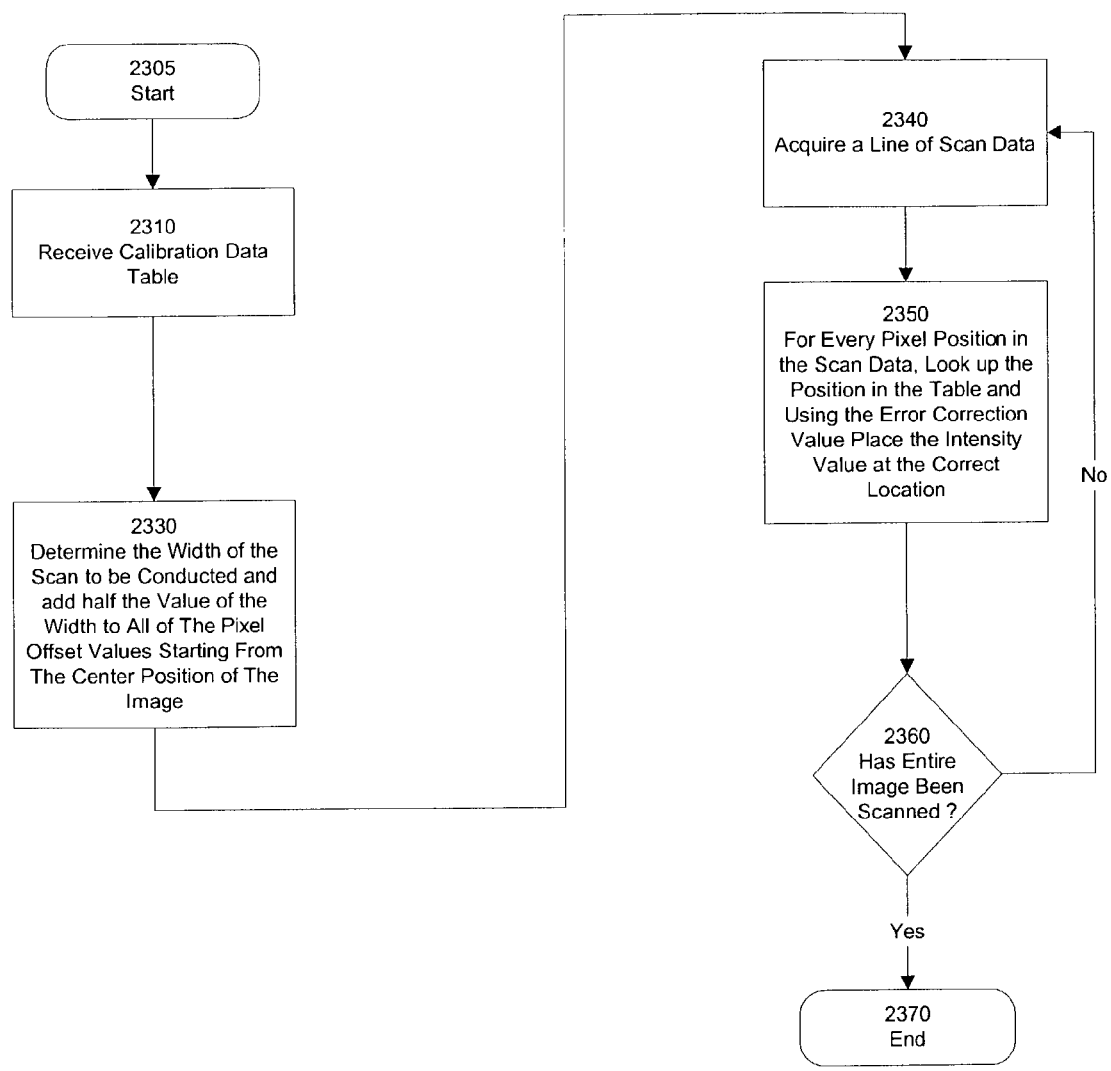
FIG. 23 is a functional block diagram of one embodiment of a method for the creation of a calibration data table.

An exemplary method for the creation of one or more linearity correction tables is illustrated in FIG. 22 with an associated functional block diagram illustrated in FIGS. 20A, 20B, and 21. Step 2205 represents the start point of the method where calibration image acquirer 2057 initiates a line scan over calibration features 442 and samples the intensity of calibration signal 196 at regular intervals such as, for example sampling at every 8-10 or other number of pixels. Calibration data generator 2050 may receive calibration signal 196 from one or more scan lines. As further illustrated in FIG. 21, pixel position determiner 2110 determines the calibration feature that is closest to the center position of the image based, at least in part, upon galvo arm position data from transducer 515. Determiner 2110 may use determined center calibration feature as a reference position.

Using similar methods as those for determining the center calibration feature, pixel position determiner 2110 determines the pixel positions of the leading edge of each calibration feature relative to the center position, illustrated as step 2215. Step 2220 illustrates a step where pixel position correlator 2120 correlates the determined pixel positions from step 2215 with the actual position data of the corresponding edges of each calibration feature, stored in calibration feature data 2030. Position and error data table generator 2150 calculates the difference between the determined and actual pixel positions as error data for the leading edge of each feature, and constructs intermediate calibration data 2153, as illustrated in step 2230.

As illustrated in step 2240, intermediate calibration data 2153 may be received by pixel offset determiner 2160. Determiner 2160 may use the determined center pixel position of data 2153 to assign pixel offset positions for each pixel position in the table. The pixel offset positions may be identified based upon their positional relationship in the (+) or (−) directions from the reference point. In the present example the (−) direction is towards the start position of the scan, and the (+) direction is towards the end position, although it will be appreciated by those of ordinary skill in the relevant art that other alternatives exist.

In some embodiments, as described in the example above, the reflected intensity may be sampled at regular intervals (i.e. every 8-10 pixels) thus data 2153 may not contain a pixel offset value and associated error correction value representing each possible pixel position. One embodiment of calibration data table 2010 includes an error correction value corresponding to each possible pixel offset position. The determined pixel offset positions and associated error correction values in data 2153 may be received by pixel and error correction interpolator 2270 as illustrated in step 2250. Interpolator 2270 may interpolate error correction values for the pixel offset positions not contained in data 2153. For example, data 2153 may contain pixel offset positions 0, −5, −12, and −21 each having an associated error correction value. In the present example, the associated error correction values for pixel offset positions −1 through −4 must be interpolated based, at least in part, upon the associated error correction values for the pixel offset positions 0 and −5 of data 2153. Whereas a different scale of interpolated error correction values may be calculated corresponding to pixel offset positions −6 through −11, based, at least in part, upon the greater range of pixel offset positions and associated error correction values. Therefore there may not be linear relationship between the error correction values in calibration data 2010. Additionally, error correction values may include partitioning fractions of pixel intensity values into different corrected pixel locations. In the present example the resulting data may be presented in calibration data table 2010, comprising a pixel offset position and an associated error correction value for any implementation of probe array 240.

Figure 24:
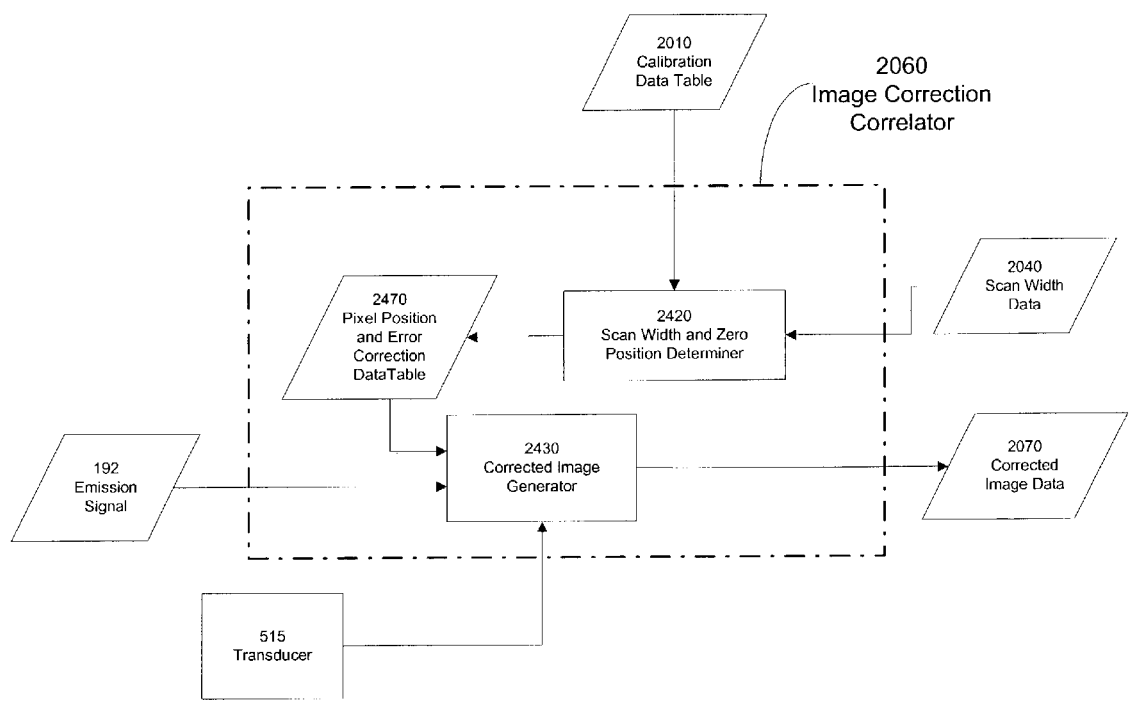
FIG. 24 is a functional block diagram of one embodiment of the image correction correlator of FIG. 20B including a corrected image generator.

In one embodiment calibration table 2010 may be used by one or more methods to correct image data for what is referred to as spatial non-linearity due to error in the scanner that could come from a variety of sources. An exemplary method is presented in FIG. 23 including elements illustrated in FIG. 24. Scan width and zero position determiner 2420 may receive table 2010 as illustrated in step 2310. In the illustrative method it may be desirable to reassign a range of the pixel offset position values so that the 0 pixel position corresponds to the start point of the X-axis scan. For instance, the range of pixel offset positions may correspond to a particular implementation of probe array 240 that may have different X-axis widths. In the presently described embodiment it is important to apply the appropriate error correction value to each pixel position of each implementation of probe array 240. The width of the scan in the X-axis for a particular implementation of probe array 240 may be determined from scan width data 2040 based, at least in part, upon one or more identifiers. Determiner 2420 calculates the value of half the total number of pixel positions of the scan width of probe array 240 and adds that value to all of the pixel offset values in calibration data table 2010 starting from the center position. The result is that the start point of the scan that formerly had a negative value (i.e. was on the (−) side of the center point), is now at the zero pixel position. For example, calibration data table 2010 contains a range of pixel offset positions that is greater than the scan width of any implementation of probe array 240. Additionally, table 2010 may have a center reference point with negative values to one side and positive values to the other. In the present example there may be a variety of different scan widths each associated with a particular implementation of probe array 240, where the distance between the start and end points of the scan vary for each particular array scan width with respect to the center point. The start point for each scan should, in the present example, begin at pixel position 0. The pixel position values may be calculated by adding half the value of the scan width to the negative pixel offset values where pixel position 0 then corresponds to the start point of the scan width and the end point is equal to the total value of the scan width. The resulting pixel positions and corresponding error correction values are illustrated in FIG. 24 as pixel position and error correction data table 2470.

Corrected image generator 2430 receives data table 2470 for use in image correction with respect to a particular implementation of probe array 240. As illustrated in step 2340, a line of scan data in the X-axis is acquired from probe array 240. Generator 2430 compares each pixel position in the acquired line of data to table 2470 and places the associated intensity value for the acquired pixel position in a corrected pixel position in an image, as illustrated in step 2350. In some implementations intensity values may be split among a plurality of corrected pixel positions. For example the error correction value for a particular acquired pixel position may specify that the associated intensity value may be divided between two or more corrected pixel positions. In the present example, the intensity value may be divided by some percentage and a portion of the intensity assigned to one corrected pixel position and the remainder is assigned to another corrected pixel position.

Decision element 2360 illustrates the step that repeats the step 2350 if the image has not been completely scanned. Otherwise the scan has been completed, and the result is corrected image data 2070.

In some implementations it may be advantageous to use galvo arm position data in the place of pixel position data to calculate the error correction table. Galvo arm position data may provide a greater range of values that may allow for more precise image correction. In the examples illustrated in FIGS. 20 through 24, transducer 515 may input data into calibration data generator 2050 and pixel and corrected image generator 2430. In the previously illustrated examples a point of pixel data may be sampled at every 8-10 pixel positions. In an alternative example, the exact position of galvo arm 200 may be taken at the same or other points using transducer 515. The resulting galvo positions may be used in the place of pixel positions for the production of calibration data 2010. Similarly, galvo position data may be substituted for pixel position data in the offset and interpolation calculations. Corrected image generator 2430 may then use the position signal from transducer 515 corresponding to the position of galvo arm 200 during the acquisition of a line of scan data to calculate the corrected pixel placements for the image data.

Alternatively, calibration executables and data 676 may use both the galvo position data and the pixel position data for calibration and error correction methods. In some implementations the galvo position data may be used to pre-correct the image data prior to the described image correction procedure using the pixel position data. For example, one method could include acquiring a line of new galvo position data prior to or during the acquisition of a line of image data. The new galvo position data may be compared with galvo/pixel position data in calibration data 2010. Any differences between the new galvo position data and the data of calibration data 2010 may represent changes in the mechanism since the last calibration and could be corrected by a variety of methods.

Figure 25:
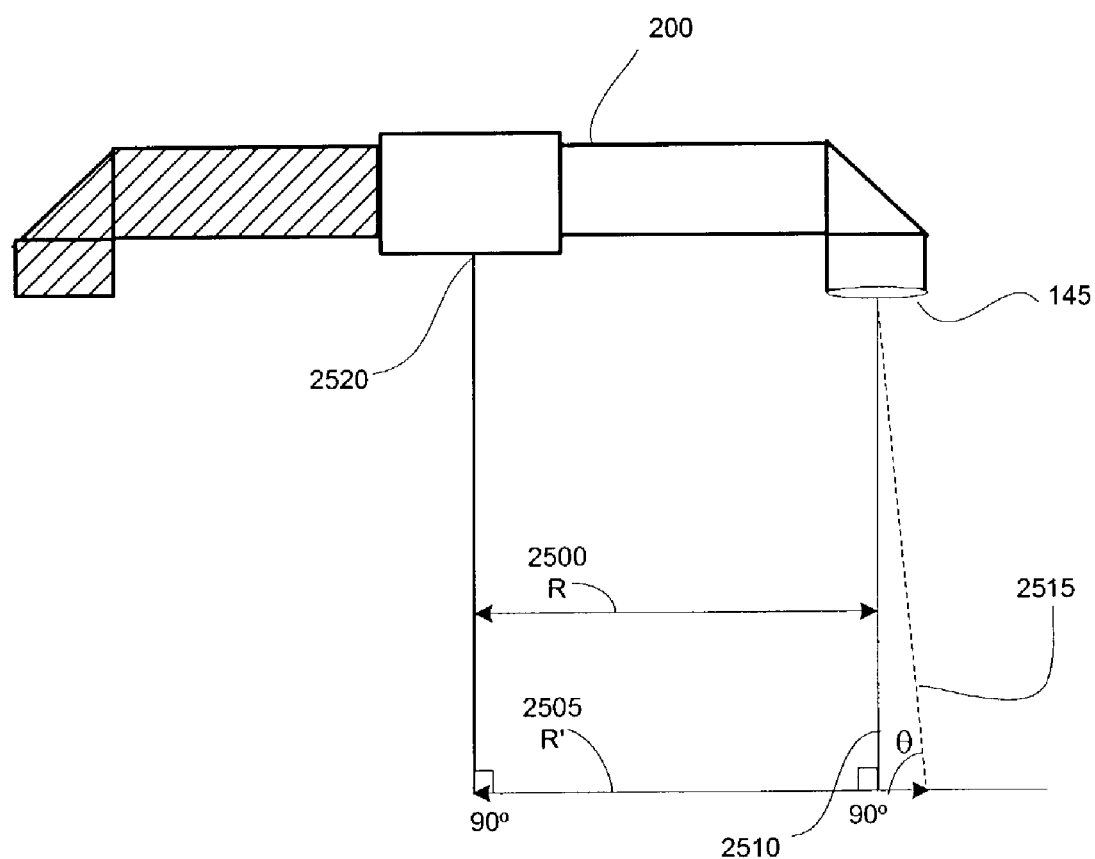
FIG. 25 is a graphical representation of one embodiment of the scanning arm of FIG. 2 illustrating the potential difference between the radius of the expected light path and the radius of the actual light path.

Another embodiment of a method using calibration features 442 may include calculating the radius of the arc of arcuate path 250. In many implementations it may be desirable to have the exact radius distance of the path of excitation beam 135 from the center of the axis of rotation of galvo arm 200 that may, for instance, be used to calculate an error value based, at least in part upon the difference between the actual radius and the expected or optimal radius that could include a radius of 25.4 mm. The radius value may be particularly useful for some image correction methods including arc correction methods that will be described in greater detail below. An illustrated example is presented in FIG. 25 of scanning arm 200 and two possible paths of excitation beam 135. Expected light path 2510 represents the expected path of excitation beam 135 emitted from center of lens 145 that meets the substrate at a 90° angle resulting in the expected radius R 3100. Radius R' 2505 represents a graphical illustration of an example where the actual radius is different than the expected radius due to actual light path 2515. Actual light path 2515 could be due to misalignment or imperfections in turning mirrors, lens 145, or a variety of other factors that may affect the optical path.

Figure 26:
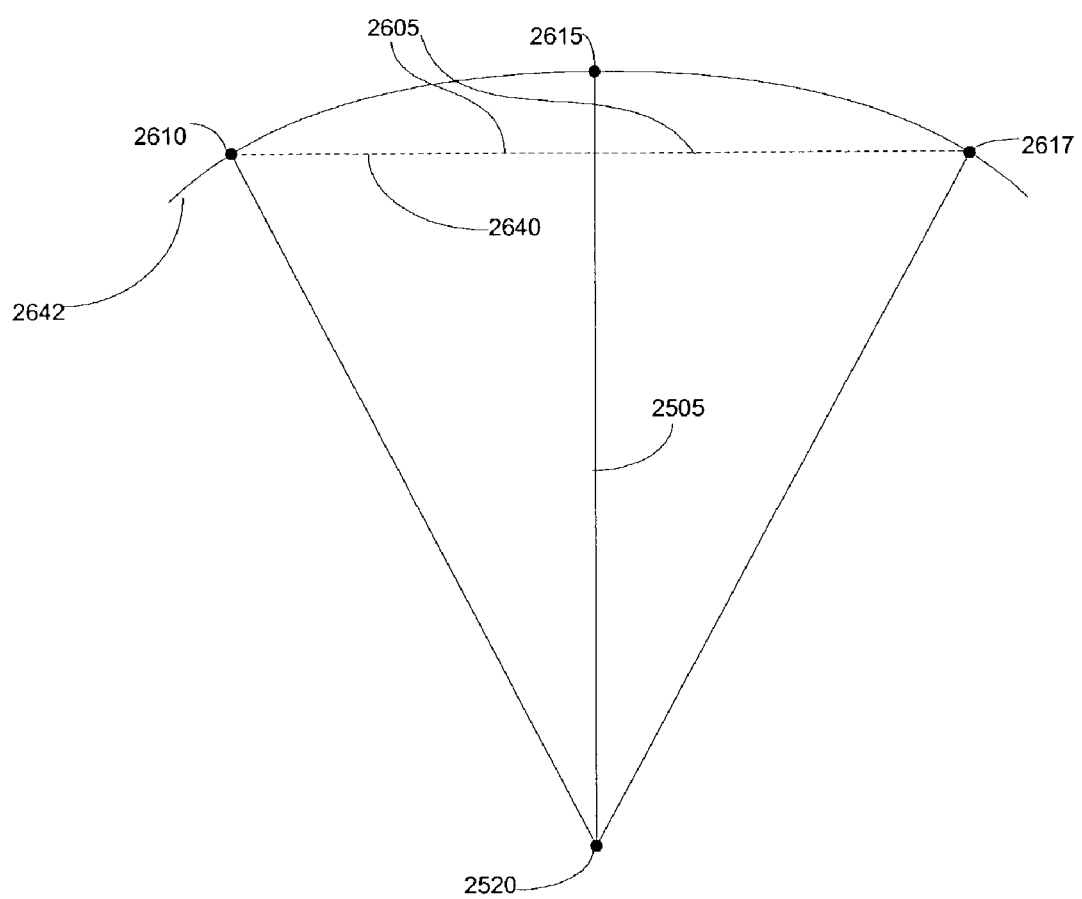
FIG. 26 is a graphical representation of one embodiment of data points from a scanning arc that are used to calculate the radius of the actual light path of FIG. 25.
Figure 27:
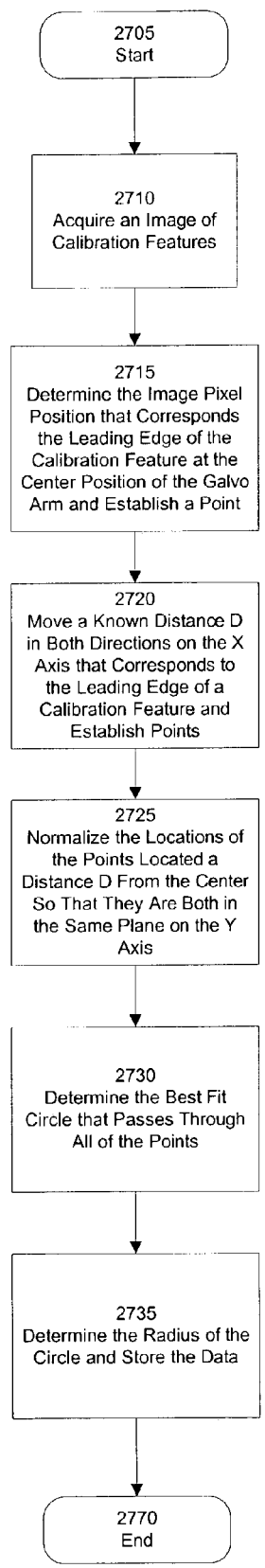
FIG. 27 is a functional block diagram of one embodiment of a method for the calculation of the radius of the actual light path of FIG. 25.

An exemplary method of determining radius R' 2505 is illustrated in FIG. 27 with a graphical depiction of particular elements illustrated in FIGS. 20 and 26. The method begins with the acquisition of an image of calibration features 442 as illustrated in step 2710 that image being received by radius distance generator 2055. Calibration features 442 may include a variety of possible implementations such as, for instance, the previously described ladder array of chrome features in reference to horizontal linearity. Generator 2055 determines the pixel position that corresponds to the leading edge of a calibration feature located in the center of the arc of arcuate path 250 and assigns that position as data point 2615. Step 2720 of the method includes generator 2055 moves a distance 2605 in both directions along the X-axis away from the center point 2615. Distance 2605 can be any distance within the scan arc that corresponds to the leading edge of a calibration feature, but one method may include distance 2605 that is near the edges of the scan arc. Data points 2610 and 2617 are established at the positions corresponding to calibration features distance 2605 away in both directions on the X-axis. Generator 2055 may normalize the positions of data points 2610 and 2617 with respect to the Y-axis so that they are in the same plane as illustrated as step 2725. The normalized positions of data points 2610 and 2617 may, in some implementations, be used to correct for any rotation of the calibration features present in the acquired image. The normalization process may include a variety of mathematical methods including the determination of the slope of line 2640 drawn between points 2610 and 2617. Those of ordinary skill in the related art will appreciate that a slope value is zero indicating that points 2610 and 2617 are in the same plane on the Y-axis. Generator 2055 may move one or more of points 2610 and 2617, while maintaining distance 2605, until the slope value is obtained. Step 2730 illustrates the step where generator 2055 mathematically calculates arc 2642 for the best fit to data points 2610, 2617, and 2615. The actual radius R' 2505 is then determined from the center point of rotation 2520 to arc 2642. The calculated actual radius 2505 may be stored in calibration feature data 2030 or other locations for use in various error correction methods, such as the method of radius adjustment described in greater detail below with respect to tool 3000.

Figure 6:
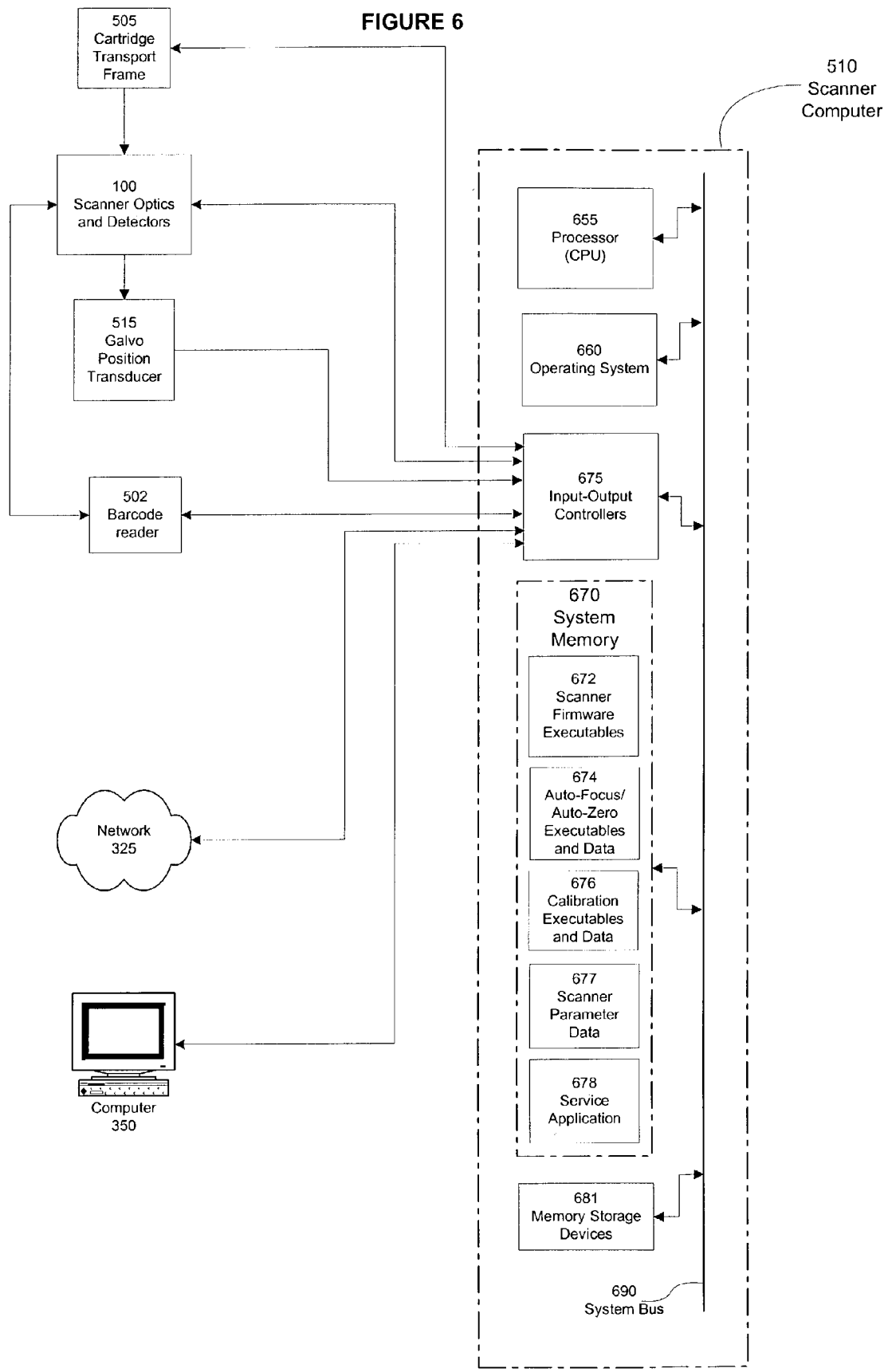
FIG. 6 is a functional block diagram of one embodiment of the scanner computer of FIG. 5 including scanner firmware, auto-focus/auto-zero software, calibration software, and service application software.

Some aspects of scanner calibration and configuration could be carried out by service application 678 that may be implemented by scanner firmware executables 672 or alternatively by scanner control and analysis executables 572. In the example illustrated in FIG. 6 in is shown as being located in system memory 670 of scanner computer 510 but alternatively may be located in computer 350 or as a stand alone application included in a local or remote computer connected via the network connection of input-output controllers 675 or other means of connection. Service personnel could use service application 678 at the factory for initial calibration and/or in the field during routine or other types of service. In one embodiment, the service application may act as a low level interface to all of the hardware components of scanner 400. For example, service application 678 could perform all of the functions required for calibration that could include but are not limited to setting the numbers and frequencies of the lasers, laser power settings, emission detector settings, as well as the previously described methods. In the present example, service application 678 could also run diagnostic tests and upload/download software and firmware as needed to scanner computer 510.

Additional elements of service application 678 could include elements that enable a user to perform installation and initial calibration procedures of scanner 400. For example, the elements could allow a user to receive a scanner from a remote source and perform the necessary set up operations in a reasonable period of time, such as one hour or less. In the present example, the scanner is completely calibrated and aligned, and fully capable of normal operation after the user installation.

Figure 30A:
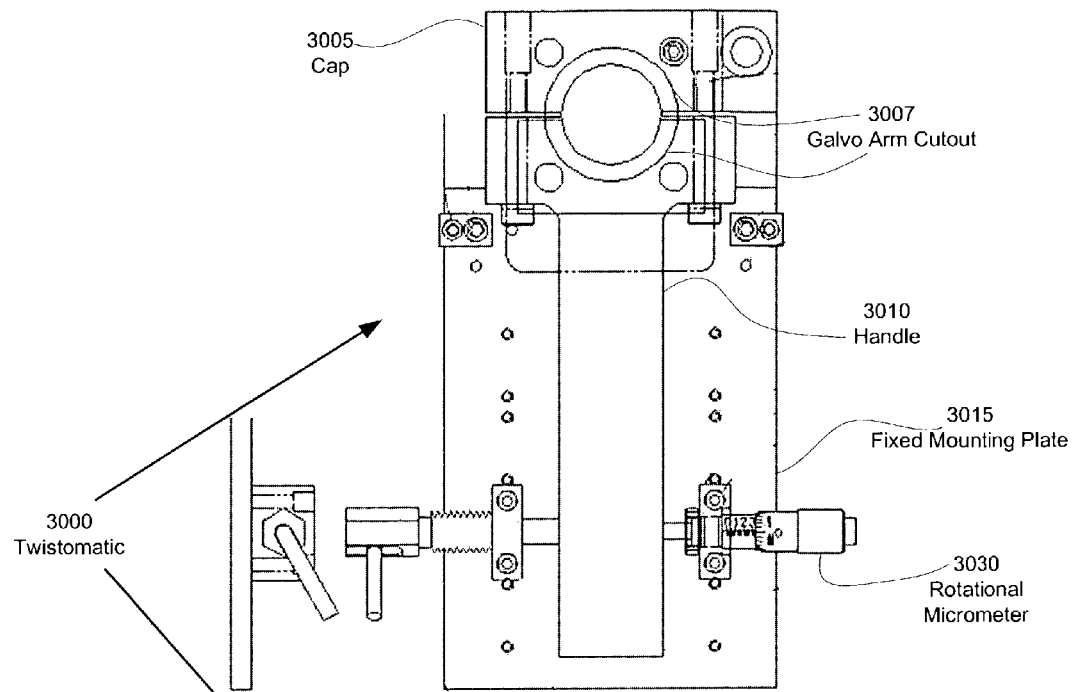
FIG. 30A is a graphical representation of one embodiment of a calibration tool including a rotational micrometer.
Figure 30B:
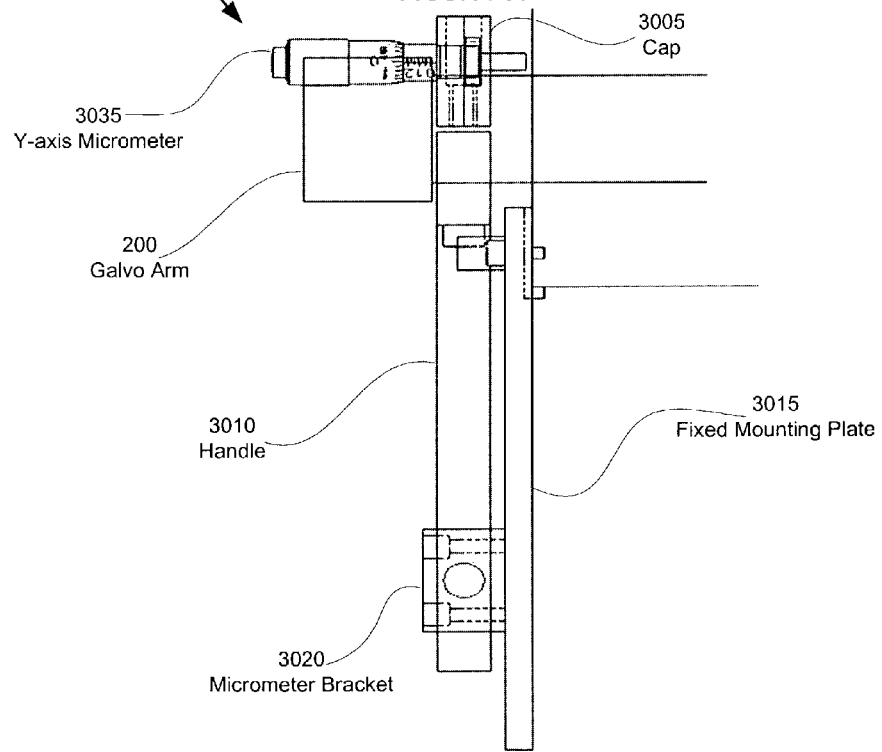
FIG. 30B is a graphical representation of one embodiment of the calibration tool of FIG. 30A including a Y-axis micrometer and the galvo arm of FIG. 2.

Some embodiments of the invention may also include hardware elements used for calibration. One such element is referred to herein as tool 3000, illustrative examples of which are illustrated in FIGS. 30A and 30B. Tool 3000 may be used for initial instrument calibration at the factory or in the field by instrument technicians or users. Tool 3000 enables the precise calibration, measurement, and adjustment of a variety of elements of scanner 400, including the Y 707 axis distance that for instance may correspond to the expected radius R 2500 of FIG. 25, and the rotational alignment of galvo arm 200 that may include the perpendicular alignment of excitation beam 135 to probe array 240. Tool 3000 may, in some embodiments, clamp onto and/or be firmly seated upon galvo arm 200. For example, tool 3000 may include galvo arm cutout 3007 that may have a shape corresponding to the outside shape of galvo arm 200. Cap 3005 may include a first half of cutout 3007 and handle 3010 may include the second half. In the present example, galvo arm 200 may be firmly held by tool 3000 by the placement of handle 3010 on the second half side of galvo arm 200 and attaching cap 3005 to the first half side of handle 3010 over galvo arm 200. In the present example galvo arm 200 may have one or more fiducial features that only allow attachment of tool 3000 to galvo arm 200 in a manner so that measurements of rotation and Y-axis distance may be reliably and repeatedly measured.

Fixed mounting plate 3015 may provide one or more reference positions used for calibration adjustments or settings. In one embodiment, fixed mounting plate 3015 may be a fixed rigid structure within scanner 400 capable of interacting with tool 3000. Alternatively, plate 3015 may be attached to scanner 400 via commonly used methods each time tool 3000 may be used for calibration or measurement methods. Tool 3000 may use a plurality of measuring devices for implementing methods for calibration and measurement that could include rotational micrometer 3030 that may be held in place by micrometer bracket 3020, and Y-axis micrometer 3035 that may be held in place by cap 3005. Both micrometers 3030 and 3035 may interact directly with elements of scanner 400 and/or plate 3015 for the purposes of precision calibration and/or measurement. For example, calibration executables and data 676 may execute a line scan over calibration features 442 and determine one or more error values corresponding to the rotational axis and Y-axis distance of galvo arm 200. Alternatively, calibration executables and data 676 may be enabled to acquire the error values from a line scan over probe array 240. Tool 3000 may be attached to galvo arm 200 so that handle 3010 and cap 3005 have rotational and Y-axis freedom of movement in relation to fixed mounting plate 3015. A user may initially use micrometers 3030 and 3035 to precisely measure the rotational and Y-axis values. The user may then release galvo arm 200 such as, for instance, by releasing a clamp or other means of holding, and use micrometers 3030 and 3035 to apply the one or more error correction values determined by calibration executables and data 676. In the present example micrometers 3030 and 3035 may directly apply the methods of error correction by pushing handle 3010 and/or cap 3005 in a first direction that may include increasing the distance from micrometers 3030 and/or 3035, or alternatively allowing the spring rate of one or more elements to bring handle 3010 and/or cap 3005 closer (i.e. decreasing the distance to micrometers 3030 and 3035). The user may reapply the means of holding galvo arm 200 and verify the values on micrometers 3030 and 3035 and release tool 3000.

Having described various embodiments and implementations, it should be apparent to those skilled in the relevant art that the foregoing is illustrative only and not limiting, having been presented by way of example only. Many other schemes for distributing functions among the various functional elements of the illustrated embodiment are possible. The functions of any element may be carried out in various ways in alternative embodiments.

Also, the functions of several elements may, in alternative embodiments, be carried out by fewer, or a single, element. Similarly, in some embodiments, any functional element may perform fewer, or different, operations than those described with respect to the illustrated embodiment. Also, functional elements shown as distinct for purposes of illustration may be incorporated within other functional elements in a particular implementation. Also, the sequencing of functions or portions of functions generally may be altered. Certain functional elements, files, data structures, and so on may be described in the illustrated embodiments as located in system memory of a particular computer. In other embodiments, however, they may be located on, or distributed across, computer systems or other platforms that are co-located and/or remote from each other. For example, any one or more of data files or data structures described as co-located on and "local" to a server or other computer may be located in a computer system or systems remote from the server. In addition, it will be understood by those skilled in the relevant art that control and data flows between and among functional elements and various data structures may vary in many ways from the control and data flows described above or in documents incorporated by reference herein. More particularly, intermediary functional elements may direct control or data flows, and the functions of various elements may be combined, divided, or otherwise rearranged to allow parallel processing or for other reasons. Also, intermediate data structures or files may be used and various described data structures or files may be combined or otherwise arranged. Numerous other embodiments, and modifications thereof, are contemplated as falling within the scope of the present invention as defined by appended claims and equivalents thereto.

What is claimed is:

1. A scanning system, comprising:
one or more optical elements constructed and arranged to direct a excitation beam at a probe array;
one or more detectors constructed and arranged to receive reflected intensity data responsive to the excitation beam, wherein the reflected intensity data is responsive, at least in part, to a focusing distance between an optical element and the probe array;
a transport frame constructed and arranged to adjust the focusing distance in a first direction with respect to the probe array;
an auto-focuser constructed and arranged to determine a best plane of focus based, at least in part, upon one or more characteristics of the reflected intensity data as received at two or more focusing distances, wherein the one or more characteristics includes a slope value, and the best plane of focus is based, at least in part, upon a maximum value of the slope value;
and wherein:
the one or more detectors are further constructed and arranged to receive a plurality of pixel intensity values based, at least in part, upon detected emissions from a plurality of probe features disposed on the probe array at the best plane of focus; and
the system further comprises an image generator constructed and arranged to associate each of the pixel intensity values with one or more image pixel positions of a probe array based, at least in part, upon one or more position correction values.

2. A method, comprising the acts of:
directing an excitation beam at a probe array;
receiving reflected intensity data responsive to the excitation beam, wherein the intensity data is responsive, at least in part, to a focusing distance between an optical element and the probe array;
adjusting the focusing distance in a first direction with respect to the probe array;
repeating the steps of receiving and adjusting for a predetermined number of iterations, wherein the predetermined number of iterations is based, at least in part, on an anticipated error associated with the reflected intensity data; and
determining a best plane of focus based, at least in part, upon one or more characteristics of the reflected intensity data at the adjusted focusing distances.

3. The method of claim 2, wherein: the first direction is away from or toward the probe array.

4. The method of claim 2, wherein:
the anticipated error associated with the reflected intensity data is inversely related to the predetermined number of iterations.

5. The method of claim 2, wherein:
the reflected intensity data are responsive to reflection of the excitation beam from one or more focus features.

6. The method of claim 5, wherein:
the reflected intensity data correspond to one or more reflection spots.

7. The method of claim 6, wherein:
the best plane of focus is based, at least in part, upon associating the one or more spots with one or more characteristics of a beam waist.

8. The method of claim 5, wherein:
the one or more focus features are positioned outside an active area and the one or more probe features are positioned inside the active area.

9. The method of claim 5, wherein:
the one or more focus features includes a chrome border.

10. The method of claim 2, wherein:
the one or more characteristics includes a slope value.

11. The method of claim 2, wherein:
the one or more characteristics includes a slope value, and the best plane of focus is based, at least in part, upon a maximum value of the slope value.

12. A scanning system, comprising:
one or more optical elements constructed and arranged to direct an excitation beam at a probe array;
one or more detectors constructed and arranged to receive reflected intensity data responsive to the excitation beam, wherein the intensity data is determined, at least in part, by a focusing distance between an optical element and the probe array;
an auto-focuser constructed and arranged to determine a best plane of focus based, at least in part, upon one or more characteristics of the reflected intensity data as received at two or more focusing distances, such that receipt of reflected intensity data and adjustment of the plane of focus occurs in a predetermined number of iterations, and wherein the predetermined number of iterations is based, at least in part, on an anticipated error associated with the reflected intensity data.

13. The scanning system of claim 12, wherein:
the first direction is away from or toward the probe array.

14. The scanning system of claim 12, wherein:
the anticipated error associated with the reflected intensity data is inversely related to the predetermined number of iterations.

15. The scanning system of claim 12, wherein:
the reflected intensity data are responsive to reflection of the excitation beam from one or more focus features.

16. The scanning system of claim 15, wherein:
the reflected intensity data correspond to one or more reflection spots.

17. The scanning system of claim 16, wherein:
the best plane of focus is based, at least in part, upon associating the one or more spots with one or more characteristics of a beam waist.

18. The scanning system of claim 15, wherein:
the one or more focus features are positioned outside an active area, and the one or more probe features are positioned inside the active area.

19. The scanning system of claim 15, wherein:
the one or more focus features includes a chrome border.

20. The scanning system of claim 12, wherein:
the one or more characteristics includes a slope value.

21. The scanning system of claim 12, wherein:
the one or more characteristics includes a slope value, and the best plane of focus is based, at least in part, upon a maximum value of the slope value.

* * * * *